United States Patent
Sharma et al.

(10) Patent No.: US 12,083,105 B2
(45) Date of Patent: Sep. 10, 2024

(54) COMPOSITIONS AND METHODS FOR TREATING ADULT-ONSET NEURONAL CEROID LIPOFUSCINOSIS (KUFS DISEASE)

(71) Applicant: CORNELL UNIVERSITY, Ithaca, NY (US)

(72) Inventors: Manu Sharma, Tappan, NY (US); Nima N. Naseri, Philadelphia, PA (US)

(73) Assignee: Cornell University, Ithaca, NY (US)

( * ) Notice: Subject to any disclaimer, the term of this patent is extended or adjusted under 35 U.S.C. 154(b) by 596 days.

(21) Appl. No.: 17/155,200

(22) Filed: Jan. 22, 2021

(65) Prior Publication Data
US 2021/0290602 A1    Sep. 23, 2021

Related U.S. Application Data

(60) Provisional application No. 62/993,131, filed on Mar. 23, 2020.

(51) Int. Cl.
| | | |
|---|---|---|
| *A61K 31/44* | (2006.01) | |
| *A61K 9/00* | (2006.01) | |
| *A61K 31/16* | (2006.01) | |
| *A61K 45/06* | (2006.01) | |
| *A61P 25/28* | (2006.01) | |

(52) U.S. Cl.
CPC ............ *A61K 31/44* (2013.01); *A61K 9/0014* (2013.01); *A61K 9/0019* (2013.01); *A61K 9/0053* (2013.01); *A61K 9/0073* (2013.01); *A61K 31/16* (2013.01); *A61K 45/06* (2013.01); *A61P 25/28* (2018.01)

(58) Field of Classification Search
CPC ...... A61K 31/44; A61K 9/0073; A61K 31/16; A61P 25/28
See application file for complete search history.

(56) References Cited

U.S. PATENT DOCUMENTS

2010/0298394 A1* 11/2010 Steiner ...................... A61P 9/10
548/342.1
2014/0179789 A1* 6/2014 Frey, II .................. A61K 38/30
514/616

OTHER PUBLICATIONS

Abbruzzese, G. et al. "A pilot trial of deferiprone for neurodegeneration with brain iron accumulation." Haematologica 2011, vol. 96, pp. 1708-1711.
Anderson, G. W. et al. "Human pathology in NCL." Biochim Biophys Acta 2013, vol. 1832, pp. 1807-1826.
Baldus, W. P. et al. "Deferoxamine-chelatable iron in hemochromatosis and other disorders of iron overload." Mayo Clinic 1978 proceedings 53, pp. 157-165.
Benitez, B.A. et al. "Exome-sequencing confirms DNAJC5 mutations as cause of adult neuronal ceroid-lipofuscinosis." PLoS One 2011, vol. 6, Issue 11, e26741.

(Continued)

*Primary Examiner* — San Ming R Hui
(74) *Attorney, Agent, or Firm* — Foley & Lardner LLP

(57) ABSTRACT

The present technology relates to methods for treating, preventing, and/or ameliorating diseases associated with ectopic iron-sulfur (Fe—S) cluster formation or ectopic iron-sulfur (Fe—S) cluster binding, such as adult-onset neuronal ceroid lipofuscinosis (ANCL or Kufs disease) comprising administering a therapeutically effective amount of an iron chelator to a subject in need thereof. Kits for use in practicing the methods are also provided.

10 Claims, 22 Drawing Sheets

Specification includes a Sequence Listing.

(56) References Cited

OTHER PUBLICATIONS

Braun, J. E. et al. "Cysteine string protein, a DnaJ family member, is present on diverse secretory vesicles." Neuropharmacology 1995, vol. 34, pp. 1361-1369.
Chamberlain, L. H. et al. "Activation of the ATPase activity of heat-shock proteins Hsc70/Hsp70 by cysteine-string protein." Biochem J 1997 vol. 322 (Pt 3), pp. 853-858.
Chamberlain, L. H. et al. "The cysteine-string domain of the secretory vesicle cysteine-string protein is required for membrane targeting." Biochem J. 1998, vol. 335 (Pt 2), pp. 205-209.
Chandra, S. et al. "Alpha-synuclein cooperates with CSPalpha in preventing neurodegeneration." Cell 2005, vol. 123, pp. 383-396.
Dailey, H. A. et al. "Human ferrochelatase is an iron-sulfur protein." Biochemistry 1994, vol. 33, pp. 403-407.
Diez-Ardanuy, C. et al. "A cluster of palmitoylated cysteines are essential for aggregation of cysteine-string protein mutants that cause neuronal ceroid lipofuscinosis." 7, 10 (2017).
Dull, T. et al. "A third-generation lentivirus vector with a conditional packaging system." Journal of virology 1998 vol. 72, pp. 8463-8471.
Fernandez-Chacon, R. et al. "The synaptic vesicle protein CSP alpha prevents presynaptic degeneration." Neuron 2004 vol. 42, pp. 237-251.
Firdaus, W.J. et al. "Huntingtin inclusion bodies are iron-dependent centers of oxidative events." The FEBS journal 2006 vol. 273, pp. 5428-5441.
Fogo, J. K. et al. "Spectrophotometric Determination of Hydrogen Sulfide—Methylene Blue Method." Anal Chem 1949, vol. 21, pp. 732-734.
Fredenburg, A.M. et al. "The pharmacokinetics and blood-brain barrier permeation of the chelators 1,2 dimethly-, 1,2 diethyl-, and 1-[ethan-1'ol]-2-methyl-3-hydroxypyridin-4-one in the rat." Toxicology 1996 vol. 108, pp. 191-199.
Goebel, H. "Adult neuronal ceroid-lipofuscinosis." Clin Neuropathol 1989, vol. 8, pp. 109-119.
Greaves, J. et al. "Palmitoylation-induced aggregation of cysteine-string protein mutants that cause neuronal ceroid lipofuscinosis." J Biol Chem 2012, vol. 287, pp. 37330-37339.
Gunderson, C. B. et al. "Extensive lipidation of a Torpedo cysteine string protein." J Biol Chem 1994, vol. 269, pp. 19197-19199.
Habgood, M. D. et al. "Investigation into the correlation between the structure of hydroxypyridinones and blood-brain barrier permeability." Biochem Pharmacol 1999, vol. 57, pp. 1305-1310.
Hall, N. A. et al. "Lysosomal storage of subunit c of mitochondrial ATP synthase in Batten's disease (ceroid-lipofuscinosis)." Biochem J 1991, vol. 275 (Pt 1), pp. 269-272.
Henderson, M. X. et al. "Neuronal ceroid lipofuscinosis with DNAJC5/CSPalpha mutation has PPT1 pathology and exhibit aberrant protein palmitoylation." Acta Neuropathol, (2015).
Hoffbrand, A. V. et al. "Role of deferiprone in chelation therapy for transfusional iron overload." Blood 2003 vol. 102, pp. 17-24.
Ikegaki, N. et al. "Glutaraldehyde fixation of the primary antibody-antigen complex on nitrocellulose paper increases the overall sensitivity of immunoblot assay." Journal of Immunological Methods. 1989, vol. 124, pp. 205-210.
Johansson, C. et al. "Reversible sequestration of active site cysteines in a 2Fe—2S-bridged dimer provides a mechanism for glutaredoxin 2 regulation in human mitochondria." J Biol Chem 2007 vol. 282, pp. 3077-3082.
Jordan, M. et al. "Transfecting mammalian cells: optimization of critical parameters affecting calcium-phosphate precipitate formation." Nucleic acids research 1996, vol. 24, pp. 596-601.
Josephson, S. A. et al. "Autosomal dominant Kufs' disease: a cause of early onset dementia." J Neurol Sci 2001, vol. 188, pp. 51-60.
Kohan, S. A. et al. "Cysteine string protein immunoreactivity in the nervous system and adrenal gland of rat." J Neurosci 1995, vol. 15, pp. 6230-6238.
Lois, C. et al. Germline transmission and tissue-specific expression of transgenes delivered by lentiviral vectors. Science 2002 vol. 295, pp. 868-872.
Malkin, R. et al. "The reactivity of clostridial ferredoxin with iron chelating agents and 5,5'-dithiobis-2-nitrobenzoic acid." Biochemistry 1967, vol. 6, pp. 3880-3891.
Martin, J. J. "Adult type of neuronal ceroid lipofuscinosis." Dev Neurosci 1991, vol. 13, pp. 331-338.
Maximov, A. et al. "Monitoring synaptic transmission in primary neuronal cultures using local extracellular stimulation." J Neurosci Methods 2007 vol. 161, pp. 75-87.
Mesecke, N. et al. "Two novel monothiol glutaredoxins from *Saccharomyces cerevisiae* provide further insight into iron-sulfur cluster binding, oligomerization, and enzymatic activity of glutaredoxins." Biochemistry 2008, vol. 47, pp. 1452-1463.
Netz, D. J. et al. "Maturation of cytosolic and nuclear iron-sulfur proteins." Trends in cell biology 2014 vol. 24, pp. 303-312.
Nguyen, T. et al. "Clioquinol down-regulates mutant huntingtin expression in vitro and mitigates pathology in a Huntington's disease mouse model." Proc Natl Acad Sci USA 2005, vol. 102, pp. 11840-11845.
Noskova, L. et al. "Mutations in DNAJC5, encoding cysteine-string protein alpha, cause autosomal-dominant adult-onset neuronal ceroid lipofuscinosis." Am J Hum Genet 2011, vol. 89, pp. 241-252.
Pang, Z. P. et al. "Induction of human neuronal cells by defined transcription factors." Nature 2011 vol. 476, pp. 220-223.
Piga, A. et al. Deferiprone. Annals of the New York Academy of Sciences 2010, vol. 1202, pp. 75-78.
Riemer, J. et al. "Colorimetric ferrozine-based assay for the quantitation of iron in cultured cells." Analytical Biochemistry 2004, vol. 331, pp. 370-375.
Sanders, S.S. et al. "Aberrant palmitoylation in Huntington disease." Biochem Soc Trans 2015, vol. 43, pp. 205-210.
Sharma, M. et al. "CSPa knockout causes neurodegeneration by impairing SNAP-25 function." EMBO 2012 J 31, pp. 829-841.
Sharma, M. et al. "CSPa promotes SNARE-complex assembly by chaperoning SNAP-25 during synaptic activity." Nat Cell Biol 2011, vol. 13, pp. 30-39.
Sudhof, T.C. et al. "Membrane Fusion: Grappling with SNARE and SM Proteins." Science 2009, vol. 323, pp. 474-477.
Tamarit, J. et al. "Colorimetric assay for the quantitation of iron in yeast." Analytical biochemistry 2006, vol. 351, 149-151.
Tobaben, S. et al. "A trimeric protein complex functions as a synaptic chaperone machine." Neuron 2001, vol. 31, pp. 987-999.
Tong, W.-H. et al. "Functions of mitochondrial ISCU and cytosolic ISCU in mammalian iron-sulfur cluster biogenesis and iron homeostasis." Cell 2006 Metab 3, pp. 199-210.
Umbach, J. A. et al. "Presynaptic dysfunction in *Drosophila* csp mutants." Neuron 1994, vol. 13, pp. 899-907.
Velinov, M. et al. "Mutations in the gene DNAJC5 cause autosomal dominant Kufs disease in a proportion of cases: study of the Parry family and 8 other families." PLoS 2012, One 7, e29729.
Wernig, M. et al. "Tau EGFP embryonic stem cells: an efficient tool for neuronal lineage selection and transplantation." J Neurosci Res, 2002, vol. 69, pp. 918-924.
Yanai, A. et al. "Palmitoylation of huntingtin by HIP14 is essential for its trafficking and function." Nat Neurosci 2006 vol. 9, pp. 824-831.
Yee, J.K. et al. "A general method for the generation of high-titer, pantropic retroviral vectors: highly efficient infection of primary hepatocytes." Proc Natl Acad Sci USA 1994, vol. 91, pp. 9564-9568.
Zhang, Y. Q. et al. "Identification of CSPalpha clients reveals a role in dynamin 1 regulation." Neuron 2012 vol. 74, pp. 136-150.
Zhang, Y.-Q. et al. "Oligomerization of Cysteine String Protein alpha mutants causing adult neuronal ceroid lipofuscinosis." Biochim Biophys Acta 2014, vol. 1842, pp. 2136-2146.
Zinsmaier, K. E. et al. "A cysteine-string protein is expressed in retina and brain of *Drosophila*." J Neurogenet 1990, vol. 7, pp. 15-29.

(56) References Cited

OTHER PUBLICATIONS

Zinsmaier, K. E. et al. "Paralysis and early death in cysteine string protein mutants of *Drosophila*." Science 1994, vol. 263, pp. 977-980.

* cited by examiner

HEK293T expression

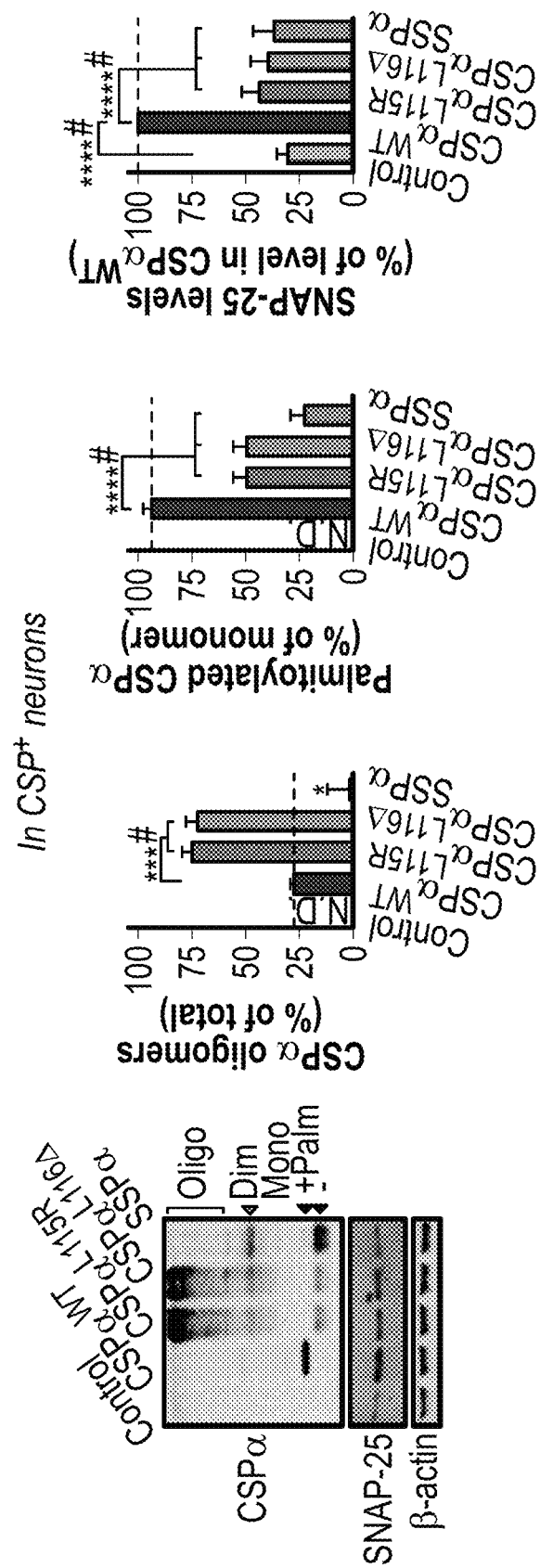
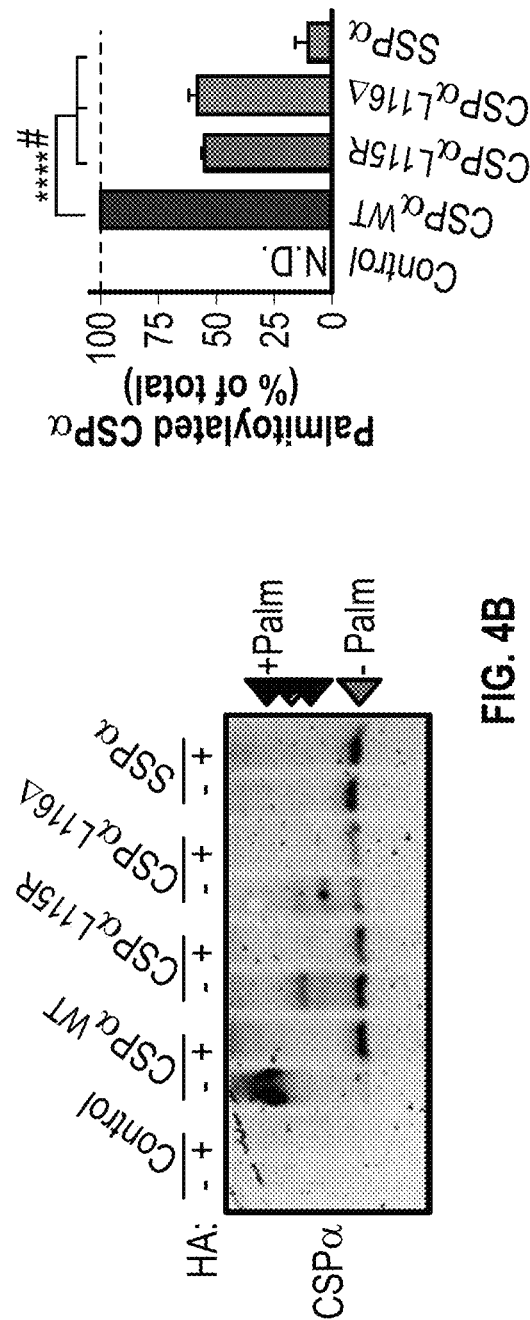
FIG. 4A
FIG. 4B

COMPOSITIONS AND METHODS FOR TREATING ADULT-ONSET NEURONAL CEROID LIPOFUSCINOSIS (KUFS DISEASE)

CROSS-REFERENCE TO RELATED PATENT APPLICATIONS

This application claims the benefit of and priority to U.S. Provisional Appl. No. 62/993,131, filed Mar. 23, 2020, the contents of which are incorporated by reference herein in its entirety.

GOVERNMENT SUPPORT

This invention was made with government support under grant number F31 NS098623-01A1, awarded by the National Institute of Neurological Disorders and Stroke (NINDS)/National Institute of Health (NIH) and 1R01 AG052505-01, awarded by the National Institute on Aging (NIA)/NIH. The government has certain rights in the invention.

TECHNICAL FIELD

The present disclosure relates generally to methods for treating, preventing, and/or ameliorating diseases associated with ectopic iron-sulfur (Fe—S) cluster formation or ectopic iron-sulfur (Fe—S) cluster binding, such as adult-onset neuronal ceroid lipofuscinosis (ANCL or Kufs disease) comprising administering a therapeutically effective amount of an iron chelator to a subject in need thereof. Kits for use in practicing the methods are also provided.

SEQUENCE LISTING

The instant application contains a Sequence Listing which has been submitted electronically in ASCII format and is hereby incorporated by reference in its entirety. Said ASCII copy, created on Mar. 29, 2021, is named 093873-1305_SL.txt and is 1,025 bytes in size.

BACKGROUND

The following description of the background of the present technology is provided simply as an aid in understanding the present technology and is not admitted to describe or constitute prior art to the present technology.

Adult neuronal ceroid lipofuscinosis (ANCL or Kufs disease) is a rare inherited neurological disorder. Signs and symptoms begin anytime between adolescence and late adulthood, usually around age 30. Kufs disease is characterized by progressive, widespread neurodegeneration and intra-neuronal accumulation of autofluorescent lipopigments, called lipofuscin. The clinical presentation of Kufs disease includes one or more of progressive dementia, epilepsy, cerebellar and/or extrapyramidal symptoms, myoclonus, and vision loss. Kufs disease patients also experience behavioral abnormalities. The condition leads to death within 15 years of the onset of symptoms. ANCL or Kufs disease is believed to be caused by autosomal dominant mutations in the DNAJC5 gene (Nosková et al., *Am J Hum Genet.* 89(2): 241-252 (2011)) and no treatment is currently available for this rapidly progressing and lethal neurodegenerative disease.

DNAJC5 gene is a member of the DnaJ heat shock protein family (Hsp40). Specifically, DNAJC5 is member 5 of subfamily C of DnaJ heat shock protein family. Human DNAJC5 gene is located on the long arm of chromosome 20 (20q13.33). The gene is 40,867 bases in length. DNAJC5 gene encodes the cysteine string protein alpha (CSPα), a 34 kDa protein, which is 198 amino acids in length. CSPα protein is abundant in neural tissue and is localized to synaptic and clathrin coated vesicles. CSPα protein plays a role in the transmission of nerve impulses. Specifically, CSPα is part of a group (complex) of proteins that is found in the synaptic vesicles. CSPα forms a complex with Syntaxin 1A, a plasma membrane SNARE (soluble N-ethylmaleimide-sensitive factor attachment protein receptor) critical for neurotransmission. CSPα is involved in recycling proteins that are involved in nerve impulse transmission by re-folding misshapen proteins so that they can be used in additional transmissions.

Accordingly, there is an urgent need to identify therapeutic agents that are effective in treating ANCL or Kufs disease.

SUMMARY OF THE PRESENT TECHNOLOGY

In one aspect, the present disclosure provides a method for preventing or treating a disease associated with ectopic iron-sulfur (Fe—S) cluster formation, or a disease associated with ectopic binding of one or more proteins to iron-sulfur (Fe—S) clusters in a subject in need thereof, comprising administering to the subject a therapeutically effective amount of an iron chelator. Examples of iron chelators include, but are not limited to, deferoxamine, desferrithiocin, deferiprone, deferasirox, Apo6619, VK28, pyridoxal isonicotinoyl hydrazone, dexrazoxane, triapine, clioquinol, tachpyr, O-trensox, flavan-3-ol, curcumin, apocynin, kolaviron, floranol, baicalein, baicalin, di-2-pyridylketone thiosemicarbazone, ligustrazine, quercetin, epigallocatechin gallate, theaflavin, phytic acid, genistein, dimercaptosuccinic acid, 2,3-dimercapto-1-propanesulfonic acid (DMPS), alpha lipoic acid (ALA), or any pharmaceutically acceptable salts thereof. In some embodiments, the subject harbors a dominant negative CSPα mutation, such as CSPα$^{L115R}$ or CSPα$^{L116\Delta}$. Additionally or alternatively, in some embodiments, the disease associated with ectopic iron-sulfur (Fe—S) cluster formation, or the disease associated with ectopic binding of one or more proteins to iron-sulfur (Fe—S) cluster is Kufs disease or Huntington's disease. Kufs disease may be Type A Kufs disease or Type B Kufs disease. Additionally or alternatively, in some embodiments, the disease associated with ectopic iron-sulfur (Fe—S) cluster formation, or the disease associated with ectopic binding of one or more proteins to iron-sulfur (Fe—S) cluster is characterized by reduced SNAP-25 proteins levels, decreased SNARE-complex assembly, or elevated levels of lipofuscin and/or mitochondrial ATP-synthase subunit C (ATP5G) in neurons. In certain embodiments, the subject exhibits reduced CSPα palmitoylation in neurons and/or increased CSPα oligomerization.

In any and all embodiments of the method, the subject harbors at least one mutation in one or more genes selected from the group consisting of CLN6, PPT1, DNAJC5, CTSF, CLN5, GRN, and CLN3. Additionally or alternatively, in some embodiments, the subject exhibits at least one symptom selected from the group consisting of progressive dementia, epilepsy, cerebellar and/or extrapyramidal symptoms, myoclonus, vision loss, seizures, ataxia, tremors and tics, dysarthria (speech difficulties), confusion, involuntary movements (e.g., tics, tremors, facial dyskinesia), and psychotic behaviour.

Additionally or alternatively, in some embodiments, the iron chelator is administered intravenously, intramuscularly, intraarterially, intrathecally, intracapsularly, intraorbitally, intradermally, intraperitoneally, transtracheally, subcutaneously, intracerebroventricularly, orally, topically, or intranasally. In some embodiments, the iron chelator is sequentially, simultaneously, or separately administered with at least one additional therapeutic agent.

In another aspect, the present disclosure provides a method for selecting a subject diagnosed with or suffering from Kufs disease for treatment with an iron chelator comprising: (a) detecting the presence of a dominant negative CSPα mutation in a test sample obtained from the subject; and (b) administering to the subject a therapeutically effective amount of an iron chelator. Kufs disease may be Type A Kufs disease or Type B Kufs disease. In some embodiments, the dominant negative CSPα mutation is $CSP\alpha^{L115R}$ or $CSP\alpha^{L116\Delta}$. In certain embodiments of the methods disclosed herein, the dominant negative CSPα mutation is detected via RT-PCR, Northern Blotting, RNA-Seq, microarray analysis, High-performance liquid chromatography (HPLC), fluorescence in situ hybridization (FISH), or massively parallel sequencing. Additionally or alternatively, in some embodiments of the methods disclosed herein, the test sample comprises tissue or a biological fluid. Examples of iron chelators include, but are not limited to, deferoxamine, desferrithiocin, deferiprone, deferasirox, Apo6619, VK28, pyridoxal isonicotinoyl hydrazone, dexrazoxane, triapine, clioquinol, tachpyr, O-trensox, flavan-3-ol, curcumin, apocynin, kolaviron, floranol, baicalein, baicalin, di-2-pyridylketone thiosemicarbazone, ligustrazine, quercetin, epigallocatechin gallate, theaflavin, phytic acid, genistein, dimercaptosuccinic acid, 2,3-dimercapto-1-propanesulfonic acid (DMPS), alpha lipoic acid (ALA), or any pharmaceutically acceptable salts thereof.

Also provided herein are kits comprising an iron chelator and instructions for using the iron chelator to treat Kufs disease in a subject in need thereof. In certain embodiments, the kits of the present technology further comprise a means for detecting the presence of a dominant negative CSPα mutation in the subject.

BRIEF DESCRIPTION OF THE DRAWINGS

FIG. 1A is a photograph of vials containing purified $CSP\alpha^{WT}$ (Wild-type CSPα), $CSP\alpha^{L115R}$ (CSPα mutant in which Leucine 115 residue is substituted with Arginine), $CSP\alpha^{L116\Delta}$ (CSPα deletion mutant), and SSPα (SSPα mutant having thirteen cysteine residues of the Cys-string substituted by serine) recombinant proteins. $CSP\alpha^{WT}$, $CSP\alpha^{L115R}$ and $CSP\alpha^{L116\Delta}$ proteins exhibit an amber-brown color, and SSPα protein is colorless. FIG. 1B shows detection of Fe in purified $CSP\alpha^{WT}$, $CSP\alpha^{L115R}$, $CSP\alpha^{L116\Delta}$, and SSPα recombinant protein solutions by X-ray fluorescence. Data are from a representative synchrotron measurement from n=3. FIG. 1C shows UV-Vis absorbance spectra of purified $CSP\alpha^{WT}$, $CSP\alpha^{L115R}$, $CSP\alpha^{L116\Delta}$ and SSPα. Representative measurement from n=4 shown. FIG. 1D shows $Fe^{3+/2+}$ ion content of purified $CSP\alpha^{WT}$, $CSP\alpha^{L115R}$, $CSP\alpha^{L116\Delta}$, and SSPα recombinant proteins measured by ferrozine colorimetry (left panel) and $S^{2-}$ content of purified $CSP\alpha^{WT}$, $CSP\alpha^{L115R}$, $CSP\alpha^{L116\Delta}$ and SSPα recombinant proteins measured by methylene blue colorimetry (right panel). Representative measurement from n=3 shown. FIG. 1E shows oligomerization of purified $CSP\alpha^{WT}$, $CSP\alpha^{L115R}$, $CSP\alpha^{L116\Delta}$, and SSPα recombinant proteins measured by sodium dodecyl sulfate polyacrylamide gel electrophoresis (SDS-PAGE) separation, and quantitative immunoblotting using anti-CSPα antibody (left panel). FIG. 1E also shows percentage of total protein detected in corresponding lane (right panel). Representative measurement from n=6 shown. A representative immunoblot is shown. Key: Mono=monomer; Dim=dimer; Oligo=oligomers of higher mass than dimer. Representative measurement from n=6 shown. Data represent means±SEM. FIG. 1F shows UV-Vis absorbance spectra of recombinant, Myc-tagged $CSP\alpha^{WT}$, $CSP\alpha^{L115R}$, $CSP\alpha^{L116\Delta}$, and SSPα proteins expressed in HEK293T cells. The recombinant, Myc-tagged proteins were immunoprecipitated from HEK293T cells using anti-Myc antibody, and eluted by trypsinization. Representative measurement from n=3 shown. FIG. 1G (left panel) shows $Fe^{3+/2+}$ ion content, as measured by ferrozine colorimetry, of Myc-tagged $CSP\alpha^{WT}$, $CSP\alpha^{L115R}$, $CS^{L116\Delta}$, and SSPα proteins expressed in HEK293T cells. The indicated protein immunoprecipitated, eluted and subjected to ferrozine colorimetry. Representative measurement from n=4 shown. Data represent means±SEM. FIG. 1G (right panel) shows $S^{2-}$ content measured by methylene blue colorimetry of Myc-tagged $CSP\alpha^{WT}$, $CSP\alpha^{L115R}$, $CSP\alpha^{L116\Delta}$, and SSPα proteins expressed in HEK293T cells. The indicated protein immunoprecipitated, eluted and subjected to methylene blue colorimetry. Representative measurement from n=4 shown. Data represent means±SEM. FIG. 1H (left panel) shows an oligomerization of CSPα variants expressed in HEK293T cells. $CSP\alpha^{WT}$, $CSP\alpha^{L115R}$, $CSP\alpha^{L116\Delta}$, and SSPα recombinant proteins were separated by SDS-PAGE, and resultant gels were subjected to quantitative immunoblotting using anti-CSPα antibody. A representative immunoblot is shown. Key: Control=empty plasmid; Mono=monomer; Dim=dimer; Oligo=oligomers of higher mass than dimer; Palm=palmitoylated. FIG. 1H (right panel) shows quantitation of oligomerized protein as a percentage of the total protein detected in corresponding lane from the immunoblots. Representative measurement from n=6 shown. In FIGS. 1D-1E, 1G-1H, data represent means±SEM. Data represent means SEM. N.D.=not detected. *P<0.05; P<0.01; *P<0.001; ****P<0.0001 by two-tailed Student's t-test. #P<0.05 by Mann-Whitney-Wilcoxon U test.

FIG. 2A shows UV-Vis absorbance spectra of purified recombinant $CSP\alpha^{WT}$, $CSP\alpha^{L115R}$, $CSP\alpha^{L116\Delta}$ and SSPα proteins following 0.1 N HCl treatment for 10 min at room temperature. FIG. 2B (left panel) shows measurement of oligomers of purified recombinant $CSP\alpha^{WT}$, $CSP\alpha^{L115R}$ and $CSP\alpha^{L116\Delta}$ proteins. Purified recombinant $CSP\alpha^{WT}$, $CSP\alpha^{L115R}$ $CSP\alpha^{L116\Delta}$, and SSPα proteins were incubated with either 1 mM L-cysteine for 2 h at room temperature (+L-Cys) or 0.1 N HCl for 20 min at room temperature (+HCl). The proteins were separated by SDS-PAGE, and resultant gels were subjected to immunoblotting using anti-CSPα antibody. A representative immunoblot is shown. Key: Mono=monomer; Oligo=oligomers of higher mass than dimer. Mono=monomer; Oligo=oligomers; grey arrowheads=possible dimer and tetramer. FIG. 2B (right panel) shows quantitation of oligomerized protein as a percentage of total protein in corresponding lane. FIG. 2C (left panel) shows resistance of oligomers to limited proteolysis in native conditions of recombinant $CSP\alpha^{WT}$, $CSP\alpha^{L115R}$, $CSP\alpha^{L116\Delta}$, and SSPα proteins. The proteins were subjected to increasing trypsin concentrations (0, 0.01, 0.05, 0.1, and 1.0 mg/ml) for 20 min at 4° C., followed by immediate inhibition of trypsin with addition of phenylmethylsulfonyl fluoride (PMSF) to 1 mM. After proteolysis was stopped, CSPα oligomers were disrupted with 0.1 N HCl for 20 min at room temperature, followed by 10 min of boiling in Laemmli sample buffer. The resultant proteins were separated by SDS-PAGE, and subjected to immunoblotting using anti-CSPα antibody. FIG. 2C (right panel) shows quantitation of remaining protein from the immunoblots as a function of trypsin concentration used in corresponding lane. FIG. 2D (left panel) shows sensitivity to limited proteolysis of acid-treated recombinant CSPα$^{WT}$, CSPα$^{L115R}$, CSPα$^{L116\Delta}$, and SSPα proteins. The proteins were first incubated with 0.1 N HCl for 20 min at room temperature and then neutralized with 1 M sodium cacodylate to pH 7.0. Limited proteolysis was then performed using increasing trypsin concentrations (0, 0.01, 0.05, 0.1, and 1.0 mg/ml) for 20 min at 4° C. Trypsin was inhibited with the addition of PMSF to 1 mM. After proteolysis was stopped, the CSPα oligomers were separated by SDS-PAGE, and subjected to immunoblotting using anti-CSPα antibody. FIG. 2D (right panel) shows quantitation of remaining protein from the immunoblots as a function of trypsin concentration used in corresponding lane. Representative measurement from n=6 shown. FIG. 2E (left panel) shows palmitoylation of Myc-tagged proteins expressed in HEK293T cells. HEK293T cells transfected with CSPα$^{WT}$, CSPα$^{L115R}$, CSPα$^{L116\Delta}$, or SSPα expressing vectors, were lysed at 48 h post-transfection, in 0.1 N HCl containing 0.1% Triton X-100 for 20 min at 4° C., to disrupt any oligomerization mediated by Fe—S clusters. Lysate was neutralized with 1 M sodium cacodylate to pH 7.0 and treated for 16 h with either 0.5 M Tris (-) or with 0.5 M hydroxylamine (HA) at 4° C. Samples were then separated by SDS-PAGE, and subjected to immunoblotting using anti-CSPα antibody. FIG. 2E (right panel) shows quantitation of palmitoylated protein as a percentage of total protein in corresponding lane. Representative measurement from n=3 shown. FIG. 2F shows UV-Vis absorbance spectra of immunoprecipitated Myc-tagged CSPα$^{WT}$, CSPα$^{L115R}$, CSPα$^{L116\Delta}$ and SSPα expressed in HEK293T cells after 0.1 N HCl treatment for 10 min at room temperature. Data are from FIG. 2A representative measurement from n=3, FIG. 2B n=4 (L-Cys) and n=9 (HCl), FIGS. 2C-2D n=6, FIG. 2E n=3, FIG. 2F representative spectra from n=3. In FIG. 2B and FIG. 2E data represent means SEM. *P<0.001; P<0.0001 by two-tailed Student's t-test. In FIGS. 2C-2D data represent means±SEM. P<0.01; ****P<0.0001 by two-way ANOVA of data excluding 1 mg/ml [trypsin]; P<; 0.05 by Tukey's multiple comparisons test.

FIG. 3A shows consecutively from left to right immunofluorescence microscopy images of cells infected with empty lentivirus (Control), lentivirus expressing Myc-tagged CSPα$^{WT}$, CSPα$^{L115R}$, or CSPα$^{L116\Delta}$. The lentivirus infected cells were stained using antibodies against Myc (green), somatodendritic marker MAP2 (red), and counterstained with nuclear stain DAPI (blue). FIG. 3B (left panel) shows interaction of CSPα variants with SNAP-25 measured via co-immunoprecipitation (co-IP) assay. Immunoprecipitation (IP) for SNAP-25 was followed by quantitative immunoblotting of the co-immunoprecipitated (co-IP'd) CSPα (top blot), and normalized to the IP'd SNAP-25 (bottom blot). IP: Control=sham IP without IgG. Palm=palmitoylated. FIG. 3B (right panel) shows quantitation of co-immunoprecipitated CSPα with anti-SNAP-25 antibody in corresponding lane. The mutant CSPα signal was normalized to the amount of immunoprecipitated wilt type CSPα. N.D.=not detected. Representative data from of n=4 shown. FIG. 3C (left panel) shows the effect of CSPα ANCL mutations on synaptic SNARE-complex assembly measured by co-immunoprecipitation (co-IP) assay. Immunoprecipitation using anti-synaptobrevin-2 (Syb-2) antibody was followed by quantitative immunoblotting of co-IP'd SNARE-complex partners syntaxin-1 (Synt-1) and SNAP-25. IP: Control=sham IP with plain rabbit serum. FIG. 3C (middle panel) shows quantitation of co-immunoprecipitated Synt-1 with anti-Syb-2 antibody in corresponding lane. The Synt-1 signal was normalized to the amount of each normalized to the IP'd Syb-2. Representative data from of n=4 shown. FIG. 3C (right panel) shows quantitation of co-immunoprecipitated SNAP-25 with anti-Syb-2 antibody in corresponding lane. The SNAP-25 signal was normalized to the amount of each normalized to the IP'd Syb-2. For the experiments shown in FIGS. 3D-3E, CSPα$^{-/-}$ primary cortical neurons were lentivirally infected to express Myc-tagged CSPα$^{WT}$, CSPα$^{L115R}$, CSPα$^{L116\Delta}$, SSPα, or empty lentivirus (Control) on 5 DIV, and were treated on 12 DIV with vehicle (-=0.1% DMSO), or iron chelators deferiprone (L1=200 μM) and deferoxamine (Dfx=200 μM) for 72 h. FIG. 3D (left panel) shows the effect of iron chelators L1 and Dfx on oligomerization of CSPα ANCL mutants. Cell extracts were separated by SDS-PAGE, and subjected to quantitative immunoblotting using anti-SNAP-25 antibody and β-actin for normalization. To measure palmitoylation, oligomers were disrupted by lysing neurons in 0.1 N HCl plus 0.1% Triton X-100 for 20 min at 4° C., followed by SDS-PAGE and quantitative immunoblotting against CSPα. Representative immunoblots are shown. Palm=palmitoylated; Dim=dimer; Oligo=oligomers of higher mass than dimer. FIG. 3D (right panel) show quantitation of oligomers, palmitoylated CSPα, respectively, in corresponding lane and expressed as a percentage of total. FIG. 3E (top panel) shows the effect of iron chelators L1 and Dfx on synaptic SNARE-complex assembly as measured by IP and quantitative immunoblotting. Cell extracts were immunoprecipitated using a negative control or anti-Syb-2 antibody, followed by quantitative immunoblotting of the co-IP'd t-SNAREs SNAP-25 and Synt-1. IP: Control=sham IP with plain rabbit serum. FIG. 3E (bottom panel) shows quantitation of SNAP-25 and Synt-1 in corresponding lanes expressed as a percentage of wild-type, each normalized to the IP'd Syb-2. Data are from FIG. 3A representative of n=3, FIG. 3B n=4, FIG. 3C n=4, FIG. 3D n=5 for CSPα oligomerization and palmitoylation, and n=10 for SNAP-25, and FIG. 3E n=3. In FIGS. 3B-3E data represent means±SEM. *P<0.05; P<0.01; *P<0.001; ****P<0.0001 by two-tailed Student's t-test. #P<0.05 by Mann-Whitney-Wilcoxon U test. n.s.=not significant; n.d.=not detected.

FIGS. 4A-4B show that ANCL mutations lead to reduced palmitoylation in CSPα and reduced levels of its client SNAP-25 in neurons. Primary cortical neurons from neonatal CSPα$^{-/-}$ mice were lentivirally infected with Myc-tagged CSPα$^{WT}$, CSPα$^{L115R}$, CSPα$^{L116\Delta}$, SSPα, or empty virus (control) on 7 days in vitro (DIV). FIG. 4A (left panel) shows levels of CSPα oligomerization, palmitoylation, and SNAP-25. Neurons were lysed on 17 DIV and CSPα oligomerization, palmitoylation, and SNAP-25 levels were measured by quantitative immunoblotting. Mono=monomer; Dim=dimer; Oligo=oligomers; Palm=palmitoylated. FIG. 4A (right panel) shows quantitation of levels of CSPα oligomerization, palmitoylation, and SNAP-25. CSPα oligomer are percent of total (left panel). CSPα palmitoylation are percent of monomers (middle panel). SNAP-25 was normalized to β-actin and is shown as percent of its expression in CSPα$^{WT}$ expressing neurons (left panel). FIG. 4B (left panel) shows levels of CSPα palmitoylation in HCl-treated neuronal cell-free extracts. Neurons were lysed on 15 DIV in 0.1 N HCl containing 0.1% Triton X-100 for 20 min at 4° C., to disrupt any oligomerization mediated by Fe—S clusters. Lysate was neutralized with 1 M sodium cacodylate to pH 7.0 and treated for 16 h with either 0.5 M Tris (-) or with 0.5 M hydroxylamine (HA) at 4° C., followed by quantitative immunoblotting against CSPα. Depalmitoylation (HA) illustrates palmitoylation-dependent mass shift. Palm=palmitoylated. FIG. 4B (right panel) shows quantitation of levels of CSPα palmitoylation in HCl-treated neuronal cell-free extracts. Data shown are from FIG. 4A n=6 for CSPα oligomerization), n=9 for CSPα palmitoylation, and n=13 for SNAP-25 levels; FIG. 4B n=5. Data represent means±SEM. *P<0.001; P<0.0001 by two-tailed Student's t-test. #P<0.05 by Mann-Whitney-Wilcoxon U test. Data represent means±SEM. *P<0.001; ****P<0.0001 by two-tailed Student's t-test. #P<0.05 by Mann-Whitney-Wilcoxon U test.

FIG. 6A shows UV-Vis absorbance spectra of immunoprecipitated CSPα from Wild-type (WT) and ANCL patient fibroblasts, before (solid lines) and following (dashed lines) 0.1 N HCl incubation for 20 min at room temperature (dashed lines). FIG. 6B shows a time course of direct induction of WT and ANCL fibroblasts into iNs using BAM+ND1 expression. Immunoblots show the expression of neuronal marker MAP-2 (right panel) and synaptic SNARE SNAP-25, as well as that of CSPα (left panel) and its chaperone complex partners Hsc70 and SGT ((right panel). Anti-MAP2 immunofluorescence following 21 d of induction (right, bottom panels). Dox=doxycycline; scale bar=50 µm. FIG. 6C (left panel) shows CSPα oligomerization, palmitoylation and SNAP-25 levels were measured in WT and ANCL iNs by quantitative immunoblotting. FIG. 6C (right panel) show quantitation of levels of CSPα oligomerization (percent of total), palmitoylation (percent of monomers), and SNAP-25 (percent of WT). FIG. 6D (left panel) shows interaction of CSPα SNAP-25 was measured in WT and ANCL iNs by immunoprecipitating SNAP-25 followed by quantitative immunoblotting of co-immunoprecipitated CSPα. Cont.=control sham IP without IgG. FIG. 6D (right panel) shows quantitation of levels of co-immunoprecipitated CSPα normalized to the immunoprecipitated SNAP-25. FIG. 6E (top panel) shows turnover of SNAP-25 as determined in WT and ANCL iNs by cycloheximide (CHX) chase followed by quantitative immunoblotting. FIG. 6E (bottom panel) shows quantitation of levels of remaining SNAP-25 in the corresponding lane plotted as a function of time. The difference between WT and ANCL **P<0.01 by two-way anova #p<0.05 by Bonferroni. For the experiments shown in FIGS. 6F-6H, WT and ANCL iNs were analyzed at 56 days following BAM+ND1 induction protocol. FIG. 6F shows lipofuscin autofluorescence at Ex 465-495, Em 515-555 nm range (bar=50 µm). FIG. 6G (left panel) shows total levels of ATP5G accumulation by quantitative immunoblotting (VDAC1 and TIM23 indicate overall mitochondrial protein expression). FIG. 6G (right panel) shows quantitation of levels of ATP5G and VDAC1 normalized to the levels of the corresponding protein in WT cells. FIG. 6H shows lipofuscin accumulation by ELISA. Data are from FIG. 6A representative of n=3; FIG. 6B representative of n=3; FIG. 6C n=4; FIG. 6D n=4; FIG. 6E n=6 for WT and n=5 for ANCL; FIG. 6F representative of n=3; FIG. 6G n=4 FIG. 6H n=4. In FIGS. 6C-6D and FIGS. 6G-6H, *P<0.05; P<0.01; *P<0.001; **P<0.0001 by two-tailed Student's t-test; #P<0.05 by Mann-Whitney-Wilcoxon U test. In FIG. 6E P<0.01 by two-way ANOVA; #P<0.05 by Tukey's multiple comparisons test.

FIG. 7A shows UV-Vis absorbance spectra. ANCL patient-derived fibroblasts were treated with 200 µM of L1 or Dfx, or vehicle (0.1% DMSO=Control) for 72 h, before measuring the UV-Vis absorbance spectra of immunoprecipitated CSPα eluted by trypsinization (solid lines). Spectra were re-read after 10 min of 0.1 N HCl treatment (dashed lines). The experiments shown in FIGS. 7B-7I, were conducted using ANCL fibroblasts converted to iNs using BAM+ND1 technique. FIG. 7B (left panel) shows the levels of oligomerized and fully palmitoylated CSPα as well as total SNAP-25 in ANCL iNs treated with L1, Dfx, or vehicle for 72 h following the iN conversion. Quantitative immunoblotting was used to measure levels of oligomerized and fully palmitoylated CSPα as well as total SNAP-25. Oligo=oligomers; Palm=palmitoylated. FIG. 7B (right panel) shows quantitation of levels of oligomerized CSPα, fully palmitoylated CSPα, and total SNAP-25. FIG. 7C (left panel) shows interaction of CSPα with SNAP-25 in ANCL iNs that were treated as in FIG. 7B. The interaction of CSPα with SNAP-25 in ANCL iNs was measured by immunoprecipitating SNAP-25 followed by quantitative immunoblotting of co-immunoprecipitated CSPα (normalized to SNAP-25 IP). Note that mainly CSPα monomers and not oligomers were detected bound to SNAP-25. Control=control sham IP without IgG. FIG. 7C (right panel) shows quantitation of levels of CSPα co-immunoprecipitated by anti-SNAP-25antibody, normalized with control iNs. FIG. 7D (top panel) shows turnover of SNAP-25 in ANCL iNs that were treated as in FIG. 7B. Turnover of SNAP-25 was determined by cycloheximide chase, while maintaining the iron-chelators or vehicle in the medium. FIG. 7D (right panel) shows quantitation of levels of remaining SNAP-25 plotted as a function of time. In the experiments shown in FIGS. 7E-7G, ANCL iNs treated with L1, Dfx, or vehicle for 56 d and analyzed. FIG. 7E shows lipofuscin autofluorescence at Ex 465-495, Em 515-555 nm (bar=50 µm). FIG. 7F (left panel) shows total levels of ATP5G accumulation by quantitative immunoblotting (VDAC1 and TIM23 indicate overall mitochondrial protein expression). FIG. 7F (right panel) shows quantitation of ATP5G as a percentage of control in corresponding lanes. FIG. 7G shows lipofuscin accumulation. The levels of lipofuscin were determined by ELISA. In the experiments shown in FIGS. 7H-7I 56 day old untreated ANCL iNs were treated with L1, Dfx, or vehicle, and analyzed. FIG. 7H (top panel) shows ATP5G levels by quantitative immunoblotting. FIG. 7H (bottom panel) shows quantitation of ATP5G in corresponding lanes expressed plotted as a function of time. FIG. 7I shows levels lipofuscin as determined by ELISA, at 0, 7, 14, and 21 d of treatment. Data are from FIG. 7A representative of n=4, FIG. 7B n=4, FIG. 7C n=4, FIG. 7D n=7, FIG. 7F n=4, FIG. 7G n=4, FIG. 7H n=6, FIG. 7I n=3. In FIGS. 7B-7C and FIGS. 7F-7G *P<0.05; P<0.01; P<0.0001 by two-tailed Student's t-test. #P<0.05 by Mann-Whitney-Wilcoxon U test. In FIG. 7D-7C and FIGS. 7H-7I P<0.01; *P<0.001; **P<0.0001 by two-way ANOVA; ##P<0.01; ###P<0.001; ####P<0.0001 by Tukey's multiple comparisons test.

DETAILED DESCRIPTION

Figure 1A:
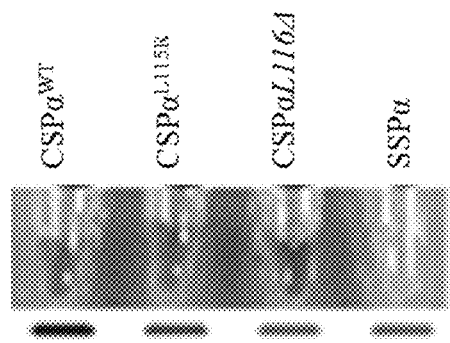
FIGS. 1A-1H show Fe—S cluster binding and oligomerization of wild-type and mutant CSPα proteins in vitro and in mammalian cells.

It is to be appreciated that certain aspects, modes, embodiments, variations and features of the present methods are described below in various levels of detail in order to provide a substantial understanding of the present technology.

In practicing the present methods, many conventional techniques in molecular biology, protein biochemistry, cell biology, immunology, microbiology and recombinant DNA are used. See, e.g., Sambrook and Russell eds. (2001) *Molecular Cloning: A Laboratory Manual,* 3rd edition; the series Ausubel et al. eds. (2007) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique,* 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology*. Methods to detect and measure levels of polypeptide gene expression products (i.e., gene translation level) are well-known in the art and include the use of polypeptide detection methods such as antibody detection and quantification techniques. (See also, Strachan & Read, *Human Molecular Genetics*, Second Edition. (John Wiley and Sons, Inc., NY, 1999)).

The present disclosure is based, in part, on the discovery that dominantly inherited adult-onset neuronal ceroid lipofuscinosis (ANCL) is caused by aggregation/oligomerization of CSPα via ectopic iron-sulfur (Fe—S) cluster-binding, which is rescued by iron-chelators. Accordingly, provided herein are methods for treating or preventing a disease associated with ectopic iron-sulfur (Fe—S) cluster formation, or a disease associated with ectopic binding of one or more proteins to iron-sulfur (Fe—S) cluster in a subject in need thereof, comprising administering to the subject a therapeutically effective amount of an iron chelator. Without wishing to be bound by any particular theory, the disease associated with ectopic iron-sulfur (Fe—S) cluster formation, or the disease associated with ectopic binding of one or more proteins to iron-sulfur (Fe—S) cluster may occur because of a genetic condition, exposure to harmful chemicals, an infectious disease or metabolic disease, or aging. In some embodiments, the disease associated with ectopic iron-sulfur (Fe—S) cluster formation, or the disease associated with ectopic binding of one or more proteins to iron-sulfur (Fe—S) cluster is caused by a mutation in a gene encoding a protein having one or more reactive thiol groups which undergoes one or more post-translational modifications, wherein the mutation decreases the level of the one or more post-translational modifications, thereby promoting formation of an ectopic iron-sulfur (Fe—S) cluster via the one or more reactive thiol groups. In some embodiments, the disease associated with ectopic iron-sulfur (Fe—S) cluster formation, or the disease associated with ectopic binding of one or more proteins to iron-sulfur (Fe—S) cluster is caused by a mutation in a gene encoding an S-palmitoylated protein, wherein the mutation reduces the level of S-palmitoylation, thereby promoting formation of an ectopic iron-sulfur (Fe—S) cluster via the one or more reactive thiol group. Some non-limiting examples of a disease associated with ectopic iron-sulfur (Fe—S) cluster formation, or ectopic binding of one or more proteins to iron-sulfur (Fe—S) cluster include Huntington's disease and adult-onset neuronal ceroid lipofuscinosis (ANCL or Kufs disease).

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent or drug to a subject includes any route of introducing or delivering to a subject a compound to perform its intended function. Administration can be carried out by any suitable route, including but not limited to, orally, intranasally, parenterally (intravenously, intramuscularly, intraperitoneally, or subcutaneously), rectally, intrathecally, or topically. Administration includes self-administration and the administration by another.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a compound or composition known to exhibit the desired therapeutic effect) and a negative control (a subject or a sample that does not receive the therapy or receives a placebo) are typically employed.

As used herein, the term "effective amount" refers to a quantity sufficient to achieve a desired therapeutic and/or prophylactic effect, e.g., an amount which results in the prevention of, or a decrease in a disease or condition described herein or one or more signs or symptoms associated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compositions may be administered to a subject having one or more signs or symptoms of a disease or condition described herein. As used herein, a "therapeutically effective amount" of a composition refers to composition levels in which the physiological effects of a disease or condition are ameliorated or eliminated. A therapeutically effective amount can be given in one or more administrations.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the term "gene" means a segment of DNA that contains all the information for the regulated biosynthesis of an RNA product, including promoters, exons, introns, and other untranslated regions that control expression.

As used herein, the terms "individual", "patient", or "subject" can be an individual organism, a vertebrate, a mammal, or a human. In some embodiments, the individual, patient or subject is a human.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration. Pharmaceutically-acceptable carriers and their formulations are known to one skilled in the art and are described, for example, in Remington's Pharmaceutical Sciences ($20^{th}$ edition, ed. A. Gennaro, 2000, Lippincott, Williams & Wilkins, Philadelphia, Pa.). Examples of pharmaceutically-acceptable carriers include a liquid or solid filler, diluent, excipient, manufacturing aid (e.g., lubricant, talc magnesium, calcium or zinc stearate, or steric acid), or solvent encapsulating material, useful for introducing the active agent into the body.

As used herein, "prevention," "prevent," or "preventing" of a disorder or condition refers to one or more compounds that, in a statistical sample, reduces the occurrence of the disorder or condition in the treated sample relative to an untreated control sample, or delays the onset of one or more symptoms of the disorder or condition relative to the untreated control sample. As used herein, prevention includes preventing or delaying the initiation of symptoms of the disease or condition. As used herein, prevention also includes preventing a recurrence of one or more signs or symptoms of a disease or condition.

As used herein, the term "separate" therapeutic use refers to an administration of at least two active ingredients at the same time or at substantially the same time by different routes.

As used herein, the term "sample" or "test sample" refers to clinical samples obtained from a subject. Biological samples may include tissues, cells, protein or membrane extracts of cells, mucus, sputum, bone marrow, bronchial alveolar lavage (BAL), bronchial wash (BW), tissue biopsies, and biological fluids (e.g., ascites fluid or cerebrospinal fluid (CSF)) isolated from a subject, as well as tissues, cells and fluids (blood, plasma, saliva, urine, serum etc.) present within a subject.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "simultaneous" therapeutic use refers to the administration of at least two active ingredients by the same route and at the same time or at substantially the same time.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, treatment means that the symptoms associated with the disease are, e.g., alleviated, reduced, cured, or placed in a state of remission.

It is also to be appreciated that the various modes of treatment of disorders as described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition.

Adult-Onset Neuronal Ceroid Lipofuscinosis (ANCL or Kufs Disease)

Neuronal ceroid lipofuscinoses (NCLs) refer to a group of storage diseases presenting from infancy to adulthood. The stored material is largely made up of subunit c of mitochondrial adenosine triphosphate synthase or saposin proteins A and D—i.e., of proteins so hydrophobic that they require special mechanisms for their breakdown and disposal. Adult-onset NCL (ANCL) is difficult to diagnose. Childhood NCLs have well-characterized clinical patterns typically involving brain and eye, abundant storage in readily accessible peripheral tissues such as skin, and largely solved molecular genetic causes. In contrast, ANCL can present in a variety of ways with progressive myoclonus epilepsy, dementia, or motor disorders and shows limited storage in peripheral tissue. Stored material is usually only found in a subset of neurons, with the accumulation of age-related lipofuscin often confused with pathologic storage. Furthermore, molecular genetic characterization of ANCL is at an early stage. Hindered by the small number of cases, and the clinical and pathologic challenges, ANCL is poorly understood. Berkovic, S F, et al., *Neurology* 87: 579-84 (2016).

Kufs disease is the best-known form of ANCL; it differs from most childhood-onset forms because there is no retinal involvement, and the inheritance can be either recessive or dominant. It is widely accepted that the uncommon teenage-onset cases without retinal involvement are grouped with adult-onset cases. The clinical presentation is variable with 2 broad forms identified. Kufs type A presents with progressive myoclonus epilepsy, whereas Kufs type B presents with dementia and motor signs. Recessive mutations in CLN6 and dominant mutations in DNAJC5 can cause Kufs type A; Kufs type B can be caused by recessive mutations in CTSF. Rare cases of ANCL with retinal involvement are attributed to mutations in PPT1 (CLN1), CLN5, and GRN. Some patients with CLN3 mutations present with neurologic manifestations in adult life, on a background of visual failure in childhood. Berkovic, S F, et al., *Neurology* 87: 579-84 (2016).

Iron Chelators

Examples of iron chelators useful in the methods disclosed herein include deferoxamine, desferrithiocin, deferiprone, deferasirox, Apo6619, VK28, pyridoxal isonicotinoyl hydrazone, dexrazoxane, triapine, clioquinol, tachpyr, O-trensox, flavan-3-ol, curcumin, apocynin, kolaviron, floranol, baicalein, baicalin, di-2-pyridylketone thiosemicarbazone, ligustrazine, quercetin, epigallocatechin gallate, theaflavin, phytic acid, genistein, dimercaptosuccinic acid, 2,3-dimercapto-1-propanesulfonic acid (DMPS), alpha lipoic acid (ALA), and any pharmaceutically acceptable salts thereof. See Hatcher H C et al., *Future Med Chem.* 2009 December; 1(9):1643-70.

The term "pharmaceutically acceptable salt" means a salt prepared from a base or an acid which is acceptable for administration to a patient, such as a mammal (e.g., salts having acceptable mammalian safety for a given dosage regime). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucuronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, tosylate, mesylate and the like.

An example of the iron chelator suitable for use of the methods of the present disclosure is deferiprone (3-hydroxy-1,2-dimethyl-4(1H)-pyridone), which has the following structure:

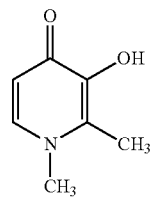

An example of the iron chelator suitable for use of the methods of the present disclosure is deferoxamine (N'-[5-(Acetyl-hydroxy-amino)pentyl]-N-[5-[3-(5-aminopentyl-hydroxy-carbamoyl) propanoylamino]pentyl]-N-hydroxy-butane diamide), which has the following structure:

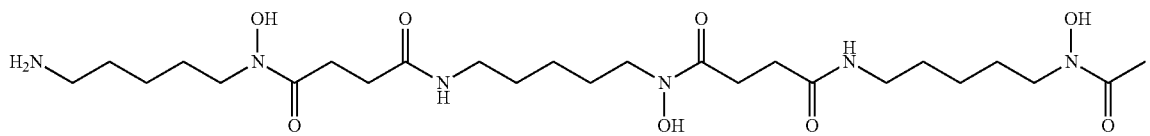 [SMILES: CC(=O)N(O)CCCCCNC(=O)CCC(=O)N(O)CCCCCNC(=O)CCC(=O)N(O)CCCCCN]

An example of the iron chelator suitable for use of the methods of the present disclosure is deferasirox ([4-[(3Z,5E)-3,5-bis(6-oxo-1-cyclohexa-2,4-dienylidene)-1,2,4-triazolidin-1-yl]benzoic acid), which has the following structure:

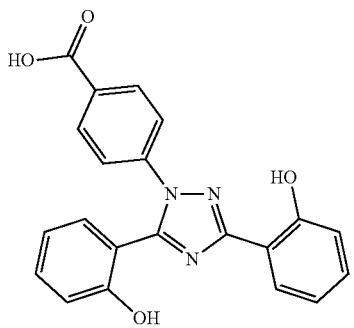 [SMILES: O=C(O)c1ccc(-n2nc(-c3ccccc3O)nc2-c2ccccc2O)cc1]

An example of the iron chelator suitable for use of the methods of the present disclosure is VK28 (VAR10100), or analog and derivative thereof. VK28 has the following structure:

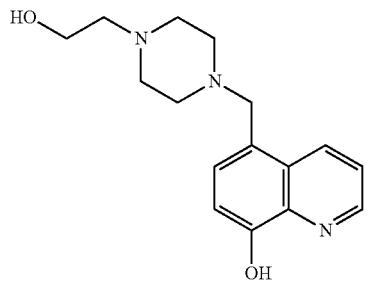 [SMILES: OCCN1CCN(Cc2ccc(O)c3ncccc23)CC1]

Other potential iron chelators for use include dimercaptosuccinic acid, 2,3-dimercapto-1-propanesulfonic acid (DMPS), alpha lipoic acid (ALA), as well as iron chelators disclosed in, for example, U.S. Pat. Nos. 6,855,711; 8,058,442, which are hereby incorporated in their entirety by reference.

Pharmaceutical Compositions

In one aspect, the present disclosure provides pharmaceutical compositions comprising iron chelators provided herein.

The pharmaceutical compositions of the present disclosure may be prepared by any of the methods known in the pharmaceutical arts. The amount of active ingredient that can be combined with a carrier material to produce a single dosage form will vary depending upon the host being treated and the particular mode of administration. The amount of active ingredient that can be combined with a carrier material to produce a single dosage form will generally be that amount of the compound that produces a therapeutic effect. Generally, the amount of active compound will be in the range of about 0.1 to 99 percent, more typically, about 5 to 70 percent, and more typically, about 10 to 30 percent.

In some embodiments, pharmaceutical compositions of the present technology may contain one or more pharmaceutically-acceptable carriers, which as used herein, generally refers to a pharmaceutically-acceptable composition, such as a liquid or solid filler, diluent, excipient, manufacturing aid (e.g., lubricant, talc magnesium, calcium or zinc stearate, or steric acid), or solvent encapsulating material, useful for introducing the active agent into the body.

Examples of suitable aqueous and non-aqueous carriers that may be employed in the pharmaceutical compositions of the present technology include, for example, water, ethanol, polyols (such as glycerol, propylene glycol, polyethylene glycol, and the like), vegetable oils (such as olive oil), and injectable organic esters (such as ethyl oleate), and suitable mixtures thereof. Proper fluidity can be maintained, for example, by the use of coating materials, such as lecithin, by the maintenance of the required particle size in the case of dispersions, and by the use of surfactants.

In some embodiments, the formulations may include one or more of sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; alginic acid; buffering agents, such as magnesium hydroxide and aluminum hydroxide; pyrogen-free water; isotonic saline; Ringer's solution; ethyl alcohol; pH buffered solutions; polyesters, polycarbonates and/or polyanhydrides; preservatives; glidants; fillers; and other non-toxic compatible substances employed in pharmaceutical formulations.

Various auxiliary agents, such as wetting agents, emulsifiers, lubricants (e.g., sodium lauryl sulfate and magnesium stearate), coloring agents, release agents, coating agents, sweetening agents, flavoring agents, preservative agents, and antioxidants can also be included in the pharmaceutical composition of the present technology. Some examples of pharmaceutically-acceptable antioxidants include: water soluble antioxidants, such as ascorbic acid, cysteine hydrochloride, sodium bisulfate, sodium metabisulfite, sodium sulfite, and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like. In some embodiments, the pharmaceutical formulation includes an excipient selected from, for example, celluloses, liposomes, micelle-forming agents (e.g., bile acids), and polymeric carriers, e.g., polyesters and polyanhydrides. Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof. Prevention of the action of microorganisms on the active compounds may be ensured by the inclusion of various antibacterial and antifungal agents, such as, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption, such as aluminum monostearate and gelatin.

Therapeutic Methods

The following discussion is presented by way of example only, and is not intended to be limiting.

One aspect of the present technology includes methods of treating a disease associated with ectopic iron-sulfur (Fe—S) cluster formation, or a disease associated with ectopic binding of one or more proteins to iron-sulfur (Fe—S) cluster. Examples of such diseases include Huntington's disease and adult-onset neuronal ceroid lipofuscinosis (ANCL or Kufs disease). Kuf disease may be Kufs disease Type A, or Kufs disease Type B. In one aspect, the present disclosure provides a method for treating a disease associated with ectopic iron-sulfur (Fe—S) cluster formation, or a disease associated with ectopic binding of one or more proteins to iron-sulfur (Fe—S) cluster in a subject in need thereof, comprising administering to the subject an effective amount of an iron chelator. In some embodiments, the iron chelator is deferoxamine, desferrithiocin, deferiprone, deferasirox, Apo6619, VK28, pyridoxal isonicotinoyl hydrazone, dexrazoxane, triapine, clioquinol, tachpyr, O-trensox, flavan-3-ol, curcumin, apocynin, kolaviron, floranol, baicalein, baicalin, di-2-pyridylketone thiosemicarbazone, ligustrazine, quercetin, epigallocatechin gallate, theaflavin, phytic acid, genistein, dimercaptosuccinic acid, 2,3-dimercapto-1-propanesulfonic acid (DMPS), alpha lipoic acid (ALA), or any pharmaceutically acceptable salts thereof. In some embodiments, the iron chelator of the present technology is sequentially, simultaneously, or separately administered with at least one additional therapeutic agent.

In some embodiments, the subject, diagnosed as having, suspected as having, or at risk of having a disease associated with ectopic iron-sulfur (Fe—S) cluster formation, or a disease associated with ectopic binding of one or more proteins to iron-sulfur (Fe—S) cluster. In some embodiments, the subject harbors a dominant negative CSPα mutation. Additionally or alternatively, in some embodiments, the dominant negative CSPα mutation is CSPα$^{L115R}$ or CSPα$^{L116\Delta}$. Additionally or alternatively, in some embodiments, the subject is diagnosed as having or is suffering from Huntington's disease or adult-onset neuronal ceroid lipofuscinosis (ANCL or Kufs disease). Kuf disease may be Kufs disease Type A, or Kufs disease Type B. In any and all embodiments of the method, the subject harbors at least one mutation in one or more genes selected from the group consisting of CLN6, DNAJC5, CTSF, PPT1 (CLN1), CLN5, GRN, and CLN3.

In therapeutic applications, compositions or medicaments comprising one or more iron chelators are administered to a subject suspected of, or already suffering from a disease or condition described herein in an amount sufficient to cure, or at least partially arrest, the symptoms of the disease, including its complications and intermediate pathological phenotypes in development of the disease.

Subjects suffering from a disease associated with ectopic iron-sulfur (Fe—S) cluster formation, or a disease associated with ectopic binding of one or more proteins to iron-sulfur (Fe—S) cluster (e.g., Huntington's disease, ANCL or Kufs disease) can be identified by any or a combination of diagnostic or prognostic assays known in the art.

In some embodiments, subjects suffering from a disease associated with ectopic iron-sulfur (Fe—S) cluster formation, or a disease associated with ectopic binding of one or more proteins to iron-sulfur (Fe—S) cluster (e.g., Huntington's disease, ANCL or Kufs disease), that are treated with one or more iron chelators disclosed herein will show amelioration or elimination of one or more of the following symptoms: progressive dementia, epilepsy, cerebellar and/or extrapyramidal symptoms, myoclonus, vision loss, seizures, ataxia, tremors and tics, dysarthria (speech difficulties), confusion, involuntary movements (e.g., tics, tremors, including those affecting the face, i.e., facial dyskinesia), and psychotic behaviour.

In one aspect, the present disclosure provides a method for selecting a subject diagnosed with or suffering from Kufs disease for treatment with an iron chelator comprising: (a) detecting the presence of a dominant negative CSPα mutation in a test sample obtained from the subject; and (b) administering to the subject a therapeutically effective amount of an iron chelator. Kufs disease may be Type A Kufs disease or Type B Kufs disease. In some embodiments, the dominant negative CSPα mutation is detected via RT-PCR, Northern Blotting, RNA-Seq, microarray analysis, High-performance liquid chromatography (HPLC), fluorescence in situ hybridization (FISH), or massively parallel sequencing. Examples of dominant negative CSPα mutations include, but are not limited to, CSPα$^{L115R}$ or CSPα$^{L116\Delta}$. Additionally or alternatively, in some embodiments of the methods disclosed herein, the test sample comprises tissue or a biological fluid. In any and all embodiments of the methods disclosed herein, the iron chelator is deferoxamine, desferrithiocin, deferiprone, deferasirox, Apo6619, VK28, pyridoxal isonicotinoyl hydrazone, dexrazoxane, triapine, clioquinol, tachpyr, O-trensox, flavan-3-ol, curcumin, apocynin, kolaviron, floranol, baicalein, baicalin, di-2-pyridylketone thiosemicarbazone, ligustrazine, quercetin, epigallocatechin gallate, theaflavin, phytic acid, genistein, dimercaptosuccinic acid, 2,3-dimercapto-1-propanesulfonic acid (DMPS), alpha lipoic acid (ALA), or any pharmaceutically acceptable salts thereof.

In one aspect, the present disclosure provides a method for monitoring the therapeutic efficacy of a pharmaceutical composition in a subject diagnosed with or suffering from a disease associated with ectopic iron-sulfur (Fe—S) cluster formation, or a disease associated with ectopic binding of one or more proteins to iron-sulfur (Fe—S) cluster comprising: (a) detecting palmitoylation levels of CSPα in a test sample obtained from the subject after the subject has been administered the pharmaceutical composition; and (b) determining that the pharmaceutical composition is effective when the palmitoylation levels of CSPα in the test sample are increased compared to that observed in a control sample obtained from the subject prior to administration of the pharmaceutical composition, wherein the pharmaceutical composition comprises an iron chelator. Additionally or alternatively, in some embodiments of the methods disclosed herein, the test sample comprises tissue or a biological fluid. In any and all embodiments of the methods disclosed herein, the iron chelator is deferoxamine, desferrithiocin, deferiprone, deferasirox, Apo6619, VK28, pyridoxal isonicotinoyl hydrazone, dexrazoxane, triapine, clioquinol, tachpyr, O-trensox, flavan-3-ol, curcumin, apocynin, kolaviron, floranol, baicalein, baicalin, di-2-pyridylketone thiosemicarbazone, ligustrazine, quercetin, epigallocatechin gallate, theaflavin, phytic acid, genistein, dimercaptosuccinic acid, 2,3-dimercapto-1-propanesulfonic acid (DMPS), alpha lipoic acid (ALA), or any pharmaceutically acceptable salts thereof.

In another aspect, the present disclosure provides a method for monitoring the therapeutic efficacy of a pharmaceutical composition in a subject diagnosed with or suffering from a disease associated with ectopic iron-sulfur (Fe—S) cluster formation, or a disease associated with ectopic binding of one or more proteins to iron-sulfur (Fe—S) cluster comprising: (a) detecting levels of CSPα oligomerization in a test sample obtained from the subject after the subject has been administered the pharmaceutical composition; and (b) determining that the pharmaceutical composition is effective when the CSPα oligomerization levels in the test sample are reduced compared to that observed in a control sample obtained from the subject prior to administration of the pharmaceutical composition, wherein the pharmaceutical composition comprises an iron chelator. Additionally or alternatively, in some embodiments of the methods disclosed herein, the test sample comprises tissue or a biological fluid. In any and all embodiments of the methods disclosed herein, the iron chelator is deferoxamine, desferrithiocin, deferiprone, deferasirox, Apo6619, VK28, pyridoxal isonicotinoyl hydrazone, dexrazoxane, triapine, clioquinol, tachpyr, O-trensox, flavan-3-ol, curcumin, apocynin, kolaviron, floranol, baicalein, baicalin, di-2-pyridylketone thiosemicarbazone, ligustrazine, quercetin, epigallocatechin gallate, theaflavin, phytic acid, genistein, dimercaptosuccinic acid, 2,3-dimercapto-1-propanesulfonic acid (DMPS), alpha lipoic acid (ALA), or any pharmaceutically acceptable salts thereof.

In another aspect, the present disclosure provides a method for monitoring the therapeutic efficacy of a pharmaceutical composition in a subject diagnosed with or suffering from a disease associated with ectopic iron-sulfur (Fe—S) cluster formation, or a disease associated with ectopic binding of one or more proteins to iron-sulfur (Fe—S) cluster comprising: (a) detecting levels of SNAP-25 or SNARE-complex assembly in a test sample obtained from the subject after the subject has been administered the pharmaceutical composition; and (b) determining that the pharmaceutical composition is effective when the levels of SNAP-25 or SNARE-complex assembly in the test sample are increased compared to that observed in a control sample obtained from the subject prior to administration of the pharmaceutical composition, wherein the pharmaceutical composition comprises an iron chelator. Additionally or alternatively, in some embodiments of the methods disclosed herein, the test sample comprises tissue or a biological fluid. In any and all embodiments of the methods disclosed herein, the iron chelator is deferoxamine, desferrithiocin, deferiprone, deferasirox, Apo6619, VK28, pyridoxal isonicotinoyl hydrazone, dexrazoxane, clioquinol, tachpyr, O-trensox, flavan-3-ol, curcumin, apocynin, kolaviron, floranol, baicalein, baicalin, di-2-pyridylketone thiosemicarbazone, ligustrazine, quercetin, epigallocatechin gallate, theaflavin, phytic acid, genistein, dimercaptosuccinic acid, 2,3-dimercapto-1-propanesulfonic acid (DMPS), alpha lipoic acid (ALA), or any pharmaceutically acceptable salts thereof.

In another aspect, the present disclosure provides a method for monitoring the therapeutic efficacy of a pharmaceutical composition in a subject diagnosed with or suffering from a disease associated with ectopic iron-sulfur (Fe—S) cluster formation, or a disease associated with ectopic binding of one or more proteins to iron-sulfur (Fe—S) cluster comprising: (a) detecting levels of Fe—S clusters in a test sample obtained from the subject after the subject has been administered the pharmaceutical composition; and (b) determining that the pharmaceutical composition is effective when the levels of Fe—S clusters in the test sample are reduced compared to that observed in a control sample obtained from the subject prior to administration of the pharmaceutical composition, wherein the pharmaceutical composition comprises an iron chelator. Additionally or alternatively, in some embodiments of the methods disclosed herein, the test sample comprises tissue or a biological fluid. In any and all embodiments of the methods disclosed herein, the iron chelator is deferoxamine, desferrithiocin, deferiprone, deferasirox, Apo6619, VK28, pyridoxal isonicotinoyl hydrazone, dexrazoxane, triapine, clioquinol, tachpyr, O-trensox, flavan-3-ol, curcumin, apocynin, kolaviron, floranol, baicalein, baicalin, di-2-pyridylketone thiosemicarbazone, ligustrazine, quercetin, epigallocatechin gallate, theaflavin, phytic acid, genistein, dimercaptosuccinic acid, 2,3-dimercapto-1-propanesulfonic acid (DMPS), alpha lipoic acid (ALA), or any pharmaceutically acceptable salts thereof.

In another aspect, the present disclosure provides a method for monitoring the therapeutic efficacy of a pharmaceutical composition in a subject diagnosed with or suffering from a disease associated with ectopic iron-sulfur (Fe—S) cluster formation, or a disease associated with ectopic binding of one or more proteins to iron-sulfur (Fe—S) cluster comprising: (a) detecting levels of lipofuscin and/or ATP5G in a test sample obtained from the subject after the subject has been administered the pharmaceutical composition; and (b) determining that the pharmaceutical composition is effective when the levels of lipofuscin and/or ATP5G in the test sample are reduced compared to that observed in a control sample obtained from the subject prior to administration of the pharmaceutical composition, wherein the pharmaceutical composition comprises an iron chelator. Additionally or alternatively, in some embodiments of the methods disclosed herein, the test sample comprises tissue or a biological fluid. In certain embodiments of the methods disclosed herein, the test sample comprises neurons or fibroblasts. In any and all embodiments of the methods disclosed herein, the iron chelator is deferoxamine, desferrithiocin, deferiprone, deferasirox, Apo6619, VK28, pyridoxal isonicotinoyl hydrazone, dexrazoxane, triapine, clioquinol, tachpyr, O-trensox, flavan-3-ol, curcumin, apocynin, kolaviron, floranol, baicalein, baicalin, di-2-pyridylketone thiosemicarbazone, ligustrazine, quercetin, epigallocatechin gallate, theaflavin, phytic acid, genistein, dimercaptosuccinic acid, 2,3-dimercapto-1-propanesulfonic acid (DMPS), alpha lipoic acid (ALA), or any pharmaceutically acceptable salts thereof.

In any and all embodiments of the methods disclosed herein, the disease associated with ectopic iron-sulfur (Fe—S) cluster formation, or the disease associated with ectopic binding of one or more proteins to iron-sulfur (Fe—S) cluster is characterized by reduced SNAP-25 proteins levels, decreased SNARE-complex assembly, or elevated levels of lipofuscin and/or mitochondrial ATP-synthase subunit C (ATP5G) in neurons. Additionally or alternatively, in some embodiments of the methods disclosed herein, the subject exhibits reduced CSPα palmitoylation in neurons and/or increased CSPα oligomerization.

Prophylactic Methods

In one aspect, the present technology provides a method for preventing or delaying the onset of a disease associated with ectopic iron-sulfur (Fe—S) cluster formation, or a disease associated with ectopic binding of one or more proteins to iron-sulfur (Fe—S) cluster, or symptoms of a disease associated with ectopic iron-sulfur (Fe—S) cluster formation, or a disease associated with ectopic binding of one or more proteins to iron-sulfur (Fe—S) cluster. Examples of such diseases include Huntington's disease and adult-onset neuronal ceroid lipofuscinosis (ANCL or Kufs disease). Kufs disease may be Type A Kufs disease or Type B Kufs disease. Also disclosed herein are methods for preventing Huntington's disease or adult-onset neuronal ceroid lipofuscinosis (ANCL or Kufs disease). In some embodiments, the subject harbors a dominant negative CSPα mutation. Additionally or alternatively, in some embodiments, the dominant negative CSPα mutation is $CSP\alpha^{L115R}$ or $CSP\alpha^{L116\Delta}$. Additionally or alternatively, the subject harbors at least one mutation in one or more genes selected from the group consisting of CLN6, DNAJC5, CTSF, PPT1 (CLN1), CLN5, GRN, and CLN3.

Subjects at risk for a disease associated with ectopic iron-sulfur (Fe—S) cluster formation, or a disease associated with ectopic binding of one or more proteins to iron-sulfur (Fe—S) cluster can be identified by, e.g., any or a combination of diagnostic or prognostic assays known in the art. For example, the subjects may exhibit at least one mutation in one or more of CLN6, DNAJC5, CTSF, PPT1 (CLN1), CLN5, GRN, and CLN3. Berkovic, S F, et al., *Neurology* 87: 579-84 (2016). Alternatively, or additionally, the subjects may have a family history of such diseases and other factors that increase the risk of such diseases.

In any and all embodiments of the methods disclosed herein, the disease associated with ectopic iron-sulfur (Fe—S) cluster formation, or the disease associated with ectopic binding of one or more proteins to iron-sulfur (Fe—S) cluster is characterized by reduced SNAP-25 proteins levels, decreased SNARE-complex assembly, or elevated levels of lipofuscin and/or mitochondrial ATP-synthase subunit C (ATP5G) in neurons. Additionally or alternatively, in some embodiments of the methods disclosed herein, the subject exhibits reduced CSPα palmitoylation in neurons and/or increased CSPα oligomerization.

In prophylactic applications, pharmaceutical compositions or medicaments comprising an iron chelator of the present technology are administered to a subject susceptible to, or otherwise at risk for developing a disease associated with ectopic iron-sulfur (Fe—S) cluster formation, or a disease associated with ectopic binding of one or more proteins to iron-sulfur (Fe—S) cluster (e.g., Huntington's disease, or ANCL or Kufs disease), in an amount sufficient to eliminate or reduce the risk, or delay the onset of the disease, including biochemical, histologic and/or behavioral symptoms of the disease, its complications and intermediate pathological phenotypes presenting during development of the disease. Administration of a prophylactic iron chelator can occur prior to the manifestation of symptoms characteristic of the disease or disorder, such that the disease or disorder is prevented or, alternatively, delayed in its progression.

In some embodiments, treatment with an iron chelator will prevent or delay the onset of one or more of the following symptoms: progressive dementia, epilepsy, cerebellar and/or extrapyramidal symptoms, myoclonus, vision loss, seizures, ataxia, tremors and tics, dysarthria (speech difficulties), confusion, involuntary movements (e.g., tics, tremors, including those affecting the face, i.e., facial dyskinesia), and psychotic behaviour.

For therapeutic and/or prophylactic applications, a composition comprising an iron chelator disclosed herein is administered to the subject. In some embodiments, the iron chelator is administered one, two, three, four, or five times per day. In some embodiments, the iron chelator is administered more than five times per day. Additionally or alternatively, in some embodiments, the iron chelator is administered every day, every other day, every third day, every fourth day, every fifth day, or every sixth day. In some embodiments, the iron chelator is administered weekly, bi-weekly, tri-weekly, or monthly. In some embodiments, the iron chelator is administered for a period of one, two, three, four, or five weeks. In some embodiments, the iron chelator is administered for six weeks or more. In some embodiments, the iron chelator is administered for twelve weeks or more. In some embodiments, the iron chelator is administered for a period of less than one year. In some embodiments, the iron chelator is administered for a period of more than one year. In some embodiments, the iron chelator is administered throughout the subject's life.

In some embodiments of the methods of the present technology, the iron chelator is administered daily for 1 week or more. In some embodiments of the methods of the present technology, the iron chelator is administered daily for 2 weeks or more. In some embodiments of the methods of the present technology, the iron chelator is administered daily for 3 weeks or more. In some embodiments of the methods of the present technology, the iron chelator is administered daily for 4 weeks or more. In some embodiments of the methods of the present technology, the iron chelator is administered daily for 6 weeks or more. In some embodiments of the methods of the present technology, the iron chelator is administered daily for 12 weeks or more. In some embodiments, the iron chelator is administered daily throughout the subject's life.

In some embodiments, the iron chelator of the present technology is sequentially, simultaneously, or separately administered with at least one additional therapeutic agent.

Determination of the Biological Effect of an Iron Chelator

In various embodiments, suitable in vitro or in vivo assays are performed to determine the effect of an iron chelator disclosed herein, and whether its administration is indicated for treatment. In various embodiments, in vitro assays can be performed with representative animal models, to determine if a given iron chelator of the present technology exerts the desired effect on reducing or eliminating signs and/or symptoms of a disease associated with ectopic iron-sulfur (Fe—S) cluster formation, or a disease associated with ectopic binding of one or more proteins to iron-sulfur (Fe—S) cluster (e.g., Huntington's disease, or ANCL or Kufs disease). Compounds for use in therapy can be tested in suitable animal model systems including, but not limited to rats, mice, chicken, cows, monkeys, rabbits, and the like, prior to testing in human subjects. Similarly, for in vivo testing, any of the animal model systems known in the art can be used prior to administration to human subjects. In some embodiments, in vitro or in vivo testing is directed to detect the levels of CSPα palmitoylation, CSPα oligomerization, SNAP-25 expression, Fe—S cluster formation, SNARE-complex assembly, neuronal lipofuscin accumulation, and/or neuronal ATP5G accumulation (See Examples 5 and 7 described herein).

Animal models of a disease associated with a disease associated with ectopic iron-sulfur (Fe—S) cluster formation, or ectopic binding of one or more proteins to iron-sulfur (Fe—S) cluster (e.g., Huntington's disease, or ANCL or Kufs disease), may be generated using techniques known in the art. Such models may be used to demonstrate the biological effect of an iron chelator disclosed herein in the prevention and treatment of a disease associated with ectopic binding of one or more proteins to iron-sulfur (Fe—S) cluster (e.g., Huntington's disease, or ANCL or Kufs disease), and for determining what comprises a therapeutically effective amount of an iron chelator in a given context.

Modes of Administration and Effective Dosages

Any method known to those in the art for contacting a cell, organ or tissue with an iron chelator disclosed herein may be employed. Suitable methods include in vitro, ex vivo, or in vivo methods. In vivo methods typically include the administration of an iron chelator of the present technology to a mammal, suitably a human. When used in vivo for therapy, iron chelators of the present technology are administered to the subject in effective amounts (i.e., amounts that have desired therapeutic effect). The dose and dosage regimen will depend upon the degree of the disease state of the subject, the characteristics of the particular agent (e.g., an iron chelator) used, e.g., its therapeutic index, and the subject's history.

The effective amount may be determined during preclinical trials and clinical trials by methods familiar to physicians and clinicians. An effective amount of an iron chelator of the present technology useful in the methods may be administered to a mammal in need thereof by any of a number of well-known methods for administering pharmaceutical compounds. An iron chelator of the present technology may be administered systemically or locally.

An iron chelator of the present technology can be incorporated into pharmaceutical compositions for administration, singly or in combination, to a subject for the treatment or prevention of a disease or condition disclosed herein. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The pharmaceutical compositions having an iron chelator disclosed herein can include a carrier, which can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be advantageous to include isotonic agents, for example, sugars, polyalcohols such as mannitol, sorbitol, or sodium chloride in the composition. Prolonged absorption of the injectable compositions can be brought about by including in the composition an agent that delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser, which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed by iontophoresis.

A therapeutic agent can be formulated in a carrier system. The carrier can be a colloidal system. The colloidal system can be a liposome, a phospholipid bilayer vehicle. In one embodiment, the therapeutic agent is encapsulated in a liposome while maintaining the agent's structural integrity. One skilled in the art would appreciate that there are a variety of methods to prepare liposomes. (See Lichtenberg, et al., *Methods Biochem. Anal.*, 33:337-462 (1988); Anselem, et al., *Liposome Technology*, CRC Press (1993)). Liposomal formulations can delay clearance and increase cellular uptake (See Reddy, *Ann. Pharmacother.*, 34(7-8): 915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the therapeutic agent can be embedded in the polymer matrix, while maintaining the agent's structural integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.*, 34(7-8):915-923 (2000)). A polymer formulation for human growth hormone (hGH) has been used in clinical trials. (See Kozarich and Rich, *Chemical Biology*, 2:548-552 (1998)).

Examples of polymer microsphere sustained release formulations are described in PCT publication WO 99/15154 (Tracy, et al.), U.S. Pat. Nos. 5,674,534 and 5,716,644 (both to Zale, et al.), PCT publication WO 96/40073 (Zale, et al.), and PCT publication WO 00/38651 (Shah, et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immunomethods*, 4(3): 201-9 (1994); and Gregoriadis, "Engineering Liposomes for Drug Delivery: Progress and Problems," *Trends Biotechnol.*, 13(12):527-37 (1995). Mizguchi, et al., *Cancer Lett.*, 100: 63-69 (1996), describes the use of fusogenic liposomes to deliver a protein to cells both in vivo and in vitro.

Dosage, toxicity and therapeutic efficacy of any therapeutic agent can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are advantageous. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may be within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to determine useful doses in humans accurately. Levels in plasma may be measured, for example, by high performance liquid chromatography.

Typically, an effective amount of an iron chelator of the present technology sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example, dosages can be 1 mg/kg body weight or 10 mg/kg body weight every day, every two days or every three days or within the range of 1-10 mg/kg every week, every two weeks or every three weeks. In one embodiment, a single dosage of the therapeutic compound ranges from 0.001-10,000 micrograms per kg body weight. In one embodiment, concentrations of an iron chelator of the present technology in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regime.

In some embodiments, a therapeutically effective amount of an iron chelator of the present technology may be defined as a concentration of the agent at the target tissue of $10^{-32}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue, such as by single daily or weekly administration, but also including continuous administration (e.g., parenteral infusion or transdermal application).

In some embodiments, the iron chelator is administered 1-10 times a day, once a day, twice, three, four, or more times a day, 1-3 times a day, 2-4 times a day, 3-6 times a day, 4-8 times a day or 5-10 times a day. In some embodiments, the iron chelator is administered every day, every other day, 2-3 times a week, or 3-6 times a week.

In some embodiments, the dose of the iron chelator can be, for example, in the range of about 0.01, 0.1, 0.5, 1, 5, 10, or 100 mg per kg of body weight per day to about 20, 50, 100, 500, or 1000 mg per kilogram of body weight. Particularly in embodiments where the active substance is administered directly at affected organ, the dosage administered can be independent of body weight, and can be in smaller amounts (e.g., 1-1000 μg per dose).

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance with the present methods can be any mammal, including, for example, farm animals, such as sheep, pigs, cows, and horses; pet animals, such as dogs and cats; laboratory animals, such as rats, mice and rabbits. In some embodiments, the mammal is a human.

Kits

The present disclosure also provides kits comprising at least one iron chelator of the present technology and instructions for using the same to prevent and/or treat a disease associated with ectopic iron-sulfur (Fe—S) cluster formation, or a disease associated with ectopic binding of one or more proteins to iron-sulfur (Fe—S) cluster (e.g., Huntington's disease, or ANCL or Kufs disease). In some embodiments, the subject harbors a dominant negative CSPα mutation, such as CSPα$^{L115R}$ or CSPα$^{L116\Delta}$. Additionally or alternatively, in some embodiments, the kits of the present technology further comprise a means for detecting the presence of a dominant negative CSPα mutation in the subject.

In some embodiments, the subject is diagnosed as having or is suffering from Huntington's disease or adult-onset neuronal ceroid lipofuscinosis (ANCL or Kufs disease). Additionally or alternatively, in some embodiments, Kufs disease is Kufs disease Type A, or Type B. The subject may harbor at least one mutation in one or more genes selected from the group consisting of CLN6, PPT1 (CLN1), DNAJC5, CTSF, CLN5, GRN, and CLN3. Optionally, the above described components of the kits of the present technology are packed in suitable containers and labeled for the prevention and/or treatment of a disease associated with ectopic iron-sulfur (Fe—S) cluster formation, or a disease associated with ectopic binding of one or more proteins to iron-sulfur (Fe—S) cluster (e.g., Huntington's disease, or ANCL or Kufs disease).

The above-mentioned components may be stored in unit or multi-dose containers, for example, sealed ampoules, vials, bottles, syringes, and test tubes, as an aqueous, preferably sterile, solution or as a lyophilized, preferably sterile, formulation for reconstitution. The kit may further comprise a second container which holds a diluent suitable for diluting the pharmaceutical composition towards a higher volume. Suitable diluents include, but are not limited to, the pharmaceutically acceptable excipient of the pharmaceutical composition and a saline solution. Furthermore, the kit may comprise instructions for diluting the pharmaceutical composition and/or instructions for administering the pharmaceutical composition, whether diluted or not. The containers may be formed from a variety of materials such as glass or plastic and may have a sterile access port (for example, the container may be an intravenous solution bag or a vial having a stopper which may be pierced by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. The kits may optionally include instructions customarily included in commercial packages of therapeutic products, that contain information about, for example, the indications, usage, dosage, manufacture, administration, contraindications and/or warnings concerning the use of such therapeutic products.

The kit can also comprise, e.g., a buffering agent, a preservative or a stabilizing agent. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit. In certain embodiments, the use of the reagents can be according to the methods of the present technology.

EXAMPLES

The present technology is further illustrated by the following Examples, which should not be construed as limiting in any way. The examples herein are provided to illustrate advantages of the present technology and to further assist a person of ordinary skill in the art with preparing or using the compositions and systems of the present technology. The examples should in no way be construed as limiting the scope of the present technology, as defined by the appended claims. The examples can include or incorporate any of the variations, aspects, or embodiments of the present technology described above. The variations, aspects, or embodiments described above may also further each include or

Example 1: Materials and Methods

Purification of Recombinant CSPα Wild-Type and Mutant Proteins

For recombinant protein expression, CSPα$^{WT}$, CSPα$^{L115R}$, CSPα$^{L116\Delta}$ and SSPα (L$^{115}$LT$\underline{SS}$Y$\underline{SSSS}$L$\underline{SSS}$FN$\underline{SSS}$GK$\underline{S}$KP$^{138}$ (SEQ ID NO: 1); underlined=C to S substitutions) were cloned into a modified pGEX-KG vector. Glutathione S-transferase (GST) was followed by a thrombin-cleavage site and a Tobacco Etch Virus (TEV) protease cleavage site, followed by the cDNA of the CSPα variant. Transformed BL21(DE3) E. coli were grown at 37° C. Protein expression was induced with 0.8 mM Isopropyl β-D-1-thiogalactopyranoside (IPTG) at OD 0.6-0.8 at 20° C. for 18 hours. Bacteria were pelleted and then lysed in phosphate buffered saline (PBS; pH 7.4) containing 2 mM dithiotheitol (DTT), 0.1 mg/ml hen egg lysozyme, 1 mM phenylmethylsulfonylfluoride (PMSF), EDTA-free protease inhibitor cocktail (Thermo Fisher Scientific, Waltham MA), and 20-25 units/ml DNase I. Cells were broken by sonication (30 pulses of 0.5 second at 50% amplitude), and insoluble material was removed by centrifugation for 30 min at 7000 average centrifugal force (gav) at 4° C. Proteins in the supernatant were affinity-purified using glutathione Sepharose resin (GE Healthcare) incubation overnight at 4° C., followed by several washes with PBS containing 1 mM DTT. Bound GST-protein was approximated by SDS-PAGE followed by Coomassie brilliant blue R-250 staining, in comparison with bovine serum albumin (BSA) standards. The GST-protein bound to resin was cleaved overnight by TEV protease at 1:300 molar ratio (protease:protein) at 4° C. The final buffer for storage at 4° C. (short-term) or −30° C. (long-term) was PBS containing 2 mM DTT, 337 mM total NaCl, 0.01% Triton X-100, supplemented with EDTA-free protease inhibitor cocktail (Thermo Fisher). Despite exposure to air throughout this procedure, CSPα$^{WT}$, CSPα$^{L115R}$, CSPα$^{L116\Delta}$ had a stable amber-brown color while SSPα was clear in solution. Protein concentrations post-TEV cleavage were estimated by: a) BSA standards compared via SDS-PAGE followed by Coomassie staining, 2) NanoDrop spectrophotometry (Abs 280 nm) using a Take3 (BioTek) plate reader, and 3) Bicinchoninic acid (BCA) assay (Thermo Scientific, Waltham MA).

Heterologous Expression of CSPα Wild-Type and Mutant Proteins in Mammalian Cells Human embryonic kidney 293T cells (HEK293T; American Type Culture Collection) were maintained in Dulbecco's Modified Eagle Medium (DMEM; Thermo Fisher Scientific) supplemented with 10% fetal bovine serum (Rocky Mountain Biologicals) and L-glutamine/penicillin/streptomycin (Thermo Fisher Scientific). Cells were transfected at ~60% confluency with pCMV5 plasmid encoding N-terminally Myc-epitope tagged CSPα$^{WT}$, CSPα$^{L115R}$, CSPα$^{L116\Delta}$ and SSPα (Myc-tag and linker sequence=MEQKLISEEDLNEFGQGAQGQL (SEQ ID NO: 2)), using calcium-phosphate precipitation method. Jordan et al., Nucleic acids research 24: 596-601 (1996). 48 h post-transfection, cells were lysed in: 1) 0.1 N HCl containing 0.1% Triton X-100 and EDTA-free protease inhibitor cocktail (Thermo Fisher), for disruption of Fe—S clusters measuring palmitoylation and for chemical depalmitoylation; or 2) PBS containing 0.1% Triton X-100, supplemented with EDTA-free protease inhibitor cocktail (Thermo Fisher) for immunoprecipitation followed by UV-Vis spectrometry and measurement of [Fe$^{2+/3+}$] and [S$^{2-}$].

Mouse Lines and Primary Neuron Culture

Primary neurons from CSPα knockout (CSPα$^{-/-}$) mice were used as a clean background for expression of CSPα wild-type and mutant proteins. This mouse line is described in Tobaben et al., Neuron 31: 987-999 (2001); and Fernindez-Chacón et al., Neuron 42: 237-251 (2004), and is available from Jackson Laboratory (B6; 129S6-Dnajc5tmlSud/J; stock #: 006392). Animal husbandry and the experimental protocols used in this study were approved by the Institutional Animal Care and Use Committee (IACUC) at Weill Cornell Medicine.

Neonates from CSPα+/− to CSPα+/− breeding pairs were genotyped before performing neuron culture from CSPα$^{-/-}$ pups. Cortical neurons were cultured essentially as described previously in Maximov et al., J Neurosci Methods 161: 75-87 (2007). Cortices were dissected in ice-cold HBSS, dissociated by trypsinization (0.05% trypsin-EDTA for 10 min at 37° C.), triturated with a siliconized pipette, and plated onto poly-L-lysine coated 24-well plastic dishes or coverslips. Plating medium (DMEM, Thermo Fisher) supplemented with 5 g/L glucose, 0.2 g/L NaHCO$_3$, 0.1 g/L transferrin, 0.25 g/L insulin, 0.3 g/L L-glutamine, and 10% fetal bovine serum was replaced with growth medium (DMEM, Thermo Fisher) containing 5 g/L glucose, 0.2 g/L NaHCO$_3$, 0.1 g/L transferrin, 0.3 g/L L-glutamine, 5% fetal bovine serum, 2% B-27 or N21-MAX supplement, and 2 μM cytosine arabinoside 2 days after plating. Cultured neurons were transduced with lentiviral particles and harvested for experiments as described in figure captions.

Lentivirus Production and Transduction

N-terminally Myc-epitope tagged CSPα$^{WT}$, CSPα$^{L115R}$, CSPα$^{L116\Delta}$ and SSPα (Myc-linker as in pCMV5 vector described above) were cloned into lentiviral FUW vector (Lois et al., Science 295: 868-872 (2002). HEK293T cells were co-transfected with the vector plasmid, the HIV-1 lentiviral packaging constructs pRSVREV and pMDLg/pRRE (Dull et al., Journal of virology 72: 8463-8471 (1998)), and the vesicular stomatitis virus-G expression plasmid pHCMVG. Yee et al., Proc Natl Acad Sci USA 91: 9564-9568 (1994). The virus-containing culture supernatant was collected 48 h post-transfection and was either added directly to medium of cells to transduce them, or was concentrated by centrifugation at 50,000 g$_{av}$ for 90 min. The viral pellet was resuspended in neuronal medium (at ⅒ of the precentrifugation volume). All lentiviruses used in a single experiment were prepared together. Neurons were infected and harvested for experiments at times described in figure captions.

X-Ray Fluorescence (XRF)

The X-ray fluorescence experiments were carried out at the F3 station of CHESS (Cornell University, Ithaca, NY). The source of the F3 beamline is the radiation from a bending magnet in the 5.3 GeV Cornell Electron Storage Ring (CESR). Monochromatic X-rays of 12 keV were used to excite the fluorescence from the samples. Ten microliters of protein solution were pipetted into a quartz capillary (1 mm inside diameter) and mounted on the goniometer. X-ray fluorescence of the sample was collected by an energy dispersive detector: Hitachi Vortex-ME4 Silicon Drift Detector (SDD).

Limited Proteolysis

Limited trypsin digestion was used to detect oligomerization in each protein's native in vitro state. Purified protein (10 mg/ml) was exposed to increasing concentration of trypsin (0.01-1 mg/ml) for 20 minutes at 4° C., followed by immediate inhibition of trypsin with addition of PMSF to 1 mM. To clarify the effect of CSPα oligomerization on trypsin-susceptibility, CSPα oligomers were disrupted, 1) before trypsinization, by incubation with 0.1 N HCl for 20 min at room temperature, and then neutralized with 1 M sodium cacodylate to pH 7.0, or 2) after limited proteolysis, with 0.1 N HCl for 20 min at room temperature. Samples were boiled for 20 minutes in Laemmli sample buffer, followed by SDS-PAGE and immunoblotting.

Immunoprecipitation of CSPα Wild-Type and Mutant Proteins from Mammalian Cells

Immunoprecipitation was used to isolate CSPα variants expressed in HEK293T cells or in CSPα$^{-/-}$ primary neurons, and to isolate the endogenously expressed CSPα in WT or ANCL fibroblasts, in order to detect Fe—S clusters by UV-Vis spectroscopy and to measure [Fe$^{2+/3+}$] and [S$^{2-}$]. Cells expressing Myc-epitope tagged CSPα variants or endogenous CSPα were lysed in PBS containing 0.1% Triton X-100 and supplemented with EDTA-free protease inhibitor cocktail (Thermo Fisher). Post-nuclear supernatant was incubated for 2 h at 4° C. with the anti-Myc monoclonal antibody or with anti-CSPα rabbit polyclonal antibody for another 1 h following the addition of protein-G Sepharose or protein-A Sepharose (GE Healthcare), respectively. Protein bound to antibody-beads was washed 5 times with lysis buffer at 4° C., and the beads were split into two portions: 1) 90% of the beads were "eluted" into 50 μl of PBS by proteolysis (0.5 mg/ml trypsin) for 20 min at room temperature, followed by trypsin-inhibition by addition of PMSF to 1 mM, and the supernatant was immediately used for UV-Vis spectroscopy or to measure [Fe$^{2+/3+}$] and [S$^{2-}$], 2) 10% of the beads were eluted in 0.1 N HCl for 10 min at room temperature (to disassemble Fe—S clusters/oligomers), followed by boiling for 10 min in Laemmli sample buffer. Where [Fe$^{2+/3+}$] and [S$^{2-}$] ions bound per protein molecule was calculated, the Myc-IP eluate was separated on SDS-PAGE and quantitatively immunoblotted alongside a known amount of recombinant SSPα using CSPα antibody, in order to estimate the protein yield from immunoprecipitation.

Analysis of SNARE-Complex Assembly in Primary Neurons

Co-immunoprecipitation (co-IP), was used to quantify SNAP-25 and Synt-1 bound to Syb-2 in primary neurons from CSPα$^{-/-}$ mice either expressing CSPα$^{WT}$, CSPα$^{L115R}$, CSPα$^{L116\Delta}$ or SSPα, or following pharmacological iron-chelation. Post-nuclear supernatant in lysis buffer (PBS containing 0.1% Triton X-100) supplemented with EDTA-free protease inhibitor cocktail (Thermo Fisher) was incubated for 2 h at 4° C. with anti-Syb-2 polyclonal antiserum, or with plain rabbit serum for sham IP. Samples were incubated at 4° C. for additional 1 h after adding protein-A Sepharose slurry (GE Healthcare), followed by 5 washes with 1 ml lysis buffer, and then elution into Laemmli sample buffer by boiling for 20 min (which also disassembles the SNARE-complexes). Co-IP'd proteins and 5% of the input lysate were separated on SDS-PAGE and quantitatively immunoblotted using Syb-2, Synt-1 and SNAP-25 monoclonal antibodies.

Determination of Interaction of CSPα with SNAP-25

Interaction between CSPα and SNAP-25 was studied by co-IP of CSPα with SNAP-25. From induced neurons (iNs) and from primary CSPα$^{-/-}$ neurons lentivirally expressing CSPα variants, either before or after pharmacological iron chelation, SNAP-25 was IP'd as described above, using SNAP-25 monoclonal antibody, or no IgG for sham IP, and protein-G sepharose (GE Healthcare. Co-IP'd proteins were eluted by boiling for 20 minutes in Laemmli sample buffer and separated on SDS-PAGE in parallel with 5% of input lysate, followed by quantitative immunoblotting using polyclonal SNAP-25 and CSPα antibodies.

Chemical Depalmitoylation

Palmitoylation of CSPα variants was assessed by chemical cleavage of Cys-palmitoyl thioester linkages with hydroxylamine. Lysates were incubated overnight at 4° C. with either 0.5 M Tris (as control), or 0.5 M hydroxylamine (from 50% w/v stock in H2O; EMID Millipore). Molecular mass-shift between palmitoylated and depalmitoylated protein was analyzed by SDS-PAGE separation followed by quantitative immunoblotting.

Fe—S Cluster Disruption with L-Cysteine and HCl

The characteristic amber color of recombinant CSPα$^{WT}$, CSPα$^{L115R}$ and CSPα$^{L116\Delta}$ was eliminated immediately by addition of an equal volume of 0.1 N HCl, indicating sensitivity of Fe—S clusters to acid treatment. For disruption of Fe—S clusters, prior to assays or neutralization with 1 M cacodylate, protein was incubated with 0.1 N HCl at room temperature for 10-20 min (as indicated in figure captions). Iron-sulfur clusters were also incubated with 1 mM L-cysteine for 2 hours at room temperature to partially disrupt Fe—S clusters.

UV-Visible Absorbance Spectrum

100 μl of protein solution (20 mg/ml purified protein or ~2 mg/ml immunoprecipitated protein) was loaded into a UV-permeant 96-well clear bottom plate (Corning). The absorbance spectra (200-600 nm) were recorded using a Synergy H1 Hybrid Reader (BioTek). For acid treatment, protein was incubated with 0.1 N HCl for 10 min at room temperature. Any precipitate was centrifuged down, and supernatant was used for recording UV-Vis absorbance as above.

Determination of Iron Content

Iron content was measured using the ferrozine colorimetric method. Tamarit et al., *Analytical biochemistry* 351: 149-151 (2006); and Riemer et al., *Analytical Biochemistry* 331: 370-375 (2004). 250 μl of 20 μM recombinant protein or ~18 μM immunoprecipitated protein (determined by immunoblotting next to recombinant protein) was incubated with 250 μl 6% HNO$_3$ at 98° C. for 16 h. The samples were centrifuged at 18,000 g$_{av}$ and the supernatant was then combined with iron-detection reagent containing sodium ascorbate (30 mM final), ferrozine (1 mM final) and ammonium acetate (300 mM final). A color change from clear to purple indicated iron ions. 180 μl of the solution were loaded into a UV-permeant 96-well clear bottom plate (Corning), and absorbance was measured at 550 nm against an FeCl$_3$ standard curve using a Synergy H1 Hybrid Reader, and normalized to the protein amount.

Determination of Inorganic Sulfur Content

Inorganic sulfur content was determined using the methylene blue colorimetric assay. Fogo and Popowsky, *Anal Chem* 21: 732-734 (1949). Briefly, 200 μl of 40 μM recombinant protein or ~16 μM immunoprecipitated protein (determined by immunoblotting next to recombinant protein) was incubated with 600 μl of 1% zinc acetate and 50 μl of 7% NaOH for 15 minutes at room temperature. The samples were centrifuged at 4200 g$_{av}$ and 150 μl of 0.1% N,N-dimethyl-p-phenylenediamine in 5 M HCl was added to the bottom of the tube, followed by addition of 150 μl of 10 mM FeCl$_3$. The samples were then centrifuged for 10 min at 18,000 gay. A color change from light pink to blue revealed methylene blue formation, indicating sulfide concentration. Sulfur content was measured by absorbance at 670 nm against a sodium sulfide standard curve using a Synergy H1 Hybrid Reader, and normalized to the protein amount.

Pharmacological Iron-Chelation

For pharmacological iron-chelation, deferiprone (L1; 200 µM; Biotang), deferoxamine mesylate (Dfx; 200 µM; Calbiochem), or 0.1% DMSO as vehicle control were added to the respective culture media of primary cortical neurons, fibroblasts, or iNs. When these media were changed, the fresh media contained identical concentration of the respective iron-chelator or vehicle.

Direct Conversion of Patient Fibroblasts to Induced Neurons

Fibroblasts from an affected 30-year-old female carrying the L116Δ mutation were obtained, and an age-and-sex matched unaffected fibroblast line was frozen, thawed and cultured in parallel to maintain similar passage numbers. Fibroblasts were maintained in DMEM supplemented with 10% fetal bovine serum supplemented with L-glutamine, penicillin, and streptomycin. For direct conversion to induced neurons, fibroblasts were transduced by concentrated lentiviral particles in order to express Ascl1, Brn2 and Myt11 and NeuroD1 (BAM+ND1) via the rtTA induction system, using doxycycline (Z. P. Pang et al., Nature 476, 220-223 (2011)). Virus containing medium was removed after 24 h and replaced with N3 medium (Wernig et al., *J Neurosci Res* 69: 918-924 (2002)) containing doxycycline (2 µg/ml). Every 3-5 days (depending on medium-acidity), half the medium was changed to fresh N3 medium with doxycycline. Time course experiments, such as cycloheximide chase and iron-chelator treatment, were performed in the N3 medium in the presence of doxycycline.

Immunofluorescence in Neurons and iNs, and Lipofuscin Fluorescence in iNs

For, immunofluorescent labeling of CSPα$^{-/-}$ cortical neurons expressing Myc-tagged CSPα variants, cells on coverslips were washed with PBS+1 mM MgCl2 and fixed in 4% paraformaldehyde for 30 min at room temperature. Cells were permeabilized for 5 min in PBS containing+0.1% Triton X-100, and blocked for 20 min in PBS+5% BSA (blocking buffer). Coverslips were then incubated in primary antibodies—mouse anti-Myc (9E10, DSHB; 1:500) and rabbit anti-Map2 (ab5622, Millipore; 1:1000) overnight at 4° C. Following 5 washes, cover slips were incubated with anti-mouse Alexa 488 and anti-rabbit Alexa 546 (Life Technologies) in blocking buffer containing DAPI, for 1-2 hours, followed by 5 PBS washes, and mounting on slides in Fluormount G (Thermo Fisher). Images were acquired on Nikon H550L microscope.

In the iNs, MAP-2 staining (m1406, Sigma; 1:250) was performed and visualized as above.

Lipofuscin fluorescence was detected in fixed iNs at Ex480 (BP30), Dm505 (LP), Em535 (BP40) using Nikon Eclipse Ts2-FL Inverted Fluorescence Microscope.

Lipofuscin ELISA iNs from each well of a 6 well dish were solubilized in 100 µl PBS with 0.1% Triton X-100 for 1 h at 4° C. Post nuclear supernatant collected by centrifugation at 1000 $g_{av}$ for 15 min was used for the assay. These samples were analyzed for lipofuscin content using human lipofuscin competitive ELISA (MyBiosource; MBS7217173). Following the colorimetric reaction, optical density at 450 nm was read from the standard and the sample wells using Synergy H1 Hybrid Reader (BioTek).

Measurement of SNAP-25 Turnover

Cycloheximide chase was performed in patient-derived induced neurons at the indicated time points at 0.1 g/L (Sigma) as previously described (Sharma et al., *EMBO J* 31, 829-841 (2012)). For turnover measurements with pharmacological iron-chelation, iNs were first treated for 72 h with the iron-chelators, and cycloheximide chase was performed in the presence of iron-chelators.

SDS-PAGE and Quantitative Immunoblotting

For SDS-PAGE, 10-15% Laemmli gels (10.3% T and 3.3% C) were used to separate proteins on Bio-Rad apparati. Proteins were transferred onto nitrocellulose (pore-size=0.45 m; GE Healthcare) and blocked with 5% w/v fat-free dry milk in tris buffered saline, pH 7.5 supplemented with 0.1% Tween 20 (TBS-T). Immunoblotting was performed by incubating the blocked membranes with primary antibodies in blocking buffer for 8-16 hours. Following 5 washes with TBS-Tween 20 (0.1%). Blots were incubated with secondary antibodies (goat anti-rabbit conjugated to IRDye 600RD or 800CW; LI-COR) at 1/5000 in blocking buffer for 1-3 hours. Immunoblots were washed 5× with TBS-T and dried, then scanned on Odyssey CLx (LI-COR) and quantified using Image-Studio software (LI-COR).

For ATP5G immunoblots, following the transfer, nitrocellulose membranes were dried and fixed for 15 min at room temperature in 0.2% glutaraldehyde in PBS. Ikegaki and Kennett, *Journal of immunological methods* 124: 205-210 (1989). Membranes were then washed 3× with TBS-T and treated as above.

Antibodies

Myc tag (Mouse=9E10 ascites and culture supernatant of hybridoma, DSHB; Rabbit=C3956, Sigma), GFP (mouse=JL8, Clontech), CSPα (Rabbit=R807 serum; ab1576, Millipore), SGT (Rabbit=CHAT33 serum), Hsc70 (Mouse=cl. 3C5, SYSY; Rabbit=A903 serum), SNAP-25 (Mouse=cl. 71.1, SYSY; Rabbit=P913 serum), Syb-2 (Mouse=cl. 69.1, SYSY; Rabbit=P939 serum), Synt-1 (Mouse=cl. 78.2, SYSY; Rabbit=438B serum), Map2 (Mouse=m1406, Sigma; Rabbit=ab5622, Millipore), ATP5G (Rabbit=ab181243, Abcam), VDAC1 (Mouse=cl. N152B/23, Neuromab), Tim23 (mouse=cl. 32/Tim23, BD Bioscience), β-Actin (A1978, Sigma).

Statistical Analyses

Each "n" consisted of reagents produced in parallel (e.g., purified proteins, plating of heterologous cells, lentivirus production, and culturing neurons from a single litter) and experiments performed in parallel (e.g. transfection or lentiviral infection, immunoprecipitation, sample collection for ELISA or immunoblotting etc.). Experiments were quantified using parametric as well as non-parametric statistical tests, as indicated in each figure caption. Nonparametric analyses were performed by Mann-Whitney-Wilcoxon U-test in case the sample distributions were not normal. Time-course experiments such as cycloheximide chase and Iron-chelator treatment were analyzed by 2-way ANOVA for comparing the overall curve and by Tukey's multiple comparisons post-test to compare data at each time-point independently.

Figure 1B:
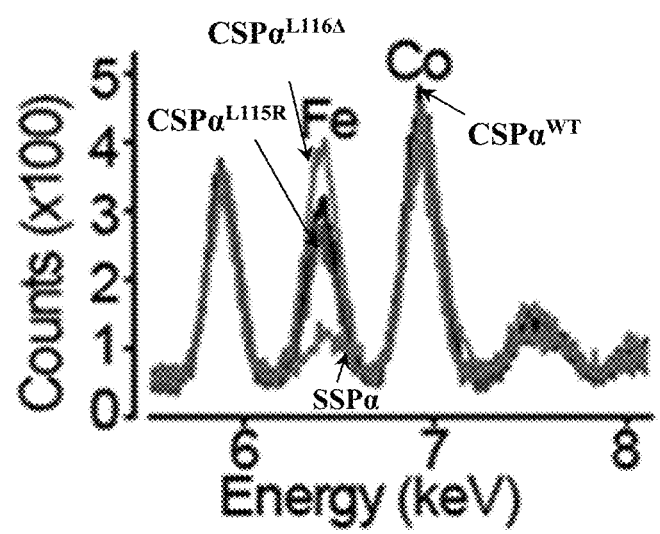

Example 2: Fe—S Cluster Binding and Oligomerization of CSPα In Vitro and in Mammalian Cells The effect of ANCL mutations on CSPα was studied in vitro, using recombinant proteins. As shown in FIG. 1A, visual analysis of purified CSPα$^{WT}$, CSPα$^{L115R}$ and CSPα$^{L116Δ}$ showed an amber-brown color, suggesting metal-binding, possibly via cysteine (Cys) residues of the Cys-string. Substitution of 13 Cys residues of the Cys-string to serines, termed serine string protein-α (SSPα), led to colorless protein (See FIG. 1A), suggesting that the Cys-string is coordinating the bound metal. As shown in FIG. 1B, X-ray fluorescence identified the metal bound to CSPα$^{WT}$, CSPα$^{L115R}$ and CSPα$^{L116\Delta}$ as iron, which was absent from SSPα.

Figure 1C:
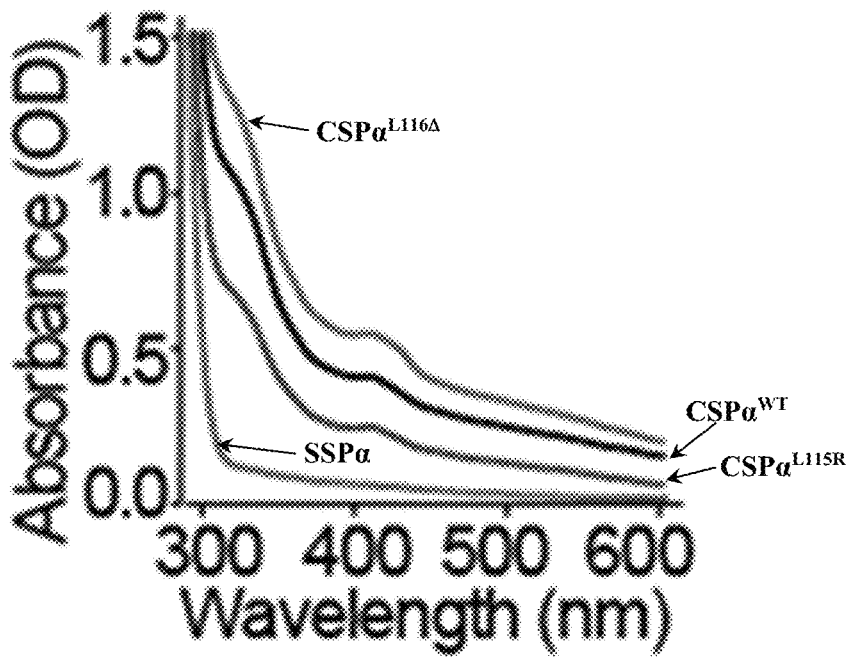
Figure 2A:
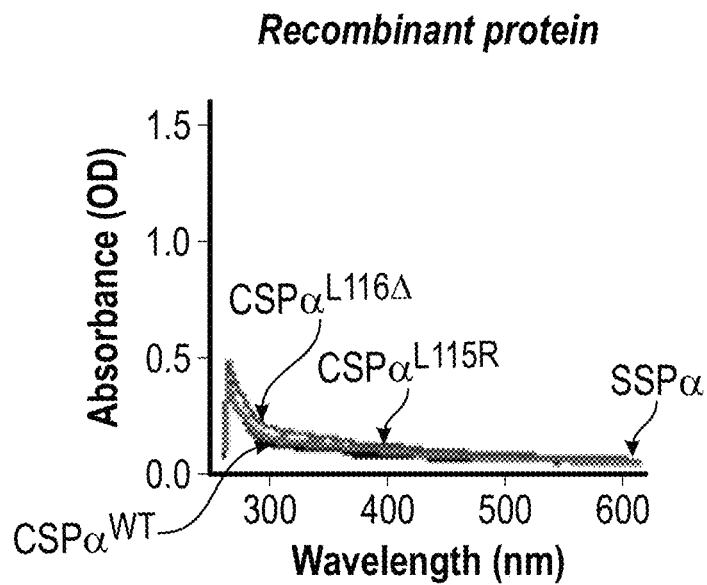
FIGS. 2A-2F show dissociation of CSPα ANCL mutant protein oligomers by acid treatment.

Cys-dependent iron-binding often indicates coordination of iron-sulfur (Fe—S) clusters, which is detectable by spectrometry. To confirm this hypothesis, UV-Vis spectrometry was performed. Dailey et al., *Biochemistry* 33: 403-407 (1994). As shown in FIG. 1C, UV-Vis spectrometry detected peaks at ~330 nm and ~417 nm, characteristic of Fe—S clusters, in CSPα$^{WT}$, CSPα$^{L115R}$ and CSPα$^{L116\Delta}$, but not in SSPα, suggesting that the Cys-string is coordinating Fe—S clusters. As expected of Fe—S clusters, the amber-brown proteins lost color upon acid treatment and UV-Vis peaks were also reduced (FIG. 2A). These results demonstrate that purified recombinant CSPα$^{WT}$, CSPα$^{L115R}$ and CSPα$^{L116\Delta}$ proteins form Fe—S clusters.

Figure 1D:
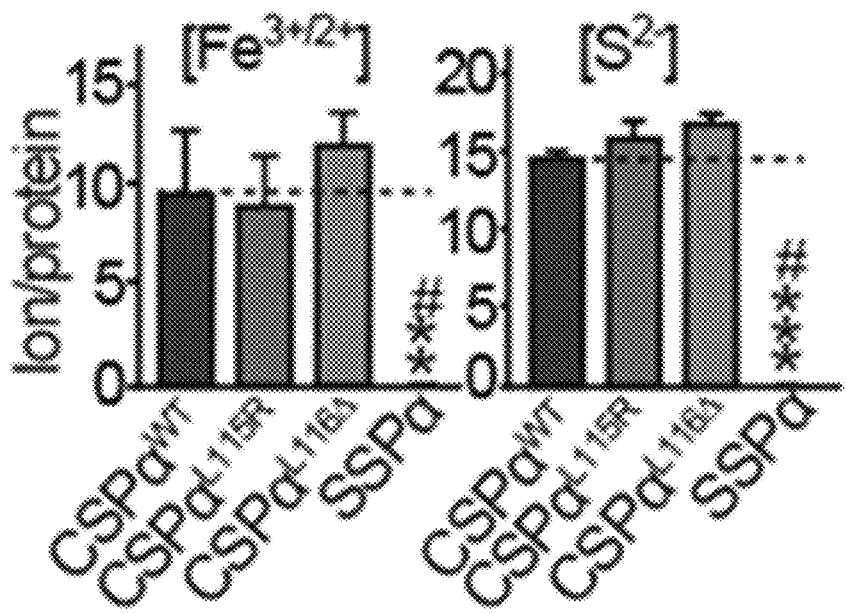

Ferric/ferrous iron (Fe$^{2+/3+}$) as well as inorganic sulfide (S$^{2-}$) ions bound to CSPα$^{WT}$, CSPα$^{L115R}$ and CSPα$^{L116\Delta}$ were quantified as ~7 Fe$^{2+/3+}$ and ~14 S$^{2-}$ ions per protein molecule (FIG. 1D). Neither Fe$^{2+/3+}$ nor S$^{2-}$ ions were detected in SSPα samples (FIG. 1D), suggesting that CSPα$^{WT}$, CSPα$^{L115R}$ and CSPα$^{L116\Delta}$ interact with Fe—S clusters via the Cys-string.

Figure 1E:
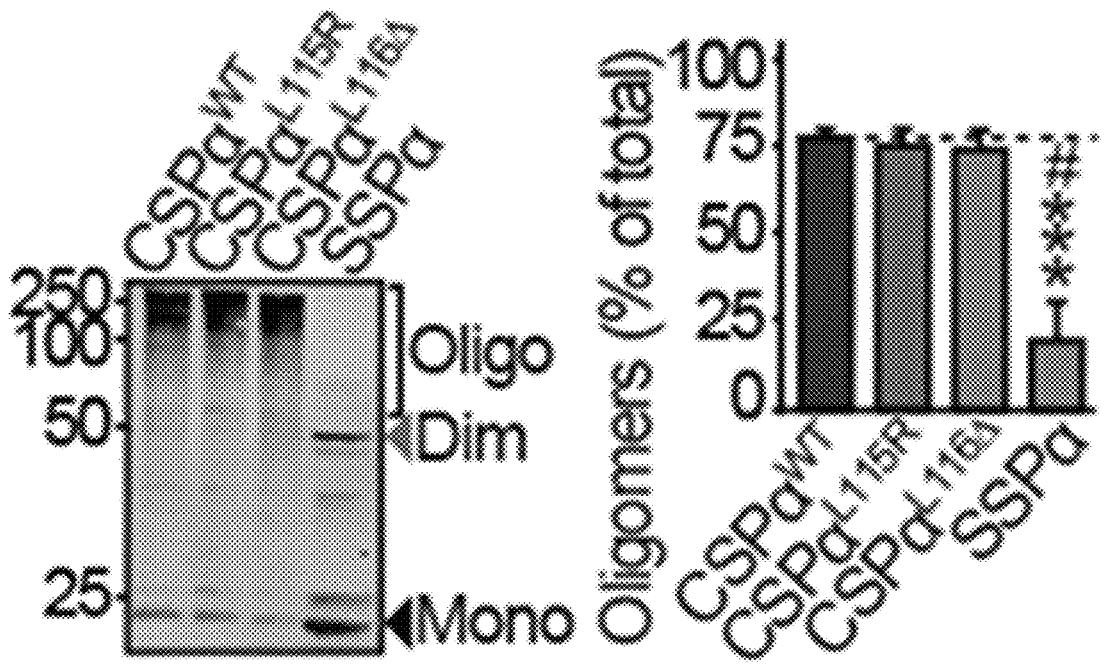
Figure 2B:
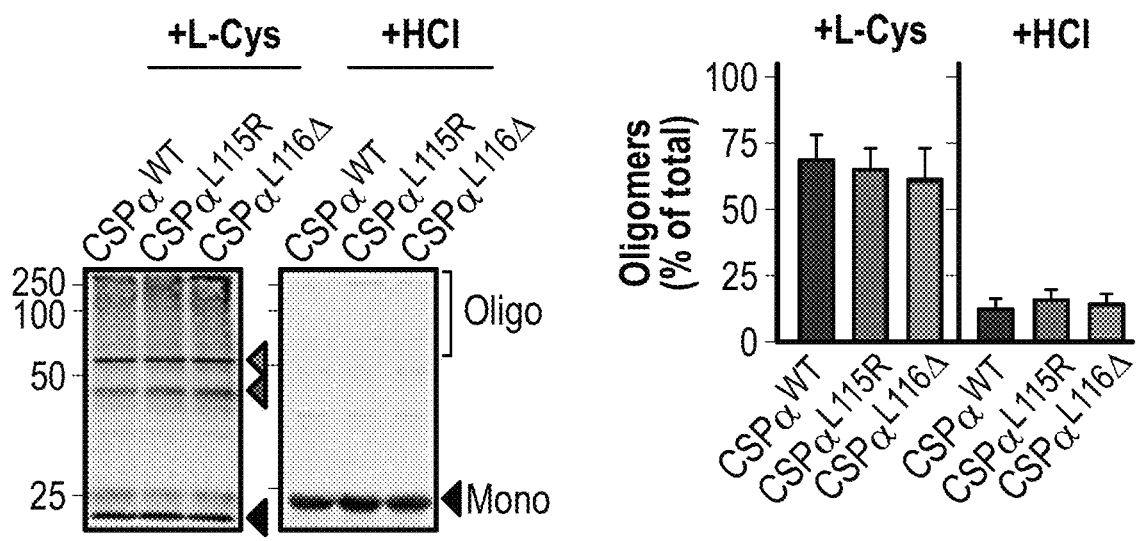
Figure 2C:
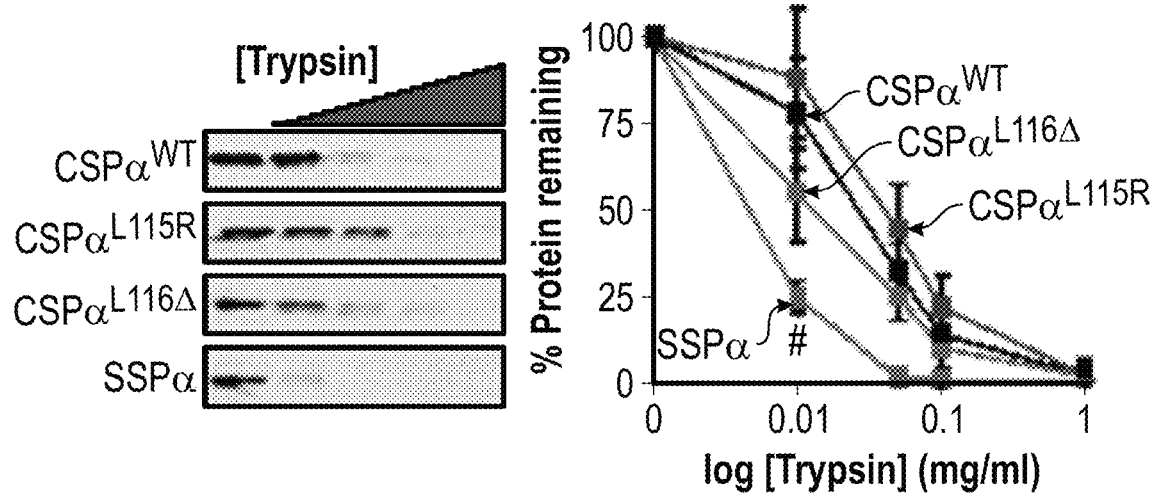
Figure 2D:
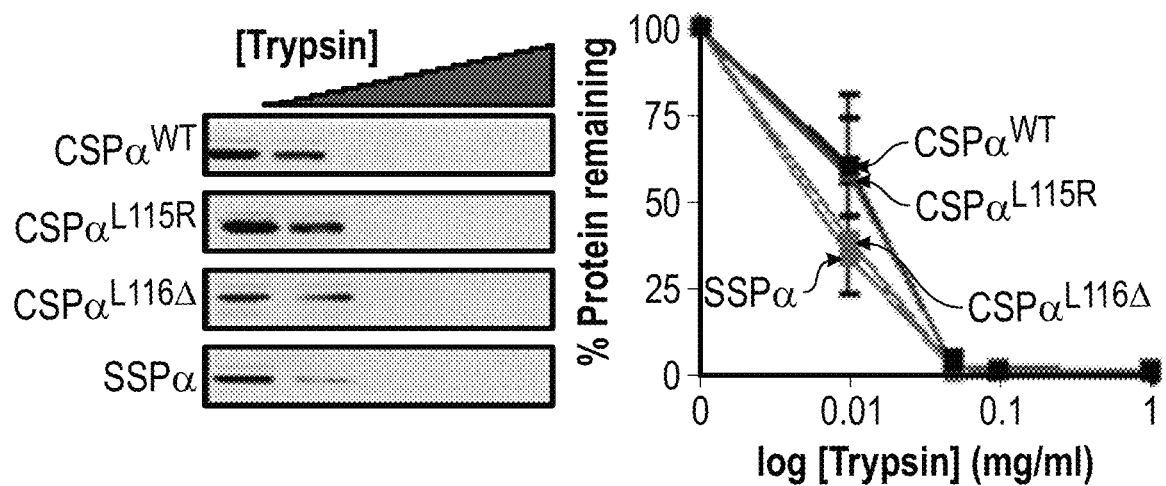

Since Fe—S clusters can covalently bridge protein monomers to cause oligomerization, it was hypothesized that cross-linking by Fe—S clusters may be the mechanism of mutant CSPα oligomerization. See Johansson et al., *J Biol Chem* 282: 3077-3082 (2007); Mesecke et al., *Biochemistry* 47: 1452-1463 (2008). Thus, SDS-resistant oligomerization status of CSPα variants was measured by sodium dodecyl sulfate polyacrylamide gel electrophoresis (SDS-PAGE) followed by Western blotting. Purified CSPα$^{WT}$, CSPα$^{L115R}$, CSPα$^{L116\Delta}$, and SSPα recombinant proteins were separated by SDS-PAGE, and resultant gels were subjected to immunoblotting using anti-CSPα antibody. As shown in FIG. 1E, about 75% of CSPα$^{WT}$, CSPα$^{L115R}$ and CSPα$^{L116\Delta}$ proteins existed as oligomers. Recombinant CSPα$^{WT}$, CSPα$^{L115R}$ and CSPα$^{L116\Delta}$ oligomerized into large aggregates, while SSPα was mostly monomeric, with some dimer formation. Oligomers of CSPα$^{WT}$, CSPα$^{L115R}$ and CSPα$^{L116\Delta}$ were disassembled into smaller oligomers and monomers, almost completely by acid treatment, while L-cysteine had no significant effect (FIG. 2B). Limited proteolysis experiments in native conditions found that CSPα$^{WT}$, CSPα$^{L115R}$ and CSPα$^{L116\Delta}$ are more resistant to trypsin cleavage than SSPα (FIG. 2C), suggesting seclusion of trypsin cleavage-sites in the oligomers. Accordingly, acid treatment made CSPα$^{WT}$, CSPα$^{L115R}$ and CSPα$^{L116\Delta}$ similarly susceptible to trypsin cleavage as SSPα (FIG. 2D). These results from recombinant proteins suggest that CSPα$^{WT}$, CSPα$^{L115R}$ and CSPα$^{L116\Delta}$ oligomerize by Fe—S cluster binding via their Cys-string regions.

Figure 1F:
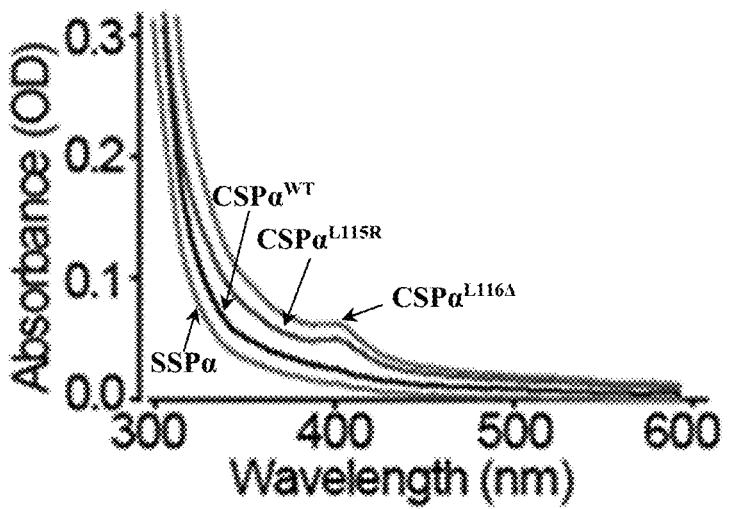
Figure 1G:
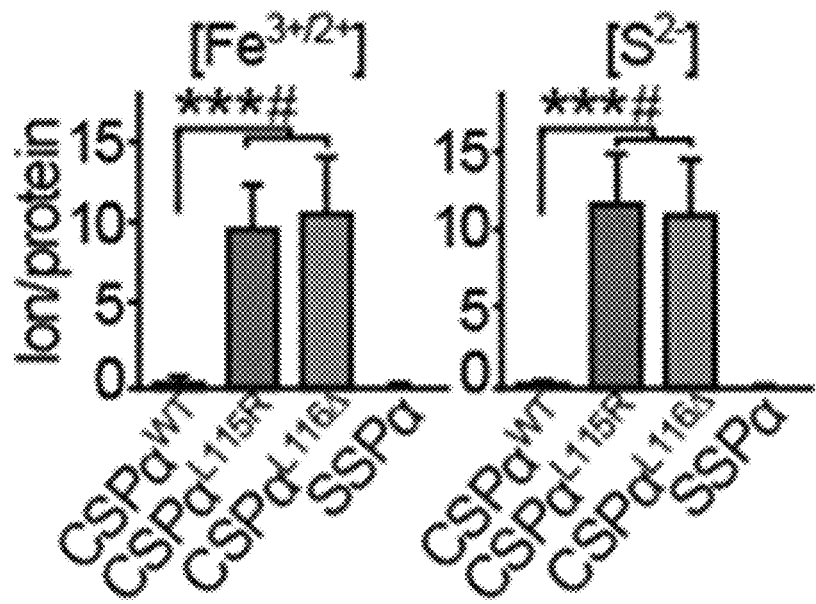
Figure 1H:
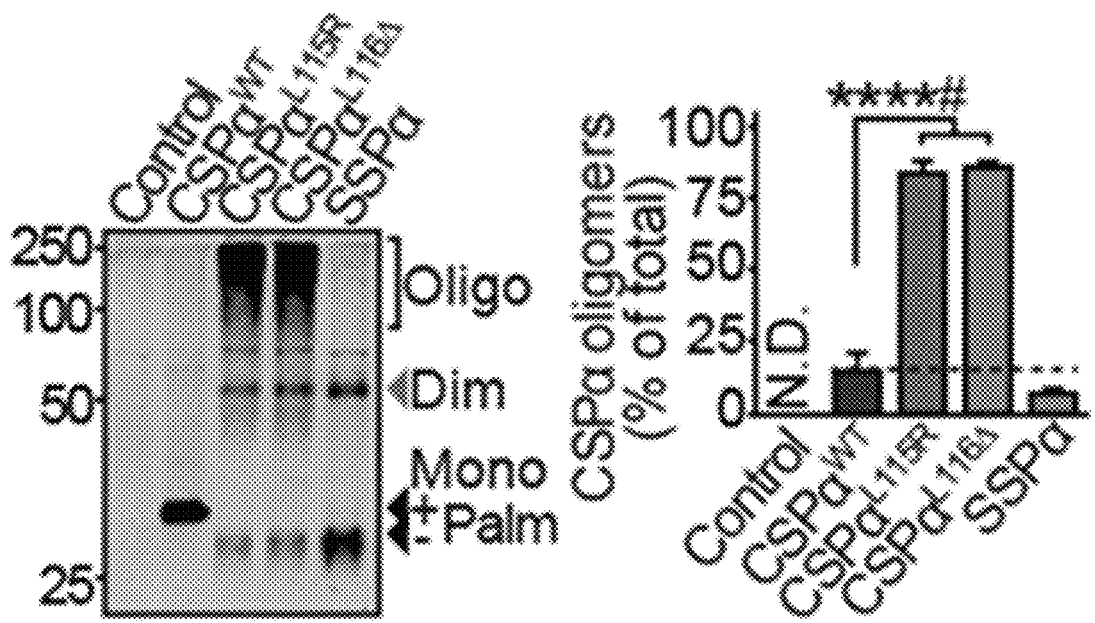
Figure 2E:
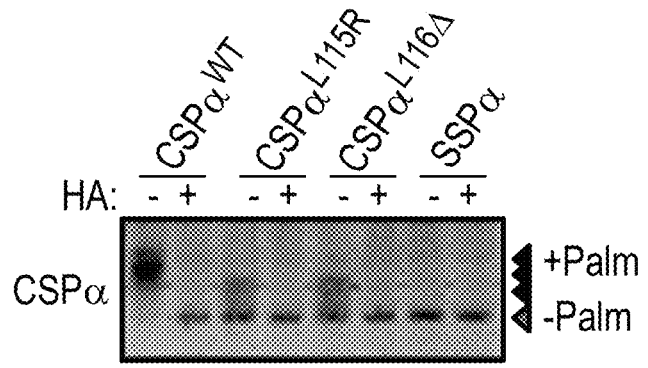
Figure 2E:
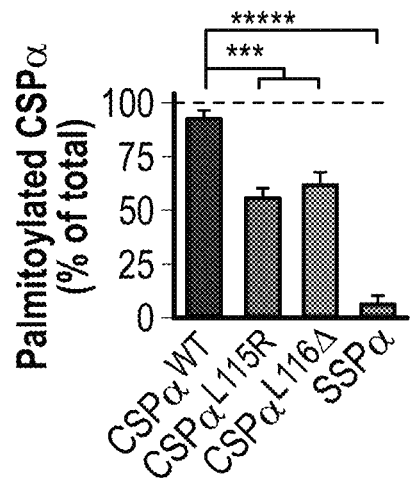
Figure 2F:
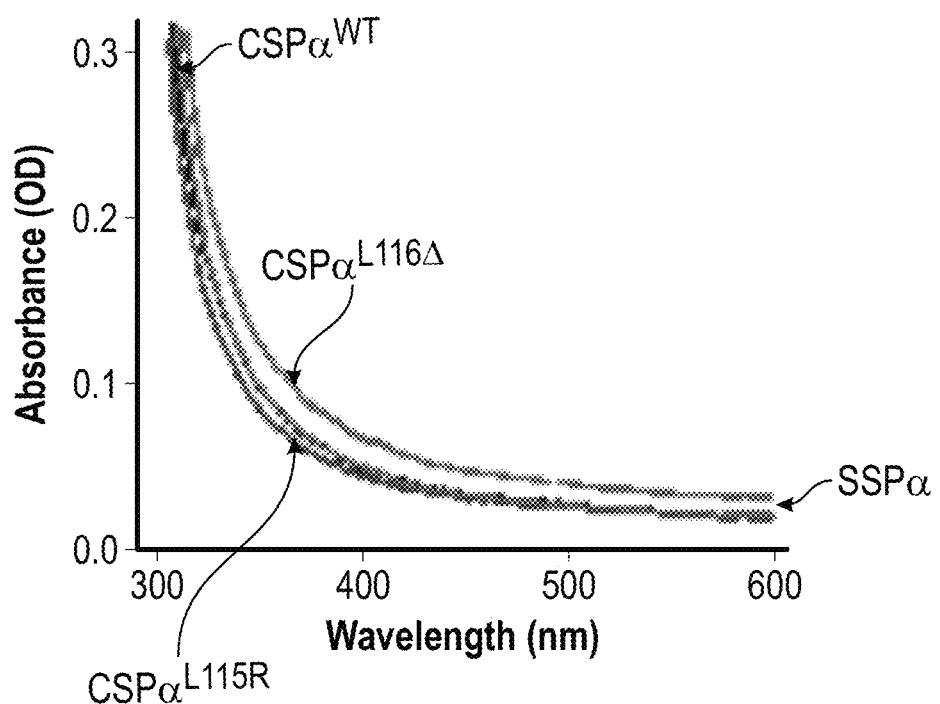

In eukaryotic cells, the Cys residues of CSPα's Cys-string are heavily palmitoylated (C. B. Gundersen et al., *J Biol Chem* 269, 19197-19199 (1994)), bringing the Cys-string into close apposition with lipid membranes, which may obviate their reaction with Fe—S clusters. CSPα$^{WT}$, CSPα$^{L115R}$, CSPα$^{L116\Delta}$ and SSPα were expressed in HEK293T cells. ~90% of CSPαWT was palmitoylated, while the ANCL mutants CSPα$^{L115R}$ and CSPα$^{L116\Delta}$ revealed severely reduced palmitoylation (FIG. 2E), detected by the mass-shift due to chemical depalmitoylation by hydroxylamine. When isolated by immunoprecipitation, only CSPα$^{L115R}$ and CSPα$^{L116\Delta}$ showed the signature peaks of Fe—S clusters, while CSPα$^{WT}$ and SSPα lacked these peaks (FIG. 1F). Acid treatment eliminated the signature of Fe—S clusters in the UV-Vis profiles of CSPα$^{L115R}$ and CSPα$^{L116\Delta}$ (FIG. 2F). Fe$^{2+/3+}$ and inorganic S$^{2-}$ were detected only in CSPα$^{L115R}$ and CSPα$^{L116\Delta}$, with an Fe:S ratio close to 1 (FIG. 1G), pointing to Fe—S cluster binding specifically by the ANCL mutants of CSPα via their Cys-string in HEK293T cells. This binding of Fe—S clusters specifically to CSPα$^{L115R}$ and CSPα$^{L116\Delta}$ was accompanied by their oligomerization, while CSPα$^{WT}$ and SSPα did not form oligomers (FIG. 1H). Taken together, these results from recombinant and eukaryotic cell-derived proteins suggest that deficient Cys-palmitoylation allows oligomerization of CSPα$^{L115R}$ and CSPα$^{L116\Delta}$ via Fe—S cluster binding at their Cys-string region.

Figure 3A:
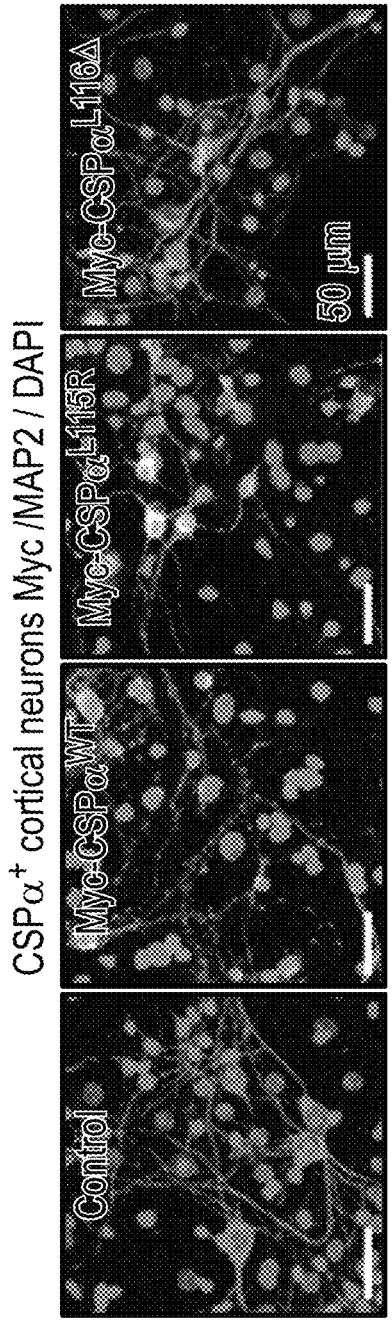
FIGS. 3A-3E show that mislocalization of the oligomerized CSPα mutants leads to downstream SNARE defects, which are alleviated by iron-chelators in neurons. For the experiments shown in FIGS. 3A-3E, primary cortical neurons from neonatal CSPα$^{-/-}$ mice were infected with lentiviruses expressing Myc-tagged CSPα$^{WT}$, CSPα$^{L115R}$, CSPα$^{L116\Delta}$, SSPα, or empty lentivirus (Control) on 7 days in vitro (DIV) and examined on 17 DIV.

Example 3: ANCL Mutations Cause Mislocalization, and Oligomerization of Mutant CSPα Via Ectopic Iron-Sulfur (Fe—S) Cluster-Binding in Neurons CSPα is heavily expressed in neurons. Zinsmaier et al., *J Neurogenet* 7: 15-29 (1990); Kohan et al., *J Neurosci* 15: 6230-6238 (1995). CSPα is a pre-synaptically localized chaperone. Tobaben et al., *Neuron* 31: 987-999 (2001); Sharma et al., *Nat Cell Biol* 13: 30-39 (2011); Zinsmaier et al., *Science* 263: 977-980 (1994); Umbach et al., *Neuron* 13: 899-907 (1994). The most devastating symptoms and pathology of ANCL are neurological. Martin: *Dev Neurosci* 13: 331-338 (1991); Goebel and Braak: *Clin Neuropathol* 8: 109-119 (1989). Thus, Myc-tagged CSPα$^{WT}$, CSPα$^{L115R}$, or CSPα$^{L116\Delta}$ proteins were expressed using a lentiviral vector in primary cortical neurons from CSPα knockout (CSPα$^{-/-}$) mice. Localization of CSPα$^{WT}$, CSPα$^{L115R}$, CSPα$^{L116\Delta}$ or SSPα proteins was studied using immunofluorescence microscopy. Cells infected with empty lentivirus was used as a negative control for Myc immunofluorescence signal. As shown in FIG. 3A, whereas CSPα$^{WT}$ protein localized to synapse-like puncta on neurites, CSPα$^{L115R}$ and CSPα$^{L116\Delta}$ proteins accumulated mostly within the cell body with minimal localization at neurites. CSPα$^{L115R}$ and CSPα$^{L116\Delta}$ mutant proteins accumulated mostly within the cell body with minimal localization at neurites. Therefore, ANCL mutations cause mislocalization of CSPα.

To determine whether CSPα$^{L115R}$ and CSPα$^{L116\Delta}$ form oligomers in neurons, cell-free extracts were resolved by SDS-PAGE followed by Western blotting. As shown in FIG. 4A, CSPα$^{L115R}$ and CSPα$^{L116\Delta}$ accumulated as oligomers with large molecular masses. Neither CSPα$^{WT}$ protein, nor the SSPα mutant protein exhibited oligomers with large molecular masses in neurons, which could be dissociated by acid treatment. These results indicate that CSPα$^{L115R}$ and CSPα$^{L116\Delta}$ proteins undergo protein oligomerization/aggregation, which depends on the presence of cysteine in these proteins, consistent with the formation of Fe—S clusters.

FIG. 4A shows that CSPα$^{WT}$ protein revealed a small mass-shift indicative of palmitoylation. As shown in FIG. 4B, CSPα$^{L115R}$ and CSPα$^{L116\Delta}$ protein oligomers were almost completely disassembled by acid treatment into smaller oligomers and monomers. As shown in FIG. 4A-4B, whereas CSPα$^{WT}$ was nearly fully palmitoylated in neurons, levels of palmitoylation were diminished in case of CSPα$^{L115R}$ and CSPα$^{L116\Delta}$ mutants, compared to CSPα$^{WT}$ indicating a palmitoylation deficit.

These results demonstrate that the cysteine string region of CSPα, which is normally palmitoylated, loses palmitoylation due to the ANCL mutations in neurons, which is associated with mislocalization, and oligomerization of mutant CSPα via ectopic iron-sulfur (Fe—S) cluster-binding. Mislocalization of CSPα causes deficiency in its SNARE-chaperoning function, leading to reduced levels of the neuronal SNARE protein SNAP-25, and reduced SNARE-complex assembly, which explains the observed phenotypes of ANCL (Kufs disease).

Figure 3B:
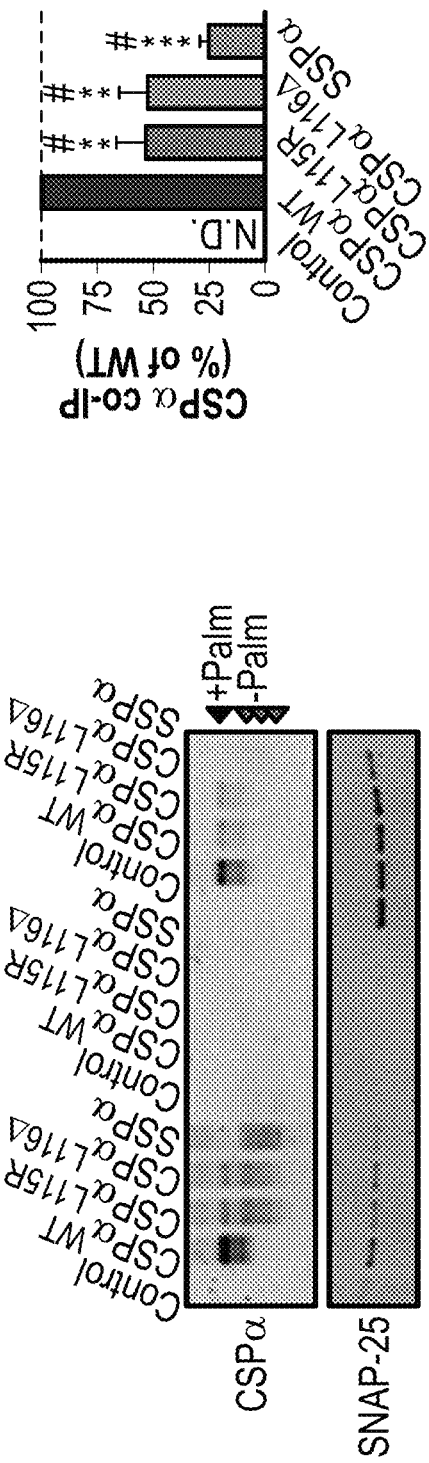

Example 4: Mislocalization of the Oligomerized CSPα Mutant Proteins Leads to Downstream SNARE Defects in Neurons As shown in FIG. 4A, levels of SNAP-25 were reduced in $CSPα^{L115R}$ and $CSPα^{L116Δ}$ mutants, compared to $CSPα^{WT}$, which provided hints that mislocalization of the ANCL mutants $CSPα^{L115R}$ and $CSPα^{L116Δ}$ away from synapses may explain the molecular basis for the phenotype of ANCL. SNAP-25 is the best characterized client of CSPα's chaperone function. It is also a component of the synaptic SNARE (Soluble NSF Attachment Protein (SNAP) Receptor) protein complex. Sharma et al., Nat Cell Biol 13: 30-39 (2011); Chandra et al., Cell 123: 383-396 (2005); Sharma et al., EMBO J 31: 829-841 (2012). To examine the interaction of $CSPα^{L115R}$ and $CSPα^{L116Δ}$ mutant proteins with SNARE proteins, co-immunoprecipitation experiments from $CSPα^{-/-}$ neurons expressing CSPα variants using anti-SNAP-25 monoclonal antibody were carried out. As shown in FIG. 3B, the interaction of $CSPα^{L115R}$ and $CSPα^{L116Δ}$ with SNAP-25 was significantly reduced compared to $CSPα^{WT}$. In $CSPα^{-/-}$ mice, complete loss-of-function is known to result in reduced SNAP-25 protein levels. Sharma et al., Nat Cell Biol 13: 30-39 (2011); Chandra et al., Cell 123: 383-396 (2005); Sharma et al., EMBO J 31: 829-841 (2012). As shown in FIG. 4A, while expression of $CSPα^{WT}$ in $CSPα^{-/-}$ neurons increased SNAP-25 levels as expected, $CSPα^{L115R}$ and $CSPα^{L116Δ}$ expression led to no significant improvement in SNAP-25 levels, similar to the SSPα mutant, suggesting $CSPα^{L115R}$ and $CSPα^{L116Δ}$ ANCL mutations cause an almost complete loss of CSPα function, likely due to its oligomerization and mislocalization away from the client SNAP-25.

Figure 3C:
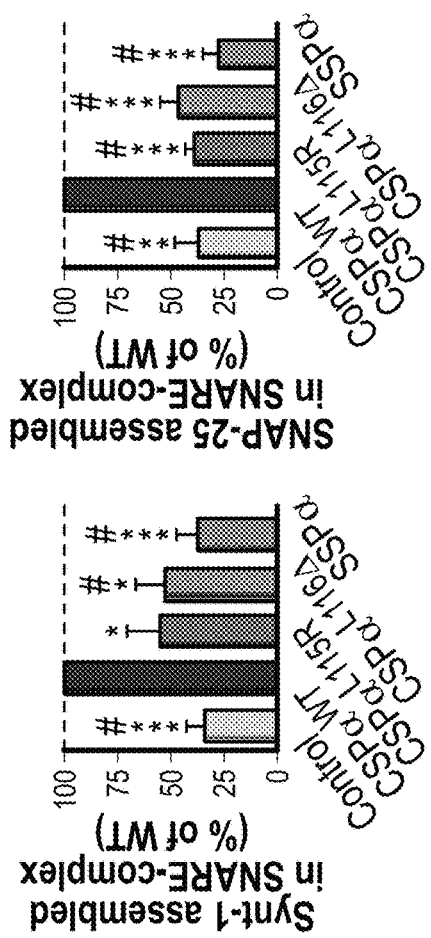

Reduced SNAP-25 levels can affect the assembly of SNARE-complexes (Sharma et al., Nat Cell Biol 13: 30-39 (2011)), which comprise SNAP-25, syntaxin-1 (Synt-1), and VAMP-2/synaptobrevin-2 (Syb-2), and is the functional core-unit that catalyzes synaptic vesicle release. To quantify SNARE-complex assembly in $CSPα^{-/-}$ neurons expressing the CSPα variants, Syb-2 was immunoprecipitated and SNARE-complex assembly was measured by tracking the co-immunoprecipitated SNAP-25 and syntaxin-1. As shown in FIG. 3C, whereas the co-immunoprecipitated SNAP-25 and syntaxin-1 was more-than-doubled by $CSPα^{WT}$ expression, $CSPα^{L115R}$, $CSPα^{L116Δ}$ and SSPα had no significant effect.

Overall, these data suggest that ANCL mutations in CSPα cause: a) reduced palmitoylation of the Cys-string, allowing for b) Fe—S cluster binding at the Cys-string, leading to c) oligomerization and mislocalization of CSPα. This sequestration of mutant CSPα away from the synapses cause a downstream deficit in interaction with its synaptic client SNAP-25, reducing SNAP-25's proteins levels and its assembly into SNARE-complexes. With this understanding of the molecular-cellular cascade of defects caused by ANCL mutations, experiments were aimed at modifying the Fe—S cluster-dependent oligomerization of $CSPα^{L115R}$ and $CSPα^{L116Δ}$.

These results demonstrate that the cysteine string region of CSPα, which is normally palmitoylated, loses palmitoylation due to the ANCL mutations in neurons, which is associated with mislocalization, and oligomerization of mutant CSPα via ectopic iron-sulfur (Fe—S) cluster-binding. Mislocalization of CSPα causes deficiency in its SNARE-chaperoning function, leading to reduced levels of the neuronal SNARE protein SNAP-25, and reduced SNARE-complex assembly, which explains the observed phenotypes of ANCL (Kufs disease).

Example 5: Iron-Chelators Rescue the Defects of CSPα ANCL Mutants

Figure 3D:
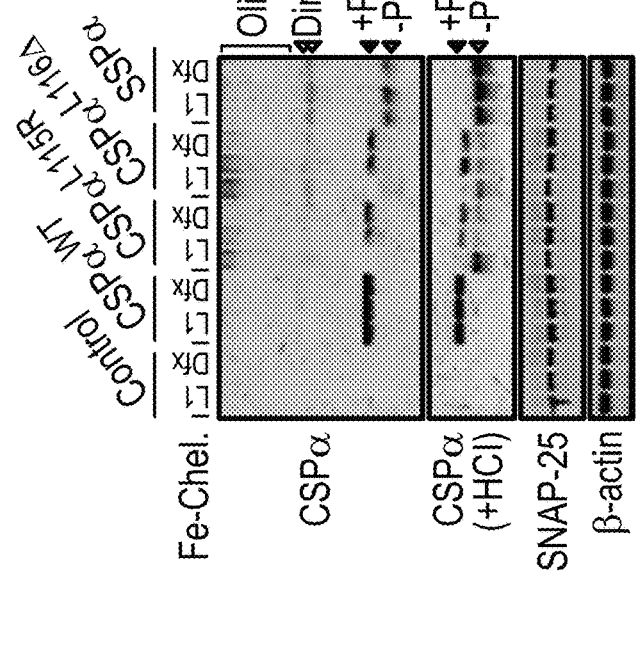

To understand whether destabilization of Fe—S clusters would rescue the defects in palmitoylation and ectopic oligomerization and Fe—S cluster formation by CSPα ANCL mutant proteins, the following experiments were conducted. The iron-chelators deferiprone (L1) and deferoxamine (Dfx), both already in human use for treating iron-overload, were used for this purpose. $CSPα^{-/-}$ primary cortical neurons were infected with lentiviral vectors to express Myc-tagged $CSPα^{WT}$, $CSPα^{L115R}$, $CSPα^{L116Δ}$, SSPα proteins, or empty lentivirus on fifth day in vitro (DIV). On 12 DIV the cells were treated with vehicle (no treatment control), or iron chelators 200 μM deferiprone (L1) and 200 μM deferoxamine (Dfx) for 72 h, and cell extracts were resolved by SDS-PAGE, and subjected to quantitative immunoblotting using indicated antibodies against CSPα, SNAP-25 or β-actin (loading control). As shown in FIG. 3D, both L1 and Dfx reduced the oligomerization of $CSPα^{L115R}$ and $CSPα^{L116Δ}$ expressed in $CSP^{-/-}$ neurons. Surprisingly, as shown in FIG. 3D, palmitoylation of $CSPα^{L115R}$ and $CSPα^{L116Δ}$ was also improved by the treatment with L1 or Dfx, suggesting that Fe—S clusters compete with physiological modification by acyl chains (e.g. palmitoylation) for CSPα's Cys residues, and that iron-chelators may be useful in mitigating Fe—S cluster binding and oligomerization of $CSPα^{L115R}$ and $CSPα^{L116Δ}$.

These results demonstrate that the iron chelators of the present technology are useful in methods for treating a disease caused by ectopic Fe—S cluster formation in a subject in need thereof. These results demonstrate that the iron chelators of the present technology are useful in methods for treating Adult-onset Neuronal Ceroid Lipofuscinosis (ANCL or Kufs disease) in a subject in need thereof.

To understand effect of iron chelators on the function of the SNARE-complex, cell extracts of iron chelator-treated $CSPα^{-/-}$ primary cortical neurons, expressing Myc-tagged the CSPα derivatives, were used for immunoblotting. SNAP-25 levels from total lysate were measured by quantitative immunoblotting using anti-SNAP-25 antibody and β-actin for normalization. As shown in FIG. 3D, reduced oligomerization and improved palmitoylation of $CSPα^{L115R}$ and $CSPα^{L116Δ}$ by L1 and Dfx were accompanied by augmentation of SNAP-25 levels by approximately two-fold in neurons expressing $CSPα^{L115R}$ and $CSPC^{L116Δ}$ bringing SNAP-25 levels closer to those in $CSPα^{WT}$ expressing neurons. Interestingly, neither L1 nor Dfx affected SNAP-25 levels in neurons expressing $CSPα^{WT}$ or SSPα (See FIG. 3D), indicating that L1 and Dfx affect SNAP-25 only indirectly. These data suggest that iron chelators salvage the synaptic-chaperone activity of $CSPα^{L115R}$ and $CSPα^{L116Δ}$ mutant proteins, and thereby stabilize SNAP-25, which is a client of CSPα.

Figure 3E:
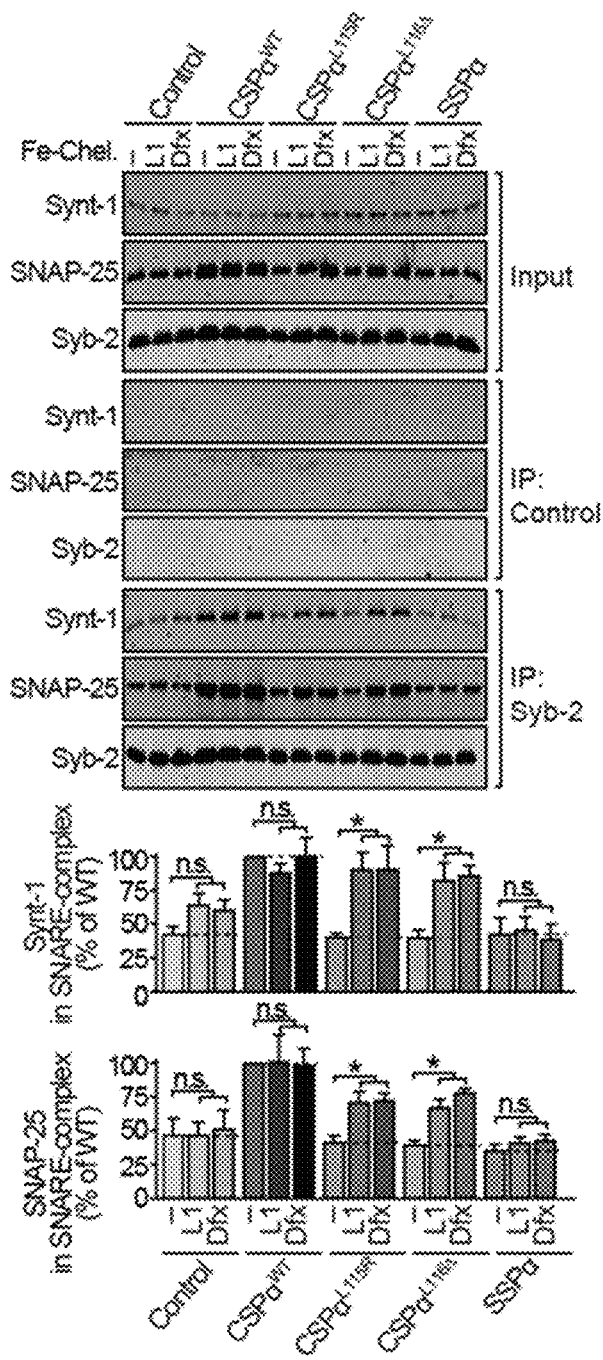

To probe the effect of iron chelators on the function of the SNARE-complex further, $CSPα^{-/-}$ primary cortical neurons, expressing Myc-tagged the wild-type and mutant CSPα derivatives, were treated with vehicle only (negative control), L1 or Dfx. Cell free extracts were immunoprecipitated using anti-Syb-2 antibody and co-immunoprecipitation of Synt-1 and SNAP-25 was analyzed. As shown in FIG. 3E, when anti-Syb-2 antibody was used for immunoprecipitation, Synt-1 and SNAP-25 were co-immunoprecipitated. As expected, a negative control antibody did not pull Synt-1 and SNAP-25 (FIG. 3E). These SNARE co-immunoprecipitation experiments show that L1 and Dfx treatment led to increased level of co-immunoprecipitated Synt-1 and SNAP-25, compared to the vehicle only (negative control). Iron chelators had no effect in neurons expressing either CSPα$^{WT}$ or SSPα (FIG. 3E). These data suggest amelioration of SNARE-complex assembly defects in CSPα$^{L115R}$ and CSPα$^{L116\Delta}$ expressing neurons by iron chelators.

Taken together, these studies show that L1 and Dfx not only improve palmitoylation and reduce oligomerization of CSPαL$^{115R}$ and CSPα$^{L116\Delta}$ in neurons, but this also leads to functional rescue—evident from the increase in SNAP-25 levels and its improved assembly into synaptic SNARE-complexes. These results demonstrate that the iron chelators of the present technology are useful in methods for treating Adult-onset Neuronal Ceroid Lipofuscinosis (ANCL or Kufs disease) in a subject in need thereof.

These results demonstrate that the iron chelators of the present technology are useful in methods for treating a disease caused by ectopic Fe—S cluster formation, such as ANCL or Kufs disease, in a subject in need thereof.

Example 6: CSPα ANCL Mutations are Dominant Negative

CSPα mutations are autosomal dominant in ANCL patients, while a loss of a single allele has no detectable phenotype in CSPα hemizygous mice (R. Fernindez-Chacón et al., Neuron 42, 237-251 (2004)). Thus, a dominant-negative pathogenic mechanism has been proposed for ANCL, based on the observation that oligomers of mutant CSPα protein incorporates WT CSPα protein as well; possibly initiated via physiological dimerization of CSPα (J. E. Braun, R. H. Scheller, Neuropharmacology 34, 1361-1369 (1995), L. H. Chamberlain, R. D. Burgoyne, Biochem J 322 (Pt 3), 853-858 (1997)).

Figure 5:
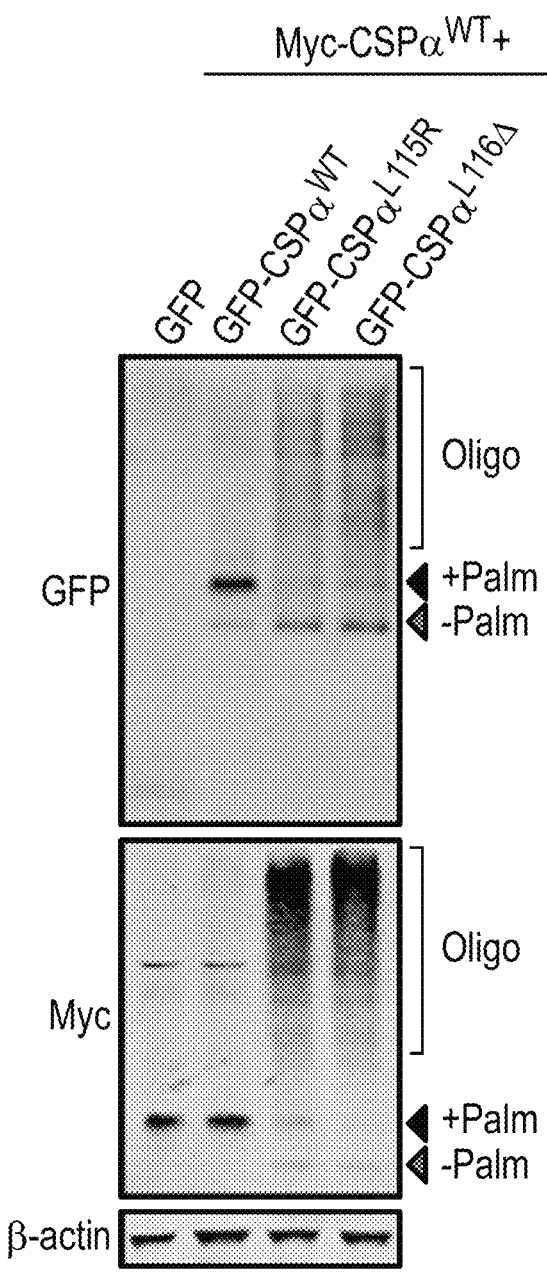
FIG. 5 shows that mutant CSPα draws wild-type CSPα into aggregates. CSPα$^{-/-}$ primary cortical neurons were lentivirally transduced to co-express Myc-CSPα$^{WT}$ with either GFP-CSPα$^{WT}$, GFP-CSPα$^{L115R}$, or GFP-CSPα$^{L116\Delta}$ (control=GFP alone). Cell extracts were immunoblotting using anti-Myc or anti-GFP antibody. Shown is one representative experiment from n=3. Oligo=oligomerized; Palm=palmitoylated.

Next, Myc-CSPα$^{WT}$ was co-expressed with GFP-CSPα$^{WT}$, GFP-CSPα$^{L115R}$, or GFP-CSPα$^{L116\Delta}$ in primary cortical neurons, and palmitoylation of CSPα, and levels of its client SNAP-25 in these cells were accessed by immunoblotting. Cells expressing GFP alone were used as a control for expression of GFP by itself. As shown in FIG. 5, CSPα$^{-/-}$ primary cortical neurons co-expressing the ANCL mutants GFP-CSPα$^{L115R}$ and GFP-CSPα$^{L116\Delta}$ with Myc-CSPα$^{WT}$ exhibited oligomerization of Myc-CSPα$^{WT}$. In contrast, CSPα$^{-/-}$ primary cortical neurons co-expressing the GFP-CSPα$^{WT}$ with Myc-CSPα$^{WT}$ did not exhibit such oligomerization. These data show that oligomers of mutant CSPα protein incorporates WT CSPα protein, explaining the dominant negative phenotype of ANCL mutants. Neurons co-expressing the ANCL mutants GFP-CSPα$^{L115R}$ and GFP-CSPα$^{L116\Delta}$ with Myc-CSPα$^{WT}$ also showed reduced Myc-CSPα$^{WT}$ palmitoylation, compared to the neurons co-expressing the GFP-CSPα$^{WT}$ with Myc-CSPα$^{WT}$ (FIG. 5). The CSPα$^{-/-}$ primary cortical neurons co-expressing the ANCL mutants GFP-CSPα$^{L115R}$ and GFP-CSPα$^{L116\Delta}$ with Myc-CSPα$^{WT}$ also showed reduced SNAP-25 levels, compared to the neurons co-expressing the GFP-CSPα$^{WT}$ with Myc-CSPα$^{WT}$. When cell-free extracts were treated with HCl, the oligomers dissociated.

Figure 6A:
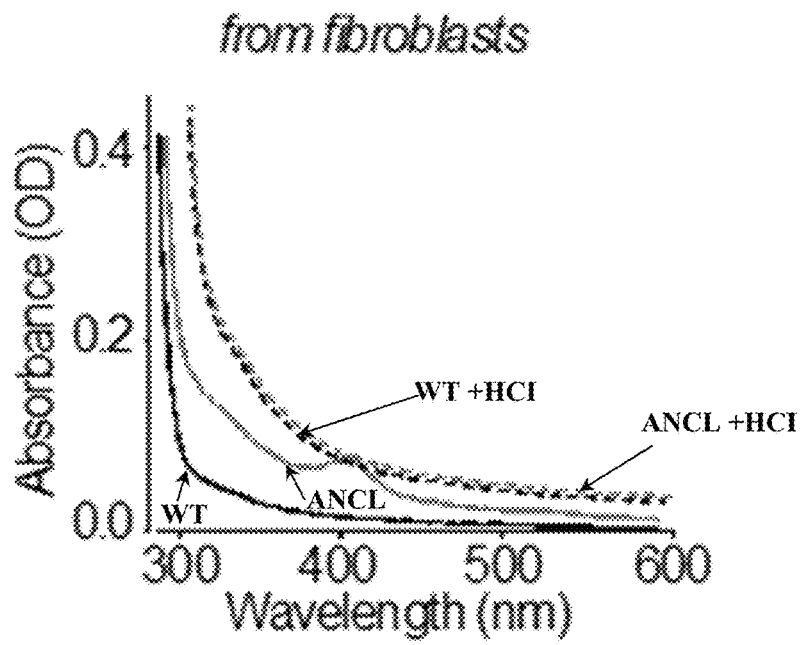
FIGS. 6A-6H show that ANCL patient-derived fibroblasts and induced neuronal cells (iNs) reveal CSPα defects with downstream SNAP-25 instability and lipofuscin accumulation.
Figure 6B:
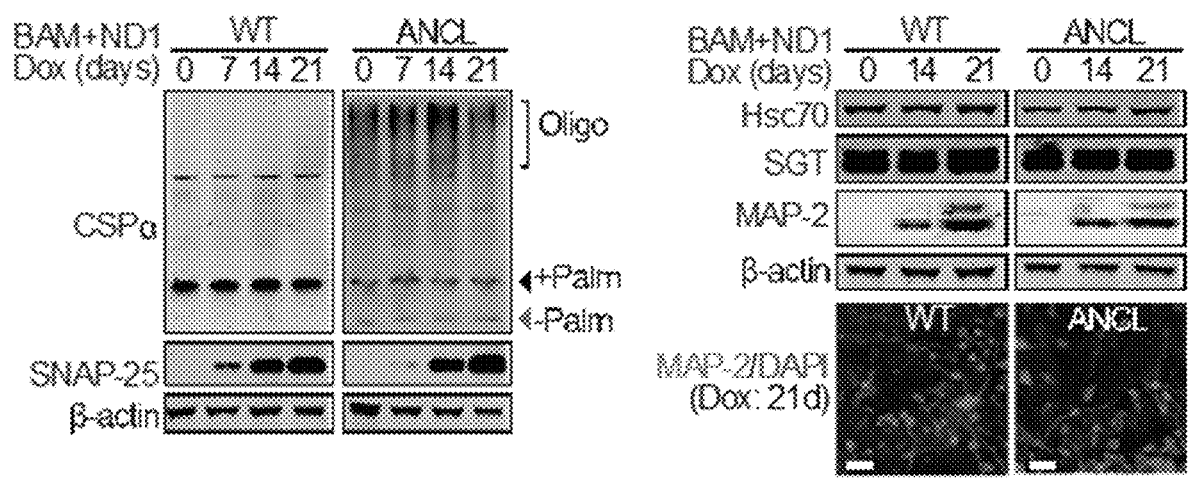

Next, fibroblasts from an ANCL patient who carried the CSPα$^{L116\Delta}$ allele were used. Velinov et al., PLoS One 7: e29729 (2012). Fibroblasts from an unaffected sex- and age-matched individual (WT) served as a positive control for wild-type function. CSPα was immunoprecipitated from ANCL or WT fibroblasts and UV-Vis spectroscopy was performed. As shown in FIG. 6A, UV-Vis spectroscopy showing the characteristic absorbance of Fe—S clusters, featuring peaks at ~330 nm and ~417 nm, was evident when CSPα was immunoprecipitated from ANCL fibroblasts but not in WT fibroblasts. As shown in FIG. 6B (0 days), CSPα as well as it's well-characterized interactors Hsc70 and SGT were expressed in fibroblasts, derived either from an ANCL patient (ANCL) or unaffected sex- and age-matched individual (WT).

However, while the CSPα/Hsc70/SGT chaperone complex was expressed in fibroblasts, the neuronal client of this complex—SNAP-25—was not observed in fibroblasts (FIG. 6B (0 days)). Therefore, the patient fibroblasts were converted into iNs, by lentiviral co-expression of the four transcription factors Brn2, Ascl1, Myt11, and NeuroD1. Pang et al., Nature 476: 220-223 (2011) (See FIG. 6B). The dominant-negative effect of the ANCL-mutant CSPα on WT CSPα was studied further in ANCL patient-derived fibroblasts and induced neurons (iNs), which co-express the CSPα$^{WT}$ and CSPα$^{L116\Delta}$ alleles.

Figure 6C:
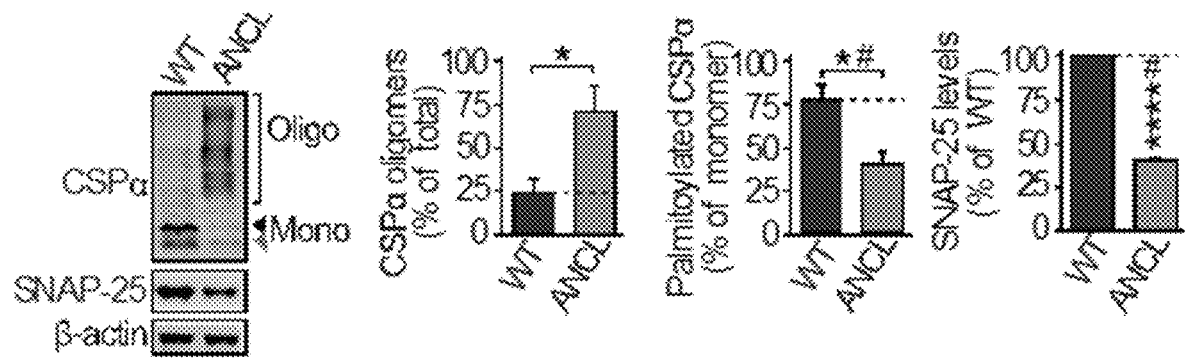
Figure 6D:
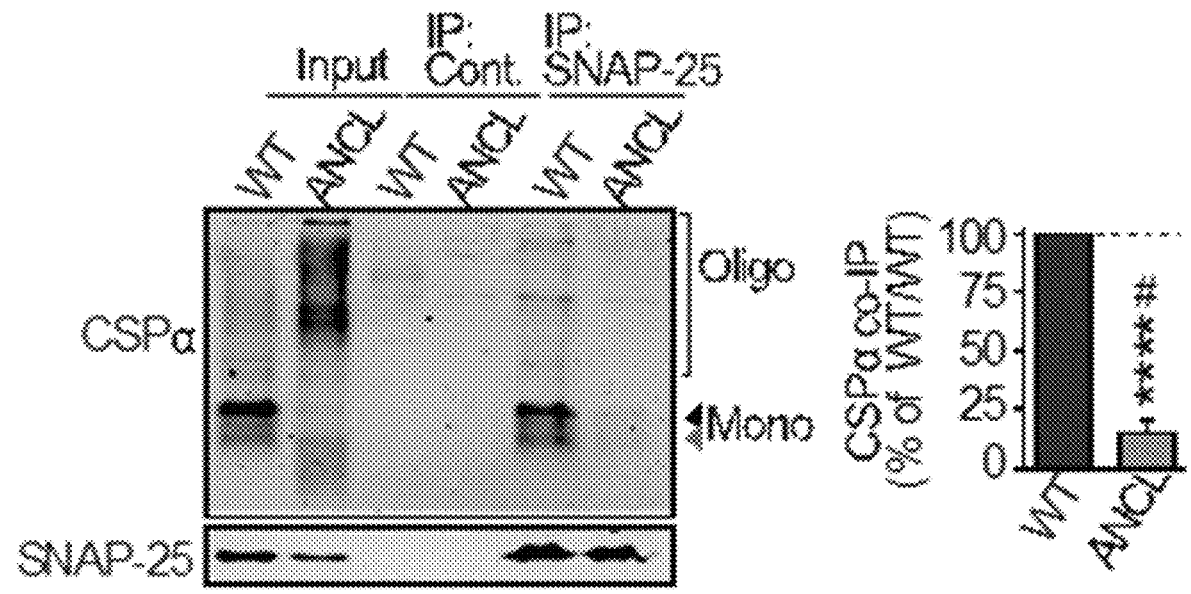
Figure 6E:
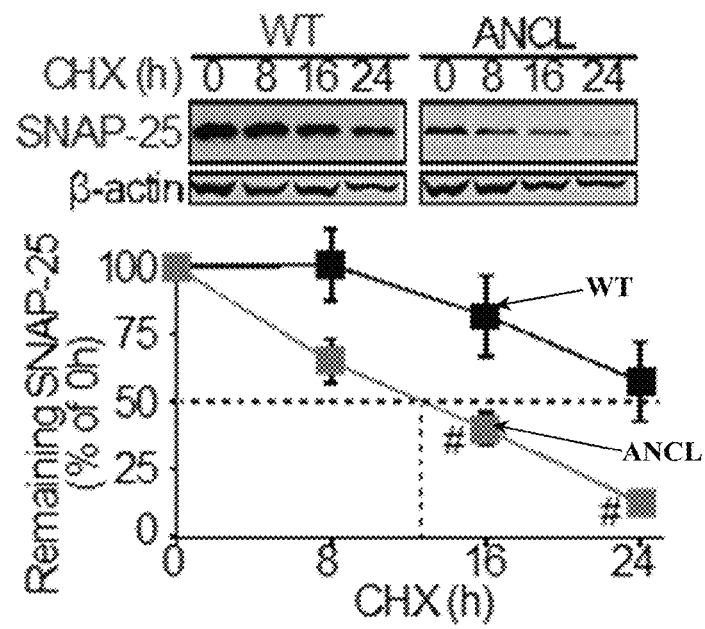

As shown in FIG. 6B (left panel), CSPα palmitoylation was reduced in ANCL iNs compared to WT iNs. FIG. 6B also shows that ANCL iNs showed increased oligomerization of CSPα compared to WT iNs. Accordingly, as shown in FIG. 6C, levels of its neuronal client SNAP-25 were reduced in ANCL iNs compared to WT iNs. To probe this further, extracts of ANCL and WT iNs were immunoprecipitated with anti-SNAP25 antibody and co-immunoprecipitation of CSPα was monitored. As shown in FIG. 6D, the interaction of CSPα with SNAP-25 was reduced in the ANCL iNs compared to WT iNs. The reduced levels of SNAP-25 ANCL iNs compared to WT iNs (FIG. 6C) is likely a result of the reduced interaction of CSPα with SNAP-25 in the ANCL iNs (FIG. 6D). CSPα chaperones the natively unfolded monomeric SNAP-25, and prevents its rapid degradation by the ubiquitin-proteasome system. Sharma et al., Nat Cell Biol 13: 30-39 (2011). To confirm whether CSPα affects stability of SNAP-25, SNAP-25 turnover in iNs was measured using the cycloheximide chase method. As shown in FIG. 6E, the SNAP-25 degradation was accelerated in ANCL iNs ($T_{1/2}$~ 12.5 h) compared to WT iNs ($T_{1/2}$>24 h), confirming a defect in the SNAP-25 chaperoning function of CSPα.

Figure 6F:
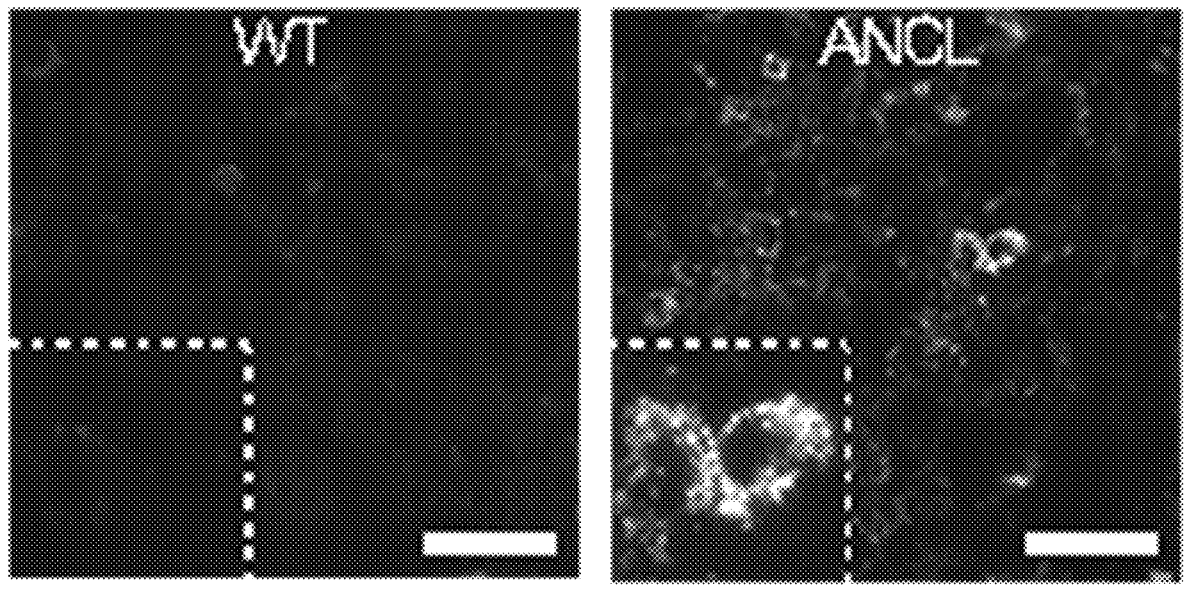
Figure 6G:
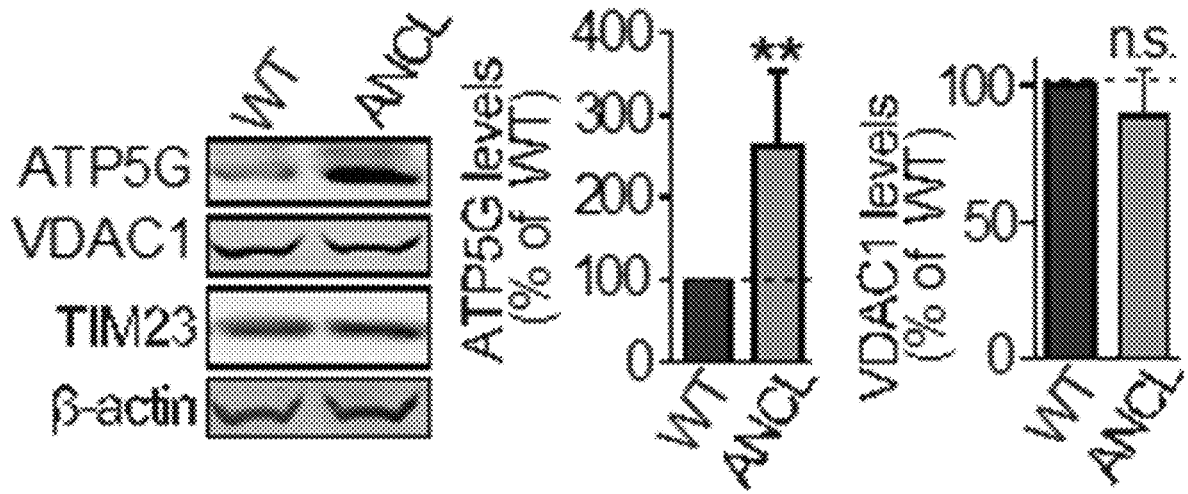
Figure 6H:
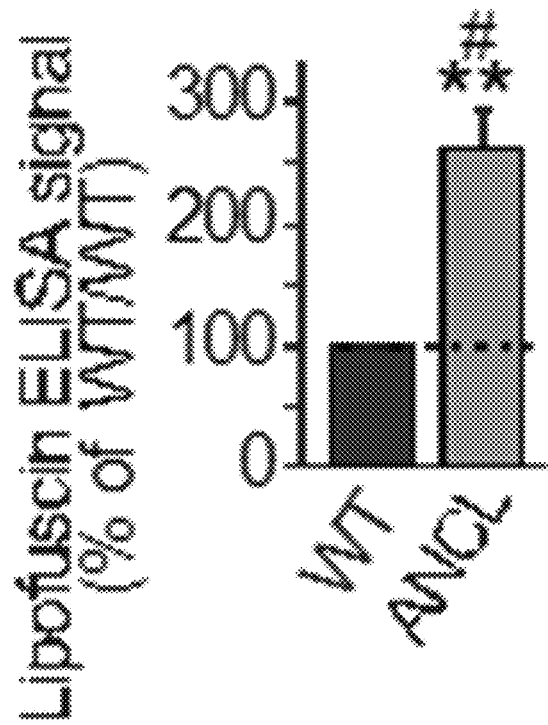

While SNAP-25 is only one of the proposed CSPα clients expressed in neurons (Zhang et al., Neuron 74: 136-150 (2012), the pathological hallmark of ANCL is accumulation of the autofluorescent pigment lipofuscin in neuronal lysosomes. Goebel and Braak: Clin Neuropathol 8: 109-119 (1989); and Anderson et al., Biochim Biophys Acta 1832: 1807-1826 (2013). Unlike primary neurons, the iNs could be maintained for months. Therefore, accumulation of lipofuscin was monitored based on its autofluorescence. As shown in FIG. 6F, maintaining the iNs in culture led to progressive accumulation of lipofuscin in ANCL iNs, as observable by autofluorescence at 56 days post iN conversion. WT iNs did not show accumulation of lipofuscin. The mitochondrial ATP-synthase subunit C (ATP5G) is a major lysosomal storage-component. Hall et al., Biochem J 275 (Pt 1): 269-272 (1991). Levels of ATP5G were quantitated by either ELISA or immunoblotting and normalized to the levels of VDAC1. As shown in FIGS. 6G-6H, ANCL iNs showed increased levels of ATP5G compared to the WT iNs.

These results demonstrate that the iron chelators of the present technology are useful in methods for treating a disease caused by ectopic Fe—S cluster formation, such as ANCL or Kufs disease, in a subject in need thereof.

Example 7: Iron-Chelators Rescue of CSPα ANCL Mutants

Figure 7A:
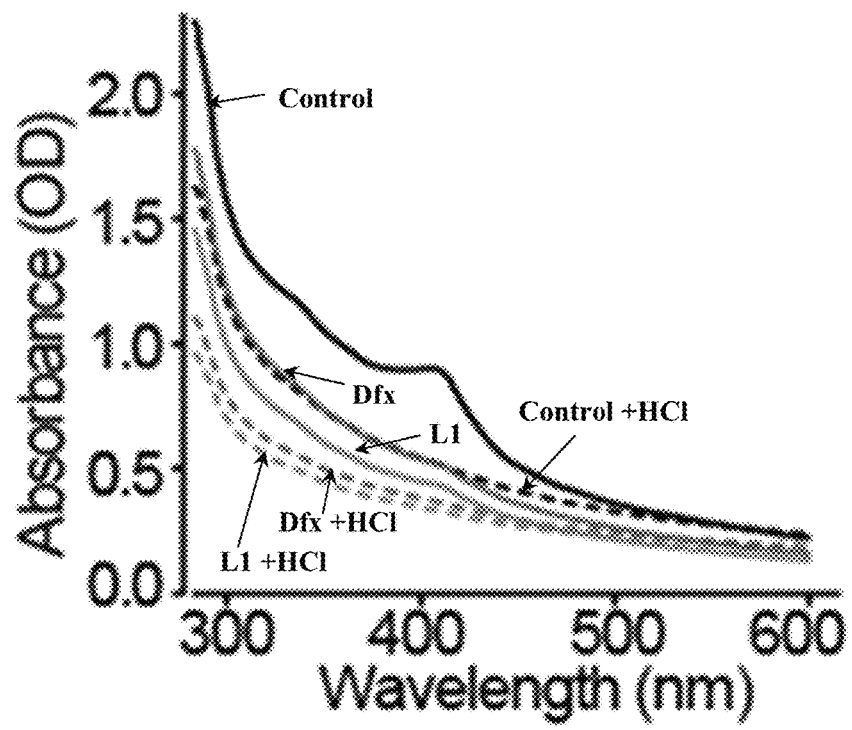
FIGS. 7A-7I show that iron-chelators partially alleviate CSPα oligomerization, the SNAP-25 chaperoning defect, and lipofuscin accumulation in ANCL patient-derived iNs.

CSPα was immunoprecipitated from ANCL fibroblasts and analyzed by UV Vis spectroscopy. As shown in FIG. 7A (solid lines), peaks at ~330 nm and ~417 nm, the characteristic of Fe—S clusters, was evident in ANCL fibroblasts but not in WT fibroblasts (FIG. 6A and data not shown). To evaluate effects of L1 or Dfx on Fe—S cluster formation/binding, WT or ANCL fibroblasts were treated with L1, Dfx or vehicle (negative control). As shown in FIG. 7A, treatment with L1 or Dfx reduced the UV-Vis signature of Fe—S clusters bound to immunoprecipitated CSPα from ANCL fibroblasts compared to the control.

Figure 7B:
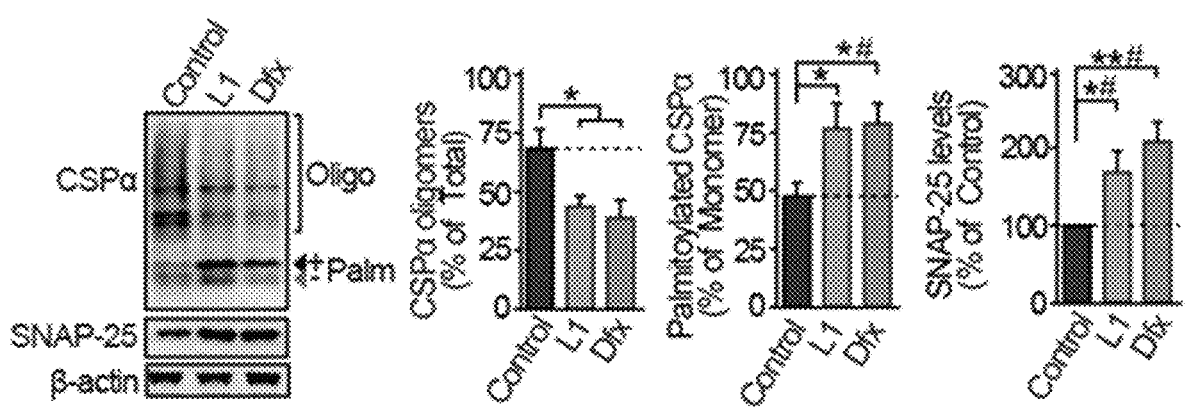
Figure 7C:
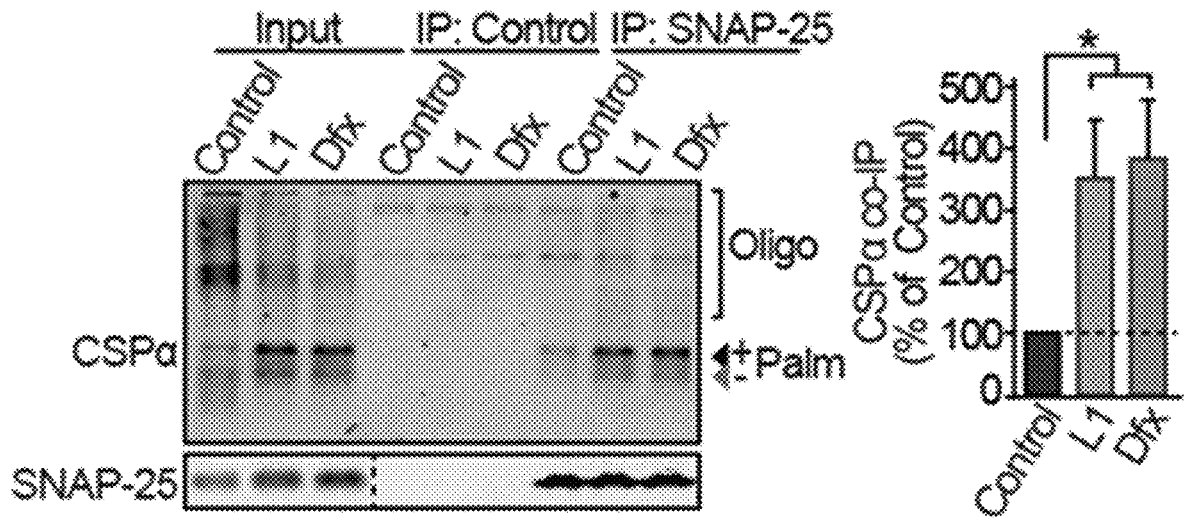
Figure 7D:
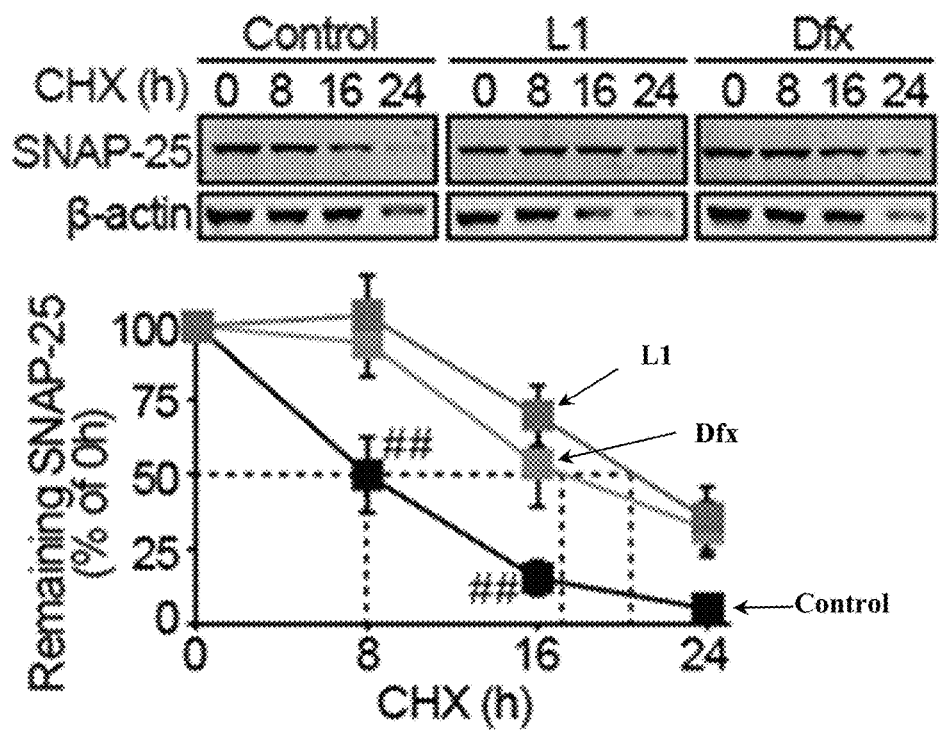

As shown in FIG. 7B, L1 and Dfx also improved palmitoylation and reduced the oligomerization of CSPα in ANCL iNs, compared to the vehicle alone. To understand whether iron chelators have an effect on CSPα with SNAP-25, cell free extracts from control-, L1- or Dfx-treated ANCL iNs were immunoprecipitated with anti-SNAP-25 antibody and co-immunoprecipitation of CSPα was analyzed by immunoblotting. As shown in FIG. 7C, interaction of CSPα with SNAP-25 in ANCL iNs was improved by the treatment with L1- or Dfx compared to the control. As a consequence, SNAP-25 levels in ANCL iNs were augmented by both L1 and Dfx compared to the vehicle only control (FIG. 7B). To find out whether the iron chelators increased stability of SNAP-25, SNAP-25 turnover in iNs was measured using the cycloheximide chase method. As shown in FIG. 7D, the cycloheximide chase studies showed treatment with L1 or Dfx caused decreased turnover of SNAP-25 in ANCL iNs, with ~2× increase in SNAP-25 half-life compared to the control, suggesting that the SNAP-25 chaperoning function of CSPα is restored by these iron-chelators in ANCL patient-derived iNs.

Figure 7E:
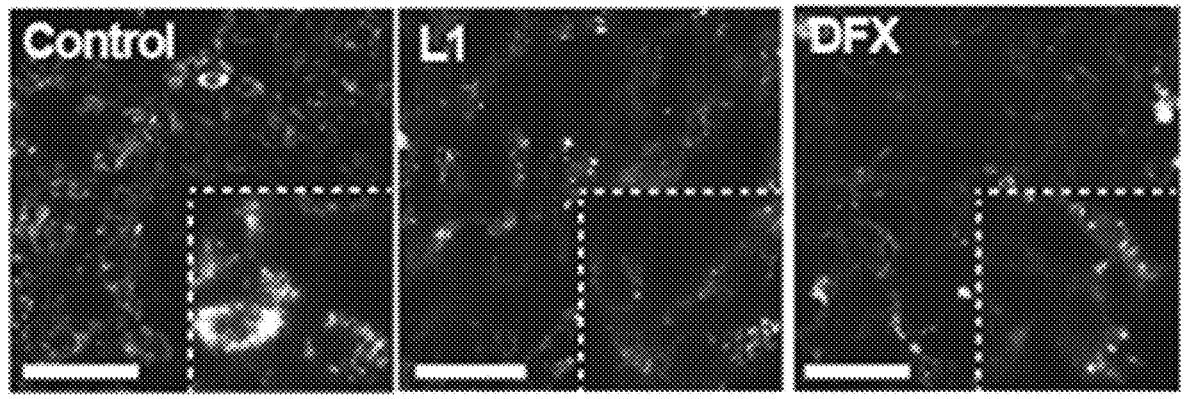
Figure 7F:
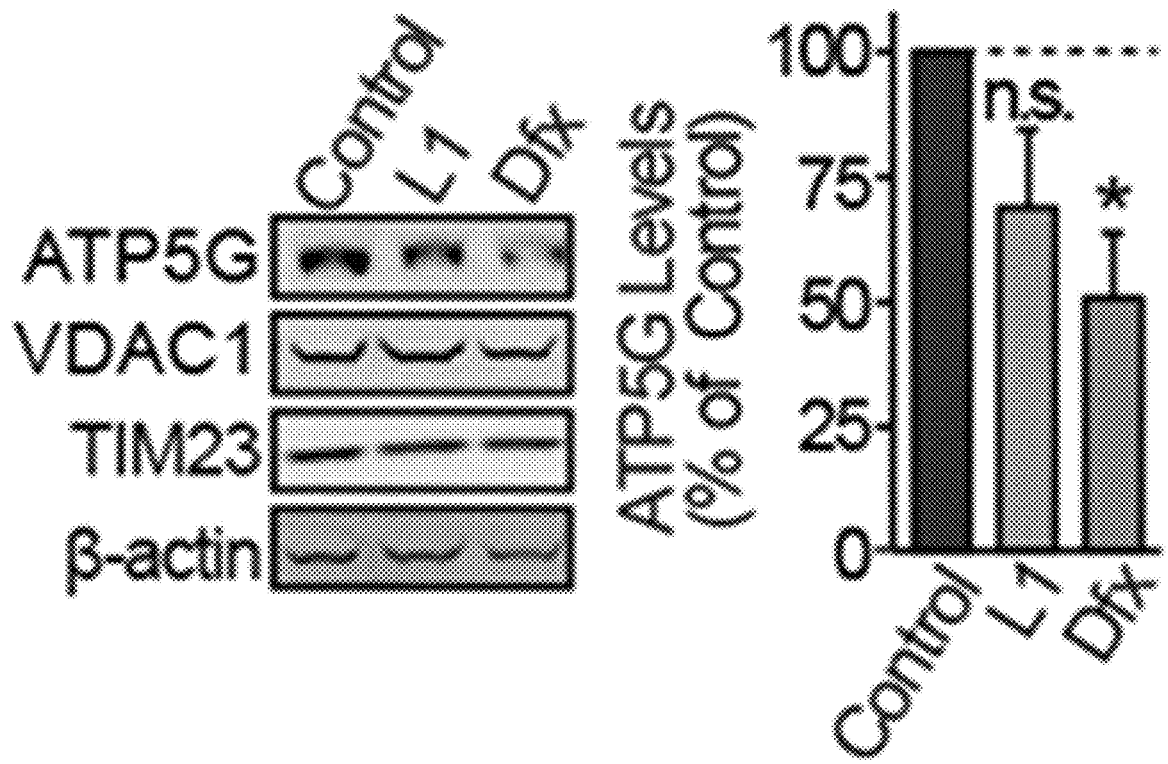
Figure 7G:
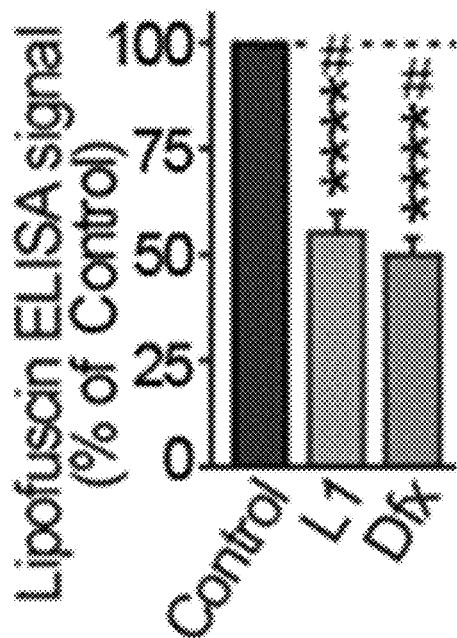

Effect of iron chelators on the accumulation of lipofuscin was monitored by ELISA for lipofuscin or based on lipofuscin autofluorescence. As shown in FIG. 7E, lipofuscin autofluorescence was reduced in ANCL iNs after L1 or Dfx treatment compared to the control. Effect of iron chelators on the accumulation of ATP5G was also studied. As shown in FIG. 7F, the decrease in lipofuscin autofluorescence corresponded with a trend toward reduced accumulation of ATP5G. As shown in FIG. 7G, a significant reduction in lipofuscin ELISA signal was seen following after L1 or Dfx treatment compared to the control.

Figure 7H:
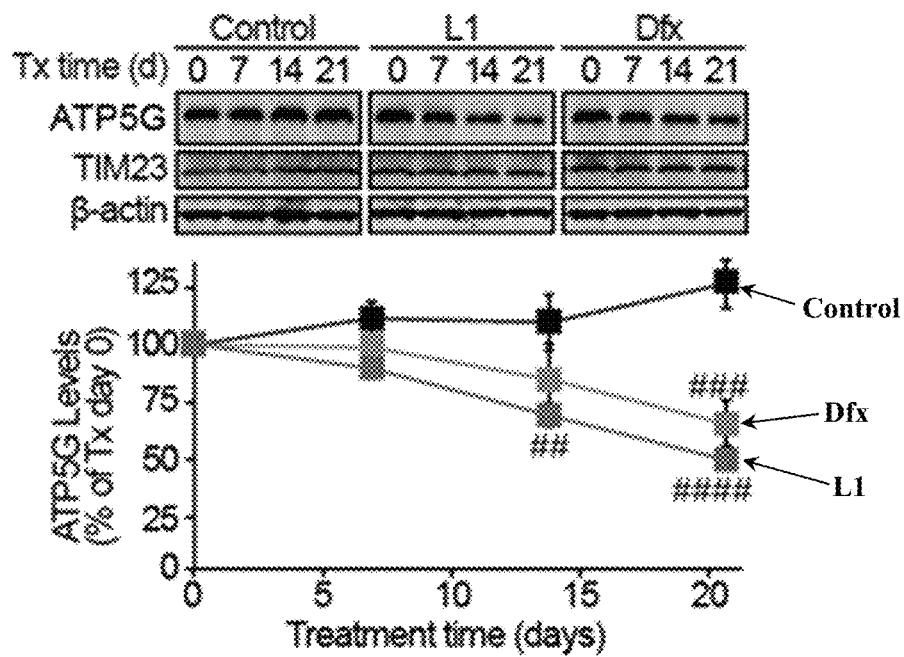
Figure 7I:
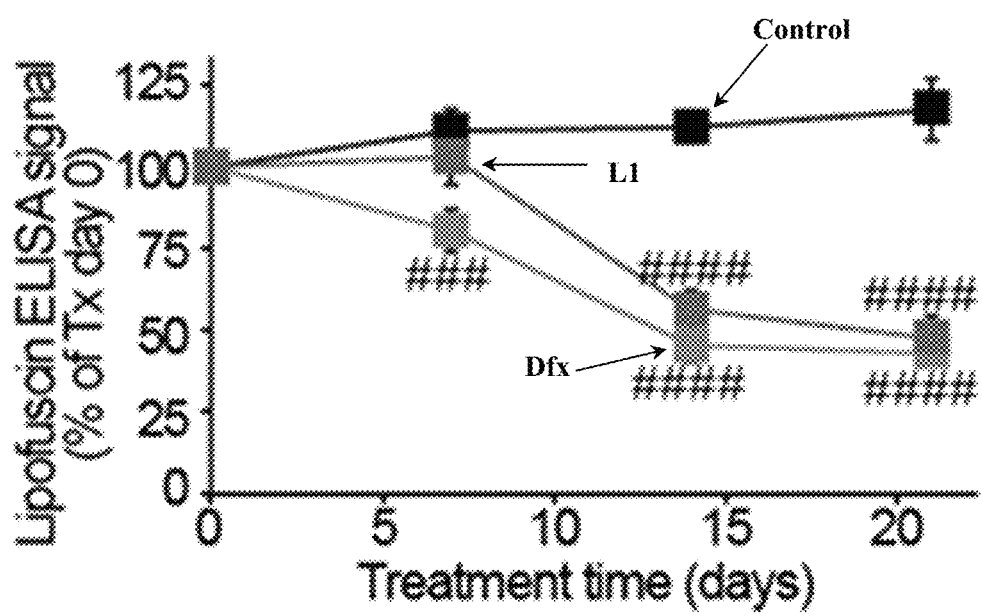

In the above experiments, L1 and Dfx were introduced immediately after fibroblast-to-neuron conversion, suggesting efficacy of the iron-chelators in preventing lipofuscin accumulation. As a treatment paradigm, iron-chelators were also added post-accumulation of lipofuscin. L1 and Dfx were added to ANCL iNs after 56 days of lipofuscin accumulation, and levels of ATP5G and lipofuscin were compared over the subsequent 3 weeks. As shown in FIG. 7H, ATP5G levels were diminished down to similar levels as observed in the prevention experiments by the treatment with L1 or Dfx compared to the control. Further, as shown in FIG. 7I, the levels of lipofuscin were reduced to the levels observed in the prevention experiments by the treatment with L1 or Dfx compared to the control.

Figure 8:
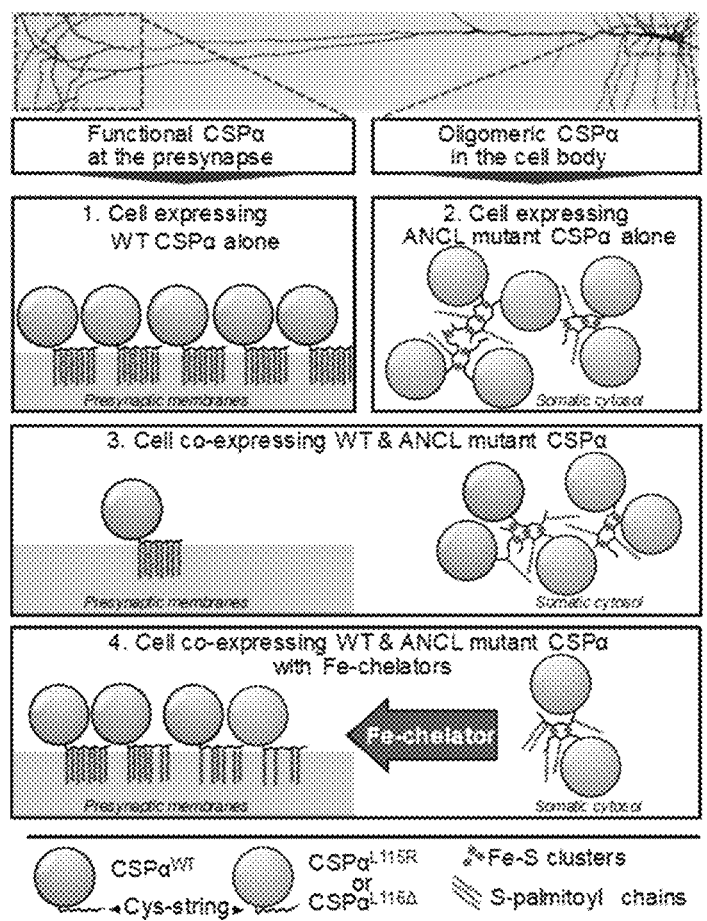
FIG. 8 shows a model inferred from the results disclosed herein. S-palmitoylation of the Cys-string allows presynaptic localization of $CSP\alpha^{WT}$ (panel 1). Loss of palmitoylation in the ANCL mutants $CSP\alpha^{L115R}$ or $CSP\alpha^{L116\Delta}$ accompanies ectopic binding of their reactive Cys-strings to Fe—S clusters, cross-linking the mutant CSPα molecules into oligomers. These oligomers mainly reside away from the synapse, causing loss of CSPα's chaperone function at the synapse (panel 2). In the $CSP\alpha^{L115R}$ or $CSP\alpha^{L116\Delta}$ heterozygous cells, mutant CSPα is able to recruit $CSP\alpha^{WT}$ into oligomers, leading to less than hemizygous level of CSPα function at the synapse (panel 3). Iron-chelator treatment leads to reduction in the Fe—S cluster-bound oligomers, allowing improved CSPα function at the synapse (panel 4). This increase in functional CSPα leads to partial alleviation of the downstream SNAP-25 instability and lipofuscin accumulation phenotypes. Illustration of a pyramidal neuron at the top is modified from a drawing by Santiago Ramón y Cajal.

These results reveal a surprising mechanism for the oligomerization of CSPα carrying ANCL mutations, which had previously been observed. Zhang and Chandra, *Biochim Biophys Acta* 1842: 2136-2146 (2014); and Greaves et al., *J Biol Chem* 287: 37330-37339 (2012), but had remained mechanistically unexplained. As summarized in FIG. 8, the data disclosed herein show that the oligomerization is dependent on binding of Fe—S clusters to the Cys-string, and can be mitigated by iron-chelators, restoring the presynaptic chaperone function of CSPα. Fe—S clusters are known to crosslink proteins into physiological/functional oligomers (Johansson et al., *J Biol Chem* 282: 3077-3082 (2007); and Mesecke et al., *Biochemistry* 47: 1452-1463 (2008)), yet, ectopic binding of Fe—S clusters has never been reported to generate pathogenic oligomers/aggregates. These findings point to pharmacological iron chelation as a potential way to treat ANCL.

These results demonstrate that the iron chelators of the present technology are useful in methods for treating a disease caused by ectopic Fe—S cluster formation, such as ANCL or Kufs disease, in a subject in need thereof.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A method for preventing or treating Kufs Disease in a subject in need thereof, comprising administering to the subject a therapeutically effective amount of an iron chelator, wherein the subject harbors a dominant negative CSPα mutation.

2. The method of claim 1, wherein the dominant negative CSPα mutation is $CSPα^{L115R}$ or $CSPα^{L116Δ}$.

3. The method of claim 1, wherein Kufs disease is Type A Kufs disease or Type B Kufs disease.

4. The method of claim 1, wherein the iron chelator is deferoxamine, desferrithiocin, deferiprone, deferasirox, Apo6619, VK28, pyridoxal isonicotinoyl hydrazone, dexrazoxane, triapine, clioquinol, tachpyr, O-trensox, flavan-3-ol, curcumin, apocynin, kolaviron, floranol, baicalein, baicalin, di-2-pyridylketone thiosemicarbazone, ligustrazine, quercetin, epigallocatechin gallate, theaflavin, phytic acid, genistein, dimercaptosuccinic acid, 2,3-dimercapto-1-propanesulfonic acid (DMPS), alpha lipoic acid (ALA), or any pharmaceutically acceptable salt thereof.

5. The method of claim 1, wherein the subject exhibits one or more symptoms selected from the group consisting of progressive dementia, epilepsy, cerebellar and/or extrapyramidal symptoms, myoclonus, vision loss, seizures, ataxia, tremors and tics, dysarthria, speech difficulties, confusion, involuntary movements, and psychotic behaviour.

6. The method of claim 1, wherein the subject harbors at least one mutation in one or more genes selected from the group consisting of CLN6, PPT1, DNAJC5, CTSF, CLN5, GRN, and CLN3.

7. The method of claim 1, wherein the iron chelator is administered intravenously, intramuscularly, intraarterially, intrathecally, intracapsularly, intraorbitally, intradermally, intraperitoneally, transtracheally, subcutaneously, intracerebroventricularly, orally, topically, or intranasally.

8. The method of claim 1, wherein the iron chelator is sequentially, simultaneously, or separately administered with at least one additional therapeutic agent.

9. The method of claim 1, wherein the disease associated with ectopic iron-sulfur (Fe—S) cluster formation, or the disease associated with ectopic binding of one or more proteins to iron-sulfur (Fe—S) cluster is characterized by reduced SNAP-25 proteins levels, decreased SNARE-complex assembly, or elevated levels of lipofuscin and/or mitochondrial ATP-synthase subunit C (ATP5G) in neurons.

10. The method of claim 5, wherein the involuntary movements comprises one or more of tics, tremors, and facial dyskinesia.

* * * * *

SEQUENCE LISTING

```
<160> NUMBER OF SEQ ID NOS: 2

<210> SEQ ID NO 1
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu Leu Thr Ser Ser Tyr Ser Ser Ser Leu Ser Ser Ser Phe Asn
1               5                   10                  15

Ser Ser Ser Gly Lys Ser Lys Pro
            20

<210> SEQ ID NO 2
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Met Glu Gln Lys Leu Ile Ser Glu Glu Asp Leu Asn Glu Phe Gly Gln
1               5                   10                  15

Gly Ala Gln Gly Gln Leu
            20
```